United States Patent
Shi et al.

(10) Patent No.: US 8,796,314 B2
(45) Date of Patent: Aug. 5, 2014

(54) HETEROARYLS AND USES THEREOF

(75) Inventors: Zhan Shi, Concord, MA (US); Irache Visiers, Arlington, MA (US); Tricia J. Vos, Medford, MA (US); Stepan Vyskocil, Arlington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 545 days.

(21) Appl. No.: 12/657,801

(22) Filed: Jan. 28, 2010

(65) Prior Publication Data

US 2010/0256172 A1    Oct. 7, 2010

Related U.S. Application Data

(60) Provisional application No. 61/206,417, filed on Jan. 30, 2009, provisional application No. 61/229,399, filed on Jul. 29, 2009.

(51) Int. Cl.
| | |
|---|---|
| *A61K 31/506* | (2006.01) |
| *A61K 31/497* | (2006.01) |
| *A61K 31/444* | (2006.01) |
| *A61K 31/4439* | (2006.01) |
| *A61K 31/4436* | (2006.01) |
| *C07D 409/14* | (2006.01) |
| *C07D 409/04* | (2006.01) |

(52) U.S. Cl.
CPC ........... *A61K 31/4439* (2013.01); *A61K 31/506* (2013.01); *A61K 31/497* (2013.01); *A61K 31/444* (2013.01); *A61K 31/4436* (2013.01); *C07D 409/14* (2013.01); *C07D 409/04* (2013.01)
USPC ...... 514/341; 514/255.05; 514/275; 514/256; 514/333; 514/343; 514/340; 544/405; 544/331; 544/328; 544/327; 546/272.4; 546/275.1; 546/272.7; 546/280.4; 546/274.4; 546/272.1; 546/281.4; 546/268.4; 546/275.4; 546/256

(58) Field of Classification Search
CPC . A61K 31/506; A61K 31/497; A61K 31/444; A61K 31/4439; A61K 31/4436; C07D 409/14; C07D 409/04
USPC ............ 514/255.05, 275, 256, 333, 341, 343, 514/340; 544/405, 331, 328, 327; 546/272.4, 275.1, 272.7, 280.4, 274.7, 546/272.1, 281.4, 268.4, 275.4, 256
See application file for complete search history.

(56) References Cited

U.S. PATENT DOCUMENTS

| | | | |
|---|---|---|---|
| 3,257,203 A | 6/1966 | Sus et al. | |
| 3,821,384 A | 6/1974 | Ariyan et al. | |
| 3,852,293 A | 12/1974 | Ariyan et al. | |
| 4,371,607 A | 2/1983 | Donges | |
| 5,134,142 A | 7/1992 | Matsuo et al. | |
| 6,015,826 A | 1/2000 | Pechacek et al. | |
| 6,608,087 B1 | 8/2003 | Charifson et al. | |
| 6,984,652 B2 | 1/2006 | Yager et al. | |
| 7,405,235 B2 | 7/2008 | Levy et al. | |
| 7,504,513 B2 | 3/2009 | Boylan et al. | |
| 7,741,348 B2 | 6/2010 | Nan et al. | |
| 8,440,664 B2 | 5/2013 | Cardin et al. | |
| 8,586,582 B2 | 11/2013 | Liang et al. | |
| 2002/0022729 A1 | 2/2002 | Kawai et al. | |
| 2003/0096816 A1 | 5/2003 | Cao et al. | |
| 2004/0116425 A1 | 6/2004 | Li et al. | |
| 2004/0198773 A1 | 10/2004 | Hart et al. | |
| 2004/0248896 A1 | 12/2004 | Dean et al. | |
| 2005/0004122 A1 | 1/2005 | Brown et al. | |
| 2005/0054697 A1 | 3/2005 | Yager et al. | |
| 2005/0124678 A1 | 6/2005 | Levy et al. | |
| 2006/0041006 A1 | 2/2006 | Ibrahim et al. | |
| 2006/0074119 A1 | 4/2006 | Andrews et al. | |
| 2006/0199804 A1 | 9/2006 | Hummersone et al. | |
| 2007/0203210 A1 | 8/2007 | Boylan et al. | |
| 2008/0021217 A1 | 1/2008 | Borchardt et al. | |

(Continued)

FOREIGN PATENT DOCUMENTS

| | | |
|---|---|---|
| DE | 275870 A1 | 2/1990 |
| EP | 0853083 A1 | 7/1998 |

(Continued)

OTHER PUBLICATIONS

Lucchesini, F. Tetrahedron 1992, 48, 9951-9966.*

(Continued)

*Primary Examiner* — Joseph Kosack
*Assistant Examiner* — Matthew Coughlin
(74) *Attorney, Agent, or Firm* — Choate, Hall & Stewart LLP; Andrea L. C. Reid

(57) ABSTRACT

This invention provides compounds of formula I:

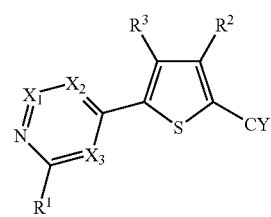

wherein $R^1$, $R^2$, $R^3$, CY, $X_1$, $X_2$, and $X_3$ are as described in the specification. The compounds are inhibitors of PI3K and are thus useful for treating proliferative, inflammatory, or cardiovascular disorders.

21 Claims, No Drawings

(56) References Cited

U.S. PATENT DOCUMENTS

| | | |
|---|---|---|
| 2008/0045570 A1 | 2/2008 | Brenchley et al. |
| 2008/0132546 A1 | 6/2008 | Basarab et al. |
| 2008/0255120 A1 | 10/2008 | Lin et al. |
| 2008/0293716 A1 | 11/2008 | Drewry et al. |
| 2008/0306060 A1 | 12/2008 | Alexander et al. |
| 2009/0012031 A1 | 1/2009 | Chinnaiyan et al. |
| 2009/0030016 A1 | 1/2009 | Gandhi et al. |
| 2009/0036435 A1 | 2/2009 | Curry et al. |
| 2009/0247567 A1 | 10/2009 | Do et al. |
| 2009/0325925 A1 | 12/2009 | Renou et al. |
| 2010/0075951 A1 | 3/2010 | Cardin et al. |
| 2010/0267759 A1 | 10/2010 | Seefeld et al. |
| 2011/0003806 A1 | 1/2011 | Hirose et al. |
| 2011/0003807 A1 | 1/2011 | Banno et al. |
| 2011/0021531 A1 | 1/2011 | Chobanian et al. |
| 2012/0142732 A1 | 6/2012 | Cullis et al. |
| 2012/0172345 A1 | 7/2012 | Freeze et al. |
| 2012/0178723 A1 | 7/2012 | Hirose et al. |
| 2012/0214794 A1 | 8/2012 | Freeze et al. |
| 2013/0165464 A1 | 6/2013 | Chau et al. |
| 2013/0165472 A1 | 6/2013 | Chau et al. |
| 2013/0165483 A1 | 6/2013 | Chau et al. |
| 2013/0217689 A1 | 8/2013 | Cardin et al. |
| 2013/0267563 A1 | 10/2013 | Hirose et al. |

FOREIGN PATENT DOCUMENTS

| | | |
|---|---|---|
| GB | 874634 A | 8/1961 |
| JP | 10087490 | 4/1998 |
| JP | 2007-197324 A | 8/2007 |
| WO | WO-97/12615 A1 | 4/1997 |
| WO | WO-98/08845 A1 | 3/1998 |
| WO | WO-98/47894 A1 | 10/1998 |
| WO | WO-00/02871 A1 | 1/2000 |
| WO | WO-00/35912 A1 | 6/2000 |
| WO | WO-00/63204 A2 | 10/2000 |
| WO | WO-02/088107 A1 | 11/2002 |
| WO | WO-03/015776 A1 | 2/2003 |
| WO | WO-03/027085 A2 | 4/2003 |
| WO | WO-03/027107 A1 | 4/2003 |
| WO | WO-03/040096 A2 | 5/2003 |
| WO | WO-2004/016592 A1 | 2/2004 |
| WO | WO-2004/016741 A2 | 2/2004 |
| WO | WO-2004/096797 A1 | 11/2004 |
| WO | WO-2006/046031 A1 | 5/2006 |
| WO | WO-2006/068933 A2 | 6/2006 |
| WO | WO-2006/078287 A2 | 7/2006 |
| WO | WO-2006/097030 A1 | 9/2006 |
| WO | WO-2006/102194 A1 | 9/2006 |
| WO | WO-2006/114313 A1 | 11/2006 |
| WO | WO-2006/114343 A1 | 11/2006 |
| WO | WO-2007/002559 A1 | 1/2007 |
| WO | WO-2007/043400 A1 | 4/2007 |
| WO | WO-2007/087488 A2 | 8/2007 |
| WO | WO-2007/096315 A1 | 8/2007 |
| WO | WO-2007/110344 A1 | 10/2007 |
| WO | WO-2007/129044 A1 | 11/2007 |
| WO | WO-2007/129161 A2 | 11/2007 |
| WO | WO-2007/138110 A2 | 12/2007 |
| WO | WO-2008/014238 A2 | 1/2008 |
| WO | WO-2008/021235 A2 | 2/2008 |
| WO | WO-2008/023159 A1 | 2/2008 |
| WO | WO-2008/024980 A2 | 2/2008 |
| WO | WO-2008/036541 A1 | 3/2008 |
| WO | WO-2008/083070 A1 | 7/2008 |
| WO | WO-2008/090382 A1 | 7/2008 |
| WO | WO-2008/097835 A2 | 8/2008 |
| WO | WO-2008/098105 A1 | 8/2008 |
| WO | WO-2008/134679 A1 | 11/2008 |
| WO | WO-2008/139161 A1 | 11/2008 |
| WO | WO-2008/157273 A1 | 12/2008 |
| WO | WO-2009/040730 A2 | 4/2009 |
| WO | WO-2009/042607 A1 | 4/2009 |
| WO | WO-2009/049028 A1 | 4/2009 |
| WO | WO-2009/094224 A1 | 7/2009 |
| WO | WO-2009/106885 A1 | 9/2009 |
| WO | WO-2009/122148 A1 | 10/2009 |
| WO | WO-2009/154741 A1 | 12/2009 |
| WO | WO-2009/158374 A2 | 12/2009 |
| WO | WO-2010/001126 A1 | 1/2010 |
| WO | WO-2010/005841 A1 | 1/2010 |
| WO | WO-2010/017079 A1 | 2/2010 |
| WO | WO-2010/055304 A2 | 5/2010 |
| WO | WO-2010/080873 A1 | 7/2010 |
| WO | WO-2010/090716 A1 | 8/2010 |
| WO | WO-2010/132598 A1 | 11/2010 |
| WO | WO-2011/043371 A1 | 4/2011 |

OTHER PUBLICATIONS

2-Thiophenecarboxylic acid, 3-(4-chlorophenyl)-4-cyano-5-(4-morpholinyl)-(CA Index Name), CAS Registry No. 883097-33-4, entered May 5, 2006.

2-Thiophenecarboxylic acid, 3-(4-chlorophenyl)-4-cyano-5-(4-morpholinyl)-, methyl ester (CA Index Name), CAS Registry No. 882283-38-7, entered Apr. 30, 2006.

4-Oxazolecarboxylic acid, 5-[(ethoxymethylene)amino]-2-(4-pyridinyl)-, ethyl ester- (CA Index Name), CAS Registry No. 885901-22-4, entered May 29, 2006.

Abdelrazek et al., Heterocyclic Synthesis with Nitriles: Synthesis of Some Novel Thiophene and Thieno[2,3-d]Pyrimidine Derivatives, Phosphorus, Sulfur, Silicons, 71:93-97 (1992).

Adib et al., Facile One-Pot Three-Component Synthesis of Functionalized Pyridylfuran-2-amines, Helvetica Chimica Acta, 89(2):299-303 (2006).

Al-Azawe et al., Synthesis of 2, 5-Disubstituted Thiazoles and Their Reactions with Grignard Reagents, Journal of the Iraqi Chemical Society, 13(1): 1-13 (1988).

Batista et al., Synthesis and characterization of new thienylpyrrolyl-benzothiazoles as efficient and thermally stable nonlinear optical chromophores, Tetrahedron, 63(20):4258-4265 (2007).

Batista et al., Synthesis and Second-Order Nonlinear Optical Properties of New Chromophores Containing Benzimidazole, Thiophene, and Pyrrole Heterocycles, Tetrahedron, 63(39): 9842-9849 (2007).

Berndt et al., The p110δ crystal structure uncovers mechanisms for selectivity and potency of novel PI3K inhibitors, Nature Chemical Biology, 6(2):117-124 (2010).

Boppana, K. et al., Knowledge based identification of MAO-B selective inhibitors using pharmacophore and structure based virtual screening models, European Journal of Medicinal Chemistry, 44:3584-3590 (2009).

Chattopadhyay, S. K. et al., Efficient Construction of the Carbon Skeleton of the Novel Polyoxazole-Based Cyclopeptide IB-01211 via a Biomimetic Macrocyclisation, SYNLETT, 4:555-558 (2010).

Choi, W. et al., Synthesis and Antiproliferative Activities of 1-Substituted-3-(3-chloro-5-methoxyphenyl)-4-pyridinylpyrazole Derivatives Against Melanoma Cell Line, Bulletin of the Korean Chemical Society, 30(9):2027-2031 (2009).

Cudworth et al., Structure—Activity Relationship Development of Dihaloaryl Triazole Compounds as Insecticides and Acaricides. 1. Phenyl Thiophen-2-yl Triazoles, Journal of Agricultural and Food Chemistry, 55(18): 7517-7526 (2007).

Database CHEMCATS, Chemical Abstracts Service, Columbus, Ohio, US, XP002545555, order No. T5337328.

Datta et al., A Novel Route to Methyl 3-3(3,4-Disubstituted 5-alkylthio/amino-2-thienyl) propenoates, Synthesis, 7:556-567 (1988).

Emmitte et al., Discovery of Thiophene Inhibitors of Polo-like Kinase, Bioorganic & Medicinal Chemistry Letters, 19(3): 1018-1021 (2009).

Fletcher, A. N. et al., Laser Dye Stability, Part 12. The Pyridinium Salts, Applied Physics, B43:155-160 (1987).

Fridman et al., Spectroscopy, Photophysical and Photochemical Properties of Bisimidazole, Derivatives, Journal of Photochemisty and Photobiology, A: Chemistry, 188(1): 25-33 (2007).

Green et al., Parallel Synthesis of 2-aryl-4-aminobenzimidazoles and their Evaluation as Gonadotropin Releasing Hormone Antagonists, Journal of Combinatorial Chemistry, 11(1): 117-125 (2009).

(56) References Cited

OTHER PUBLICATIONS

Hernandez, D. et al., Synthesis and Antitumor Activity of Mechercharmycin A Analogues, Journal of Medicinal Chemistry, 51: 5722-5730 (2008).
Hernandez, D. et al., Synthesis of Natural Product Derivatives Containing 2,4-Concatenated Oxazoles, European Journal of Organic Chemistry, (19): 3389-3396 (2008).
Heyde et al., A Simple Route to N,N-Dialkyl Derivatives of 2-Amino-5-thiophenecarboxylates, Eur. J. Org. Chem.: 3273-3278 (2000).
Hirai et al., Heterocyclic Cation Systems. 14. Sythesis of Thieno[3,2-e][1,4]diazepine, Thiazolo[4,5-e][1,4]diazepine, and s-Triazolo[3,4-c]thiazolo[4,5-e][1,4]diazepine Derivatives, Journal of Organic Chemistry, 45:253-260 (1980).
Hirai et al., Novel Synthesis of Thiophene Derivatives from 1,3-Oxathil-2-ylideneimmonium Salt, Chemical & Pharmaceutical Bulletin, 19(10): 2194-2197 (1971).
International Search Report for PCT/US09/00513, which relates to U.S. Appl. No. 12/321,871, 3 pages (Jun. 10, 2009).
International Search Report for PCT/US09/03607, which relates to U.S. Appl. No. 12/456,455, U.S. Appl. No. 13/854,409, and U.S. Appl. No. 13/449,341, 4 pages (Sep. 23, 2009).
International Search Report for PCT/US10/00234, which relates to U.S. Appl. No. 12/657,853, 3 pages (Jun. 1, 2010).
International Search Report for PCT/US11/47245, which relates to U.S. Appl. No. 13/206,671, 2 pages (Dec. 22, 2011).
International Search Report for PCT/US11/47407, which relates to U.S. Appl. No. 13/207,753, 2 pages (Dec. 22, 2011).
International Search Report for PCT/US11/56135, which relates to U.S. Appl. No. 13/272,413, 4 pages (May 31, 2012).
Laszlo et al., Pyrroles and Other Heterocycles as Inhibitors of P38 Kinase, Bioorganic and Medical Chemistry Letters, 8: 2689-2694 (1998).
Lethu et al., Discovery of a New Class of Protein Farnesyltransferase Inhibitors in the Arylthiophene Series, J. Med. Chem., 52: 6205-6208 (2009).
Liang, J. et al., Crystal Structure of P13K SH3 Domain at 2.0 A Resolution, Journal of Molecular Biology, 257:632-643 (1996).
Liu et al., Highly Selective and Potent Thiophenes as P13K Inhibitors with Oral Antitumor Activity, Med. Chem. Lett., 2:809-813 (2011).
Mamedov et al., Synthesis and Some Properties of the Methyl Ester and N,N-diethylamide of 2-Azido-5-Phyenyl-4-Thiazolecarboxylic Acic, Chemistry of Heterocyclic Compounds, 29(5): 607-611 (1993).
Matschke et al., Quinomethides Versus Unsymmetric Hybrids: Two Variations of Non-Radicaloid SEM-States in Four-Electron Redox Systems of bis-4H-imidazoles, Structural Chemistry, 19(3):399-405 (2008).
Menear, K. A. et al., Identification and optimisation of novel and selective small molecular weight kinase inhibitors of mTOR, Bioorganic & Medicinal Chemistry Letters, 19:5898-5901 (2009).
Moorthy et al., In Silico-Based Structural Analysis of Arylthiophene Derivatives for Ftase Inhibitory Activity, hERG, and Other Toxic Effects, Journal of Biomolecular Screening, 16(9):1037-1046 (2011).
Morpholine, 4-(5-(4,5-diphenyl-1H-imidazol-2-y1)-2-thienyl]-, Ryan Scientific Screening Library, Publication date: Jan. 25, 2008, CAS Registry No. 851954-74-0.
Nagasaki et al., CASREACT 139:52925 (2003).
Nagasaki et al., Useful Synthesis of Various Thiazole and Polythiazolyl Derivatives from Thiocarboxamide and -Bromacyl Compound, Heterocycles, 60(2): 321-335 (2003).
Pinto et al., The Synthesis of 5-alkoxy and 5-amino Substituted Thiophenes, Tetrahedron Letters, 41(10): 1597-1600 (2000).
Raap, Some Synthesis with Dimethyl Monothionemalonate, Canadian Journal of Chemistry, 46:13, 2255-2261 (1968).
Rehwald et al., New Synthesis of 2,4-Diaminothiophenes- Use of (1,3-oxathioI-2-ylidene)Malononitrile, Heterocycles, 45(3): 493-500 (1997).

Revesz, L. et al., SAR of 2,6-Diamino-3,5-difluoropyridinyl Substituted Heterocycles as Novel p38 MAP Kinase Inhibitors, Bioorganic & Medicinal Chemistry Letters, 12(16):2109-2112 (2002).
Sheridan, The Most Common Chemical Replacements in Drug-Like Compounds, J. Chem. Inf. Comput. Sci., 42:103-108 (2002).
Thompson, M.J. et al., Development of a Diversity-Oriented Approach to Oxazole-5-amide Libraries, Journal of Organic Chemistry, 74(10):3856-3865 (2009).
Wang, Q. et al., Copper-Mediated Amidation of Heterocyclic and Aromatic C-H Bonds, Organic Letters, 11( 22): 5178-5180 (2009).
Written Opinion for PCT/US09/00513, which relates to U.S. Appl. No. 12/321,871, 5 pages (Jun. 10, 2009).
Written Opinion for PCT/US09/03607, which relates to U.S. Appl. No. 12/456,455, U.S. Appl. No. 13/854,409, and U.S. Appl. No. 13/449,341, 5 pages (Sep. 23, 2009).
Written Opinion for PCT/US10/00234, which relates to U.S. Appl. No. 12/657,853, 6 pages (Jun. 1, 2010).
Written Opinion for PCT/US11/47245, which relates to U.S. Appl. No. 13/206,671, 5 pages (Dec. 22, 2011).
Written Opinion for PCT/US11/47407, which relates to U.S. Appl. No. 13/207,753, 7 pages (Jun. 10, 2009).
Written Opinion for PCT/US11/56135, which relates to U.S. Appl. No. 13/272,413, 13 pages (May 31, 2012).
Zhang, F. et al., Decarboxylative C-H Cross-Coupling of Azoles, Angew. Chem. Int. Ed., 49(15): 2768-2771 (2010).
Zhou et al., Selenium-Containing Heterocycles from Isoselenocyanates: Synthesis of 1,3-Selenazoles from N-Phenylimidoyl Isoselenocyanates, Helvetica Chimica Acta, 83: 1576-1598 (2000).
Benzamide, N-[2-(5-amino-1-phenyl-1H-pyrazol-4-yl)-4-phenyl-5-thiazoly1]-4-methyl-(CA Index Name), CAS Registry No. 1017527-68-2, entered Apr. 27, 2008.
5-Thiazolecarboxamide, N-[2'-(aminosulfony1)[1,1'-biphenyl]-2-yl]-4-(4-methoxypheny1)-2-(1H-pyrrol-1-yl)- (CA Index Name), CAS Registry No. 1027033-64-2, entered Jun. 10, 2008.
1,2,4-Oxadiazole-3-ethanamine, 5-[5-(1H-imidazol-2-yl)-2-thienyl]-N,N-dimethyl- (CA Index Name), CAS Registry No. 1066888-52-5, entered Oct. 27, 2008.
1,2,4-Oxadiazole, 5-[5-(1 H-imidazol-2-yl)-2-thienyl]-3-(methoxymethyl)-(CA Index Name), CAS Registry No. 1069660-66-7, entered Nov. 2, 2008.
2,7-Naphthyridine, 1,2,3,4-tetrahydro-5[5[5-(1H-imidazol-2-y1)-2-thienyl]-1,2,4-oxadiazol-3-yl]-6-methyl-(CA Index Name), CAS Registry No. 1069717-72-1, entered Nov. 2, 2008.
Pyrazolo[1,5-a]pyrimidin-7(4H)-one,3-ethyl-5[5-(1H-imidazol-2-yl)-2-thienyl]-(CA Index Name) CAS Registry No. 1087437-07-7, entered Dec. 21, 2008.
3H-1,2,4-Triazole-3-thione, 2,4-dihydro-4-methyl-5-[4-methyl-2-(5-methyl-3-isoxazoly1)-5-thiazolyl]-(CA Index Name), CAS Registry No. 264616-86-6, entered May 12, 2000.
Acetamide, N-(3,5-dichloropheny1)-2-[[4-methyl-5-[4-methyl-2-(5-methyl-3-isoxazoly1)-5-thiazolyl]-4H-1,2,4-triazol-3-yl]thio]- (CA Index Name), CAS Registry No. 264626-19-9, entered May 12, 2000.
Acetamide, N-(4-chloropheny1)-2-[[4-methyl-5-[4-methyl-2-(5-methyl-3-isoxazoly1)-5-thiazolyl]- 4H-1,2,4-triazol-3-yl]thio]-(CA Index Name), CAS Registry No. 264626-21-3, entered May 12, 2000.
Carbamic acid,4,4'-diphenyl[2,2'-bithiazole]-5,5'-diyl)bis-, dimethyl ester (9CI)(CA Index Name), CAS Registry No. 505060-78-6, entered Apr. 25, 2003.
Benzamide, N,N'-(4,4'-di-2-thienyl[2,2'-bithiazole]-5,5'-diyl)bis- (CA Index Name) CAS Registry No. 691381-57-4, entered Jun. 10, 2004.
Carbamic acid, N,N'-(4,4'-di-2-thienyl[2,2'-bithiazole]-5,5'-diyl)bis-,C,C'-dimethyl ester (CA Index Name) CAS Registry No. 691381-58-5, entered Jun. 10, 2004.
Benzamide, N,N'-[4,4'-bis(4-fluoropheny1)[2,2'-bithiazole]-5,5'-diyl]bis[4-methyl- (CA Index Name) CAS Registry No. 691381-60-9, entered Jun. 10, 2004.
Imidazo[1,2-a]pyridine, 6-[3-[5-(2H-tetrazol-5-yl)-2-thienyl]-1H-pyrazol-4-yl]-3-(2-thiazolyl)-(CA Index Name) CAS Registry No. 732241-18-8, entered Aug. 25, 2004).

(56) References Cited

OTHER PUBLICATIONS

Benzamide, N-(4'-amino-2',3'-dihydro-3',4-diphenyl-2'-thioxo[2,5'-bithiazol]-5-yl)- (CA Index Name)CAS Registry No. 879910-33-5, entered Apr. 10, 2006.
2-Thiazolamine, 4-[5-(2H-tetrazol-5-yl)-2-thienyl]- (CA Index Name), CAS Registry No. 937625-84-8, entered Jun. 17, 2007.
1H-Pyrazole-1-carboxylic acid, 5-[2,2'-bithiophen]-5-yl-, ethyl ester (CA Index Name), CAS Registry No. 957595-63-0, entered Dec. 12, 2007.
4-Thiazolecarboxamide, 2-(4-acetyl-5-methyl-1H-1,2,3-triazol-1-yl)-N,N-diethyl-5-phenyl- (CA Index Name), CAS Registry No. 709639-21-4, entered Jul. 14, 2004.
Database CAS Registry (Columbus, Ohio), RN 893689-50-4 (Entered Jul. 17, 2006).
Database CAS Registry (Columbus, Ohio), RN 893692-42-7 (Entered Jul. 17, 2006).
Database CAS Registry (Columbus, Ohio), RN 893704-20-6 (Entered Jul. 17, 2006).
Database CAS Registry (Columbus, Ohio), RN 893705-40-3 (Entered Jul. 17, 2006).
Database CAS Registry (Columbus, Ohio), RN 898517-78-7 (Entered Aug. 3, 2006).
Welker et al., Recent Syntheses of PI3K/Akt/mTOR signaling pathway inhibirots, Bioorganic & Medicinal Chemistry, 21(14): 4063-4091 (2013).

* cited by examiner

HETEROARYLS AND USES THEREOF

The present application claims the benefit of U.S. Provisional Application Ser. No. 61/206,417, filed Jan. 30, 2009 (pending) and U.S. Provisional Application Ser. No. 61/229,399, filed Jul. 29, 2009 (pending). The entire contents of each of the above-referenced patent applications are incorporated herein by this reference.

BACKGROUND OF THE INVENTION

Phosphatidylinositol 3-kinase (PI3K) is a family of lipid kinases that phosphorylate phosphatidylinositol at the 3' position of the inositol ring. PI3K is comprised of several classes of genes, including Class IA, IB, II and III and some of these classes contain several isoforms (reviewed in Engelman et al., Nature Review Genetics 7:606-619 (2006)). Adding to the complexity of this family is the fact that PI3Ks function as heterodimers, comprising a catalytic domain and a regulatory domain. The PI3K family is structurally related to a larger group of lipid and serine/threonine protein kinases known as the phosphatidylinositol 3-kinase like kinases (PIKKs), which also includes DNA-PK, ATM, ATR, mTOR, TRRAP and SMG1.

PI3K is activated downstream of various mitogenic signals mediated through receptor tyrosine kinases, and subsequently stimulates a variety of biological outcomes; including increased cell survival, cell cycle progression, cell growth, cell metabolism, cell migration and angiogenesis (reviewed in Cantley, Science 296:1655-57 (2002); Hennessy et al., Nature Reviews Drug Discovery 4:988-1004 (2005); Engelman et al., Nature Review Genetics 7:606-619 (2006)). Thus, PI3K hyper-activation is associated with a number of hyper-proliferative, inflammatory, or cardiovascular disorders; including cancer, inflammation, and cardiovascular disease.

There are a number of genetic aberrations that lead to constitutive PI3K signaling; including activating mutations in PI3K itself (Hennessy et al., Nature Reviews Drug Discovery 4:988-1004 (2005); reviewed in Bader et al., Nature Reviews Cancer 5:921-9 (2005)); RAS (reviewed in Downward Nature Reviews Cancer 3:11-22 (2003)) and upstream receptor tyrosine kinases (reviewed in Zwick et al., Trends in Molecular Medicine 8:17-23 (2002)) as well as inactivating mutations in the tumor suppressor PTEN (reviewed in Cully et al., Nature Reviews Cancer 6:184-92 (2006)). Mutations in each of these gene classes have proven to be oncogenic and are commonly found in a variety of cancers.

The molecules defined within this invention inhibit the activity of PI3K, and therefore may be useful for the treatment of proliferative, inflammatory, or cardiovascular disorders. Cases where PI3K pathway mutations have been linked to proliferative disorders where the molecules defined within this invention may have a therapeutic benefit include benign and malignant tumors and cancers from diverse lineage, including but not limited to those derived from colon (Samuels et al., Science 304:554 (2004); reviewed in Karakas et al., British Journal of Cancer 94: 455-59 (2006)), liver (reviewed in Karakas et al., British Journal of Cancer 94: 455-59 (2006)), intestine (reviewed in Hennessy et al., Nature Reviews Drug Discovery 4:988-1004 (2005)), stomach (Samuels et al., Science 304:554 (2004); reviewed in Karakas et al., British Journal of Cancer 94: 455-59 (2006)), esophagus (Phillips et al., International Journal of Cancer 118:2644-6 (2006)); pancreas (reviewed in Downward Nature Reviews Cancer 3:11-22 (2003)); skin (reviewed in Hennessy et al., Nature Reviews Drug Discovery 4:988-1004 (2005)), prostate (reviewed in Hennessy et al., Nature Reviews Drug Discovery 4:988-1004 (2005)), lung (Samuels et al., Science 304:554 (2004); reviewed in Karakas et al., British Journal of Cancer 94: 455-59 (2006)), breast (Samuels et al., Science 304:554 (2004); Isakoff et al., Can Res 65:10992-1000 (2005); reviewed in Karakas et al., British Journal of Cancer 94: 455-59 (2006)), endometrium (Oda et al., Can Res 65:10669-73 (2005); reviewed in Hennessy et al., Nature Reviews Drug Discovery 4:988-1004 (2005)), cervix (reviewed in Hennessy et al., Nature Reviews Drug Discovery 4:988-1004 (2005)); ovary (Shayesteh et al., Nature Genetics 21:99-102 (1999); reviewed in Karakas et al., British Journal of Cancer 94: 455-59 (2006)), testes (Moul et al., Genes Chromosomes Cancer 5:109-18 (1992); Di Vizio et al., Oncogene 24:1882-94 (2005)), hematological cells (reviewed in Karakas et al., British Journal of Cancer 94: 455-59 (2006); Hennessy et al., Nature Reviews Drug Discovery 4:988-1004 (2005)), pancreas (reviewed in Downward Nature Reviews Cancer 3:11-22 (2003)), thyroid (reviewed in Downward Nature Reviews Cancer 3:11-22 (2003); reviewed in Hennessy et al., Nature Reviews Drug Discovery 4:988-1004 (2005)); brain (Samuels et al., Science 304:554 (2004); reviewed in Karakas et al., British Journal of Cancer 94: 455-59 (2006)), bladder (Lopez-Knowles et al., Cancer Research 66:7401-7404 (2006); Hennessy et al., Nature Reviews Drug Discovery 4:988-1004 (2005)); kidney (reviewed in Downward Nature Reviews Cancer 3:11-22 (2003)) and Head and Neck (reviewed in Engelman et al., Nature Reviews Genetics 7:606-619 (2006)).

Other classes of disorders with aberrant PI3K pathway signaling where the molecules defined within this invention may have a therapeutic benefit include inflammatory and cardiovascular diseases, including but not limited to allergies/anaphylaxis (reviewed in Rommel et al., Nature Reviews Immunology 7:191-201 (2007)), acute and chronic inflammation (reviewed in Ruckle et al., Nature Reviews Drug Discovery 5:903-12 (2006); reviewed in Rommel et al., Nature Reviews Immunology 7:191-201 (2007)), rheumatoid arthritis (reviewed in Rommel et al., Nature Reviews Immunology 7:191-201 (2007)); autoimmunity disorders (reviewed in Ruckle et al., Nature Reviews Drug Discovery 5:903-12 (2006)), thrombosis (Jackson et al., Nature Medicine 11:507-14 (2005); reviewed in Ruckle et al., Nature Reviews Drug Discovery 5:903-12 (2006)), hypertension (reviewed in Ruckle et al., Nature Reviews Drug Discovery 5:903-12 (2006)), cardiac hypertrophy (reviewed in Proud et al., Cardiovascular Research 63:403-13 (2004)), and heart failure (reviewed in Mocanu et al., British Journal of Pharmacology 150:833-8 (2007)).

Clearly, it would be beneficial to provi de novel PI3K inhibitors that possess good therapeutic properties, especially for the treatment of proliferative, inflammatory, or cardiovascular disorders.

1. General Description of Compounds of the Invention

This invention provides compounds that are inhibitors of PI3K, and accordingly are useful for the treatment of proliferative, inflammatory, or cardiovascular disorders. The compounds of this invention are represented by formula I:

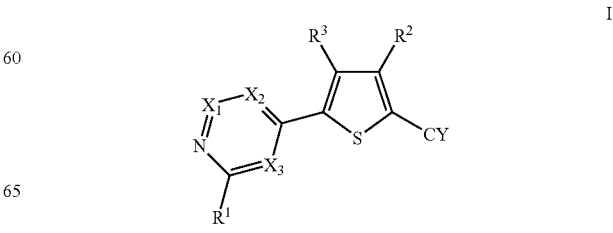

or a pharmaceutically acceptable salt thereof, wherein:

$R^1$ is —$R^{1b}$, —$V_1$—$R^{1c}$, -$T_1$-$R^{1b}$, or —$V_1$-$T_1$-$R^{1b}$ wherein:

$V_1$ is —$NR^{1a}$—, —$NR^{1a}$—C(O)—, —$NR^{1a}$—C(S)—, —$NR^{1a}$—C($NR^{1a}$)—, $NR^{1a}$C(O)O—$NR^{1a}$C(O) $NR^{1a}$—, $NR^{1a}$C(O)S—$NR^{1a}$C(S)O—$NR^{1a}$C(S) $NR^{1a}$—, $NR^{1a}$C(S)S—, —$NR^{1a}$C($NR^{1a}$)O—, —$NR^{1a}$C($NR^{1a}$)$NR^{1a}$—, —$NR^{1a}$S(O)$_2$—, —$NR^{1a}$S (O)$_2$$NR^{1a}$—C(O)—, —$CO_2$—, —C(O)$NR^{1a}$—, C(O) $NR^{1a}$O—, —$SO_2$—, or —$SO_2NR^{1a}$—;

each occurrence of $R^{1a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$T_1$ is an optionally substituted $C_1$-$C_6$ alkylene chain wherein the alkylene chain optionally is interrupted by —N($R^{1a}$)—, —O—, —S—, —S(O)—, —S(O)$_2$—, —C(O)—, —C(O)O—, —C(O)N($R^{1a}$)—, —S(O)$_2$N ($R^{1a}$)—, —OC(O)N($R^{1a}$)—, —N($R^{1a}$)C(O)—, —N($R^{1a}$)SO$_2$—, —N($R^{1a}$)C(O)O—, —N$R^{1a}$C(O)N ($R^{1a}$)—, —N($R^{1a}$)S(O)$_2$N($R^{1a}$)—, —OC(O)—, or —C(O)N($R^{1a}$)—O— or wherein $T_1$ forms part of an optionally substituted 3-7 membered cycloaliphatic or heterocyclyl ring;

each occurrence of $R^{1b}$ is independently hydrogen, halogen, —CN, —NO$_2$, —N($R^{1a}$)$_2$, —O$R^{1a}$, —S$R^{1a}$, —S(O)$_2$$R^{1a}$, —C(O)$R^{1a}$, —C(O)O$R^{1a}$, —C(O)N ($R^{1a}$)$_2$, —S(O)$_2$N($R^{1a}$)$_2$, —OC(O)N($R^{1a}$)$_2$, —N($R^{1a}$)C (O)$R^{1a}$, —N($R^{1a}$)SO$_2$$R^{1a}$, —N($R^{1a}$)C(O)O$R^{1a}$, —N($R^{1a}$)C(O)N($R^{1a}$)$_2$, or —N($R^{1a}$)SO$_2$N($R^{1a}$)$_2$, or an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{1c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or $R^{1a}$ and $R^{1c}$ taken together with a nitrogen atom to which they are bound form an optionally substituted 4-7-membered heterocyclyl ring having 0-1 additional heteroatoms independently selected from nitrogen, oxygen, or sulfur;

$R^2$ is H, halogen, —W—$R^6$, or —$R^6$, wherein:

W is selected from an optionally substituted $C_{1-3}$ alkylene chain, —O—, —N($R^{2a}$)—, —S—, —S(O)—, —S(O)$_2$—, —C(O)—, —$CO_2$—, —C(O)$NR^{2a}$—, —N($R^{2a}$)C(O)—, —N($R^{2a}$)$CO_2$—, —S(O)$_2$$NR^{2a}$—, —N($R^{2a}$)S(O)$_2$—, —OC(O)N($R^{2a}$)—, —N($R^{2a}$)C(O) $NR^{2a}$—, —N$R^{2a}$)S(O)$_2$N($R^{2a}$)—, or —OC(O)—.

$R^{2a}$ is hydrogen or an optionally substituted $C_{1-4}$ aliphatic, and $R^6$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$R^3$ is H, —CN, halogen, —Z—$R^5$, $C_{1-6}$aliphatic, or 3-10-membered cycloaliphatic, wherein:

Z is selected from an optionally substituted $C_{1-3}$ alkylene chain, —O—, —N($R^{3a}$)—, —S—, —S(O)—, —S(O)$_2$—, —C(O)—, —$CO_2$—, —C(O)$NR^{3a}$—, —N($R^{3a}$)C(O)—, —N($R^{3a}$)$CO_2$—, —S(O)$_2$$NR^{3a}$—, —N($R^{3a}$)S(O)$_2$—, —OC(O)N($R^{3a}$)—, —N($R^{3a}$)C(O) $NR^{3a}$—, —N($R^{3a}$)S(O)$_2$N($R^{3a}$)—, or —OC(O)—;

$R^{3a}$ is hydrogen or an optionally substituted $C_{1-4}$ aliphatic, and $R^5$ is an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

CY is 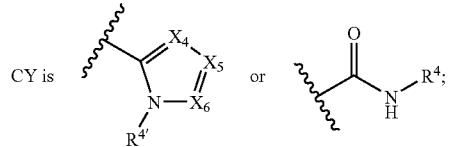

each occurrence of $R^4$ and $R^{4'}$ is H, —Z—$R^6$, $C_{1-6}$ aliphatic, or 3-10-membered cycloaliphatic, wherein:

Z is selected from an optionally substituted $C_{1-3}$ alkylene chain, —O—, —N($R^{4a}$)—, —S(O)—, —S(O)$_2$—, —C(O)—, —$CO_2$—, —C(O)$NR^{4a}$—, —N($R^{4a}$)C (O)—, —N($R^{4a}$)$CO_2$—, —S(O)$_2$$NR^{4a}$—, —N($R^{4a}$)S (O)$_2$—, —OC(O)N($R^{4a}$)—, —N($R^{4a}$)C(O)$NR^{4a}$—, —N($R^{4a}$)S(O)$_2$N($R^{4a}$)—, or —OC(O)—.

$R^{4a}$ is hydrogen or an optionally substituted $C_{1-4}$ aliphatic, and $R^6$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and $X_1$, $X_2$, $X_3$, $X_4$, $X_5$ and $X_6$ are each independently N or $CR^7$, wherein each occurrence of $R^7$ is independently hydrogen, —CN, halogen, —Z—$R^8$, optionally substituted $C_{1-6}$aliphatic, or optionally substituted 3-10-membered cycloaliphatic, wherein:

Z is selected from an optionally substituted $C_{1-3}$ alkylene chain, —O—, —N($R^{7a}$)—, —S—, —S(O)—, —S(O)$_2$—, —C(O)—, —$CO_2$—, —C(O)$NR^{7a}$—, —N($R^{7a}$)C(O)—, —N($R^{7a}$)$CO_2$—, —S(O)$_2$$NR^{7a}$—, —N($R^{7a}$)S(O)$_2$—, —OC(O)N($R^{7a}$)—, —N($R^{7a}$)C(O) $NR^{7a}$—, —N($R^{7a}$)S(O)$_2$N($R^{7a}$)—, or —OC(O)—.

$R^{7a}$ is hydrogen or an optionally substituted $C_{1-4}$ aliphatic, and $R^8$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, provided that:

a) when CY is —CONHR⁴, then R² is an optionally substituted group selected from 6-10-membered aryl, or 5-10-membered heteroaryl having 1-5 heteroatoms independently selected from nitrogen, oxygen, or sulfur; and b) the compound of formula I is other than 4-[5-[3-(2-chloro-6-fluorophenyl)-1-methyl-1H-1,2,4-triazol-5-yl]-4-methyl-2-thienyl]-pyridine, or 4-[5-(2H-tetrazol-5-yl)-2-thienyl]-pyridine.

The present invention also provides compounds of formula I, where:

(a) $R^2$ is an optionally substituted 6-10-membered aryl, or 5-10-membered heteroaryl having 1-5 heteroatoms independently selected from nitrogen, oxygen, or sulfur; or (b) $R^1$ is $-V_1-R^{1c}$.

The present invention also provides compounds of formula I, I-A, I-B, I-C, I-D, I-E, and I-F:

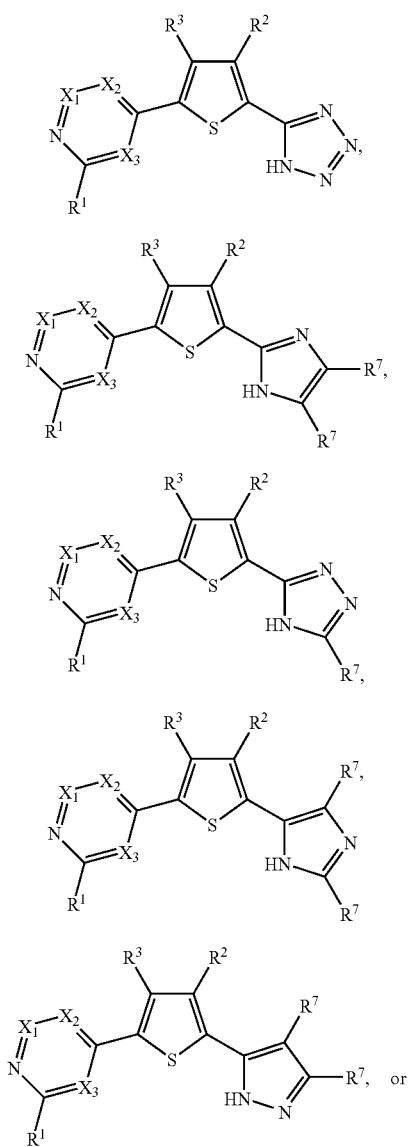

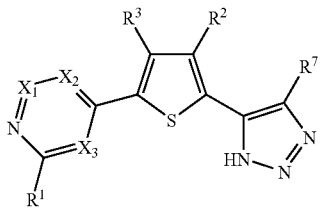

In some embodiments, the invention provides compounds of formula I, I-A, I-B, I-C, I-D, I-E, and I-F wherein $X_2$ is N, and $X_1$ and $X_3$ are each $CR^7$.

In other embodiments, the invention provides compounds of formula I, I-A, I-B, I-C, I-D, I-E, and I-F wherein $X_3$ is N, and $X_1$ and $X_2$ are each $CR^7$.

In other embodiments, the invention provides compounds of formula I, I-A, I-B, I-C, I-D, I-E, and I-F wherein $X_1$, $X_2$ and $X_3$ are each $CR^7$.

In still other embodiments, the invention provides compounds of formula I, I-A, I-B, I-C, I-D, I-E, and I-F wherein $R^2$ is a 3-10-membered cycloaliphatic, 4-10-membered heterocyclyl having 1-5 heteroatoms independently selected from nitrogen, oxygen, or sulfur 6-10-membered aryl, or 5-10-membered heteroaryl having 1-5 heteroatoms independently selected from nitrogen, oxygen, or sulfur, optionally substituted with 1-4 independent occurrences of $R^9$, wherein $R^9$ is $-R^{9a}$, $-T_2-R^{9d}$, or $-V_2-T_2-R^{9d}$, and:

each occurrence of $R^{9a}$ is independently halogen, —CN, —NO₂, —$R^{9e}$, —N($R^{9b}$)₂, —O$R^{9b}$, —S$R^{9c}$, —S(O)₂$R^{9c}$, —C(O)$R^{9b}$, —C(O)O$R^{9b}$, —C(O)N($R^{9b}$)₂, —S(O)₂N($R^{9b}$)₂, —OC(O)N($R^{9b}$)₂, —N($R^{9e}$)C(O)$R^{9b}$, —N($R^{9e}$)SO₂$R^{9e}$, —N($R^{9e}$)C(O)O$R^{9b}$, —N($R^{9e}$)C(O)N($R^{9b}$)₂, or —N($R^{9e}$)SO₂N($R^{9b}$)₂, or two occurrences of $R^{9b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{9b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{9c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{9d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{9e}$ is independently hydrogen or an optionally substituted $C_{1-6}$ aliphatic group;

each occurrence of $V_2$ is independently —N($R^{9e}$)—, —O—, —S—, —S(O)—, —S(O)₂—, —C(O)—, —C(O)O—, —C(O)N($R^{9e}$)—, —S(O)₂N($R^{9e}$)—, —OC(O)N($R^{9e}$)—, —N($R^{9e}$)C(O)—, —N($R^{9e}$)SO₂—, —N(R$^{9e}$)C(O)O—, —NR$^{9e}$C(O)N(R$^{9e}$)—, —N(R$^{9e}$)SO$_2$N(R$^{9e}$)—, —OC(O)—, or —C(O)N(R$^{9e}$)—O—; and T$_2$ is an optionally substituted C$_1$-C$_6$alkylene chain wherein the alkylene chain optionally is interrupted by —N(R$^{7a}$)—, —O—, —S—, —S(O)—, —S(O)$_2$—, —C(O)—, —C(O)O—, —C(O)N(R$^{7a}$)—, —S(O)$_2$N(R$^{7a}$)—, —O—C(O)N(R$^{7a}$)—, —N(R$^{7a}$)C(O)—, —N(R$^{7a}$)SO$_2$—, —N(R$^{7a}$)C(O)O—, —NR$^{7a}$C(O)N(R$^{7a}$)—, —N(R$^{7a}$)S(O)$_2$N(R$^{7a}$)—, —OC(O)—, or —C(O)N(R$^{7a}$)—O— or wherein T$_3$ or a portion thereof optionally forms part of an optionally substituted 3-7 membered cycloaliphatic or heterocyclyl ring.

In other embodiments, the invention provides compounds of formula I, I-A, I-B, I-C, I-D, I-E, and I-F wherein R$^2$ is a phenyl group substituted with 1-3 independent occurrences of halo, C$_{1-3}$alkyl, CN, C$_{1-3}$haloalkyl, —OC$_{1-3}$ alkyl, —OC$_{1-3}$haloalkyl, —NHC(O)C$_{1-3}$ alkyl, —NHC(O)NHC$_{1-3}$alkyl, NHS(O)$_2$C$_{1-3}$alkyl, or —C(O)H.

The present invention also provides compounds of formula II:

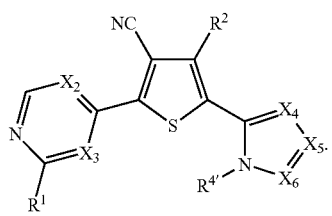

II

In some embodiments, for compounds of formula II:
R$^1$ is —V$_1$—R$^{1c}$, where V$_1$ is —NR$^{1a}$CO—, or —N(R$^{1a}$)$_2$; and
R$^2$ is a phenyl group substituted with 1-3 independent occurrences of halo, C$_{1-3}$ alkyl, —CN, C$_{1-3}$haloalkyl, —OC$_{1-3}$ alkyl, —OC$_{1-3}$haloalkyl, —NHC(O)C$_{1-3}$alkyl, —NHC(O)NHC$_{1-3}$ alkyl, NHS(O)$_2$C$_{1-3}$alkyl, or —C(O)H.

In other embodiments, for compounds of formula II X$_4$ is N, and X$_5$ and X$_6$ are each CR$^7$. In still other embodiments, X$_4$ is N, X$_5$ is N, and X$_6$ is CR$^7$.

The present invention also provides compounds of formula III:

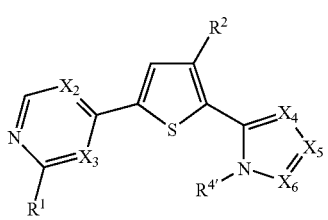

III

The present invention also provides compounds of formula III wherein:
R$^1$ is —V$_1$—R$^{1c}$, where V$_1$ is —NR$^{1a}$CO—, or —N(R$^{1a}$)$_2$; and
R$^2$ is a phenyl group substituted with 1-3 independent occurrences of halo, C$_{1-3}$ alkyl, —CN, C$_{1-3}$haloalkyl, —OC$_{1-3}$ alkyl, —OC$_{1-3}$ haloalkyl, —NHC(O)C$_{1-3}$ alkyl, —NHC(O)NHC$_{1-3}$ alkyl, NHS(O)$_2$C$_{1-3}$ alkyl, or —C(O)H.

The present invention also provides compounds of formula III wherein X$_4$ is N, and X$_5$ and X$_6$ are each CR$^7$. In other embodiments, X$_4$ is N, X$_5$ is N, and X$_6$ is CR$^7$.

The present invention also provides a composition comprising a compound of formula I, I-A, I-B, I-C, I-D, I-E, I-F, II, or III and a pharmaceutically acceptable carrier.

The present invention also provides a method of treating a proliferative disorder in a patient comprising administering to said patient a therapeutically effective amount of a compound of formula I, I-A, I-B, I-C, I-D, I-E, I-F, II, or III. In some embodiments, the proliferative disorder is breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, or ovarian cancer.

The present invention also provides a method of treating an inflammatory or cardiovascular disorder in a patient comprising administering to said patient a therapeutically effective amount of a compound of formula I, I-A, I-B, I-C, I-D, I-E, I-F, II, or III. In some embodiments, the inflammatory or cardiovascular disorder is selected from allergies/anaphylaxis, acute and chronic inflammation, rheumatoid arthritis; autoimmunity disorders, thrombosis, hypertension, cardiac hypertrophy, and heart failure.

The present invention also provides a method for inhibiting PI3K activity in a patient comprising administering a composition comprising an amount of a compound of formula I, I-A, I-B, I-C, I-D, I-E, I-F, II, or III effective to inhibit PI3K activity in the patient.

DETAILED DESCRIPTION OF THE INVENTION

2. Compounds and Definitions

Compounds of this invention include those described generally for formula I above, and are further illustrated by the classes, subclasses, and species disclosed herein. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40°, in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, "a 3-7-membered saturated, partially unsaturated, or aromatic monocyclic ring having 0-3 heteroatoms independently selected from nitrogen, oxygen, or sulfur, or an 8-10-membered partially unsaturated, or aromatic bicyclic ring system having 0-5 heteroatoms independently selected from nitrogen, oxygen, or sulfur" includes cycloaliphatic, heterocyclic, aryl and heteroaryl rings.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle", "cycloaliphatic", "cycloalkyl", or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-10, 3-8, 3-7, or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1, 2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$aromatic hydrocarbon moiety comprising one to three aromatic rings. Preferably, the aryl group is a $C_{6-10}$aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl$C_{1-6}$alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5 to 10, more preferably 5, 6, 9, or 10 ring atoms; having 6, 10, or 14π electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic. The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a 3- to 10-, preferably 3- to 7-, 4- to 7- or 4- to 10-membered heterocycle such as a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings:

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroaralkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, —NO$_2$, —CN, —R$^+$, —C(R$^+$)=C(R$^+$)$_2$, —C≡C—R$^+$, —OR$^+$, —SR$^o$, —S(O)R$^o$, —SO$_2$R$^o$, —SO$_3$R$^+$, —SO$_2$N(R$^+$)$_2$, —N(R$^+$)$_2$, —NR$^+$C(O)R$^+$, —NR$^+$C(S)R$^+$, —NR$^+$C(O)N(R$^+$)$_2$, —NR$^+$C(S)N(R$^+$)$_2$, —N(R$^+$)C(=NR$^+$)—N(R$^+$)$_2$, —N(R$^+$) C(=NR$^+$)—R$^o$, —NR$^+$CO$_2$R$^+$, —NR$^+$SO$_2$R$^o$, —NR$^+$SO$_2$N(R$^+$)$_2$, —O—C(O)R$^+$, —O—CO$_2$R$^+$, —OC(O)N(R$^+$)$_2$, —C(O)R$^+$, —C(S)R$^o$, —CO$_2$R$^+$, —C(O)—C(O)R$^+$, —C(O)N(R$^+$)$_2$, —C(S)N(R$^+$)$_2$, —C(O)N(R$^+$)—OR$^+$, —C(O)N(R$^+$)C(=NR$^+$)—N(R$^+$)$_2$, —N(R$^+$)C(=NR$^+$)—N(R$^+$)—C(O)R$^+$, —C(=NR$^+$)—N(R$^+$)$_2$, —C(=NR$^+$)—OR$^+$, —N(R$^+$)—N(R$^+$)$_2$, —C(=NR$^+$)—N(R$^+$)—OR$^+$, —C(R$^o$)=N—OR$^+$, —P(O)(R$^+$)$_2$, —P(O)(OR$^+$)$_2$, —O—P(O)—OR$^+$, and —P(O)(NR$^+$)—N(R$^+$)$_2$, wherein R$^+$, independently, is hydrogen or an optionally substituted aliphatic, aryl, heteroaryl, cycloaliphatic, or heterocyclyl group, or two independent occurrences of R$^+$ are taken together with their intervening atom(s) to form an optionally substituted 5-7-membered aryl, heteroaryl, cycloaliphatic, or heterocyclyl ring. Each R$^o$ is an optionally substituted aliphatic, aryl, heteroaryl, cycloaliphatic, or heterocyclyl group.

An aliphatic or heteroaliphatic group, or a non-aromatic carbycyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)$_2$, =N—N(R*)$_2$, =N—OR*, =N—NHC(O)R*, =N—NHCO$_2$R$^o$=N—NHSO$_2$R$^o$ or =N—R* where R$^o$ is defined above, and each R* is independently selected from hydrogen or an optionally substituted C$_{1-6}$ aliphatic group.

In addition to the substituents defined above and herein, optional substituents on the nitrogen of a non-aromatic heterocyclic ring also include and are generally selected from —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(S)N(R$^+$)$_2$, —C(=NH)—N(R$^+$)$_2$, or —N(R$^+$)S(O)$_2$R$^+$; wherein each R$^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R$^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R$^+$ (or any other variable similarly defined in the specification and claims herein), are taken together with their intervening atom(s) include, but are not limited to the following: a) two independent occurrences of R$^+$ (or any other variable similarly defined in the specification or claims herein) that are bound to the same atom and are taken together with that atom to form a ring, for example, $N(R^+)_2$, where both occurrences of $R^+$ are taken together with the nitrogen atom to form a piperidin-1-yl, piperazin-1-yl, or morpholin-4-yl group; and b) two independent occurrences of $R^+$ (or any other variable similarly defined in the specification or claims herein) that are bound to different atoms and are taken together with both of those atoms to form a ring, for example where a phenyl group is substituted with two occurrences of $OR^+$

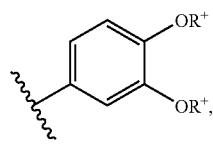

these two occurrences of $R^+$ are taken together with the oxygen atoms to which they are bound to form a fused 6-membered oxygen containing ring:

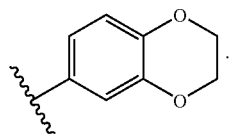 [SMILES: *c1ccc2c(c1)OCCO2]

It will be appreciated that a variety of other rings (e.g., spiro and bridged rings) can be formed when two independent occurrences of $R^+$ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

It is to be understood that, when a disclosed compound has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer free of other diastereomers, a pair of diastereomers free from other diastereomeric pairs, mixtures of diasteromers, mixtures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds

In certain embodiments, for compounds of general formula I, one or more substituents are selected from:

(a) $R^2$ is an optionally substituted 6-10-membered aryl, or 5-10-membered heteroaryl having 1-5 heteroatoms independently selected from nitrogen, oxygen, or sulfur; or (b) $R^1$ is $-V_1-R^{1c}$.

In other embodiments, for compounds of general formula I, compounds are represented by:

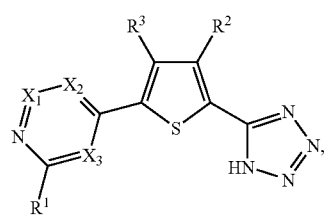

I-A

-continued

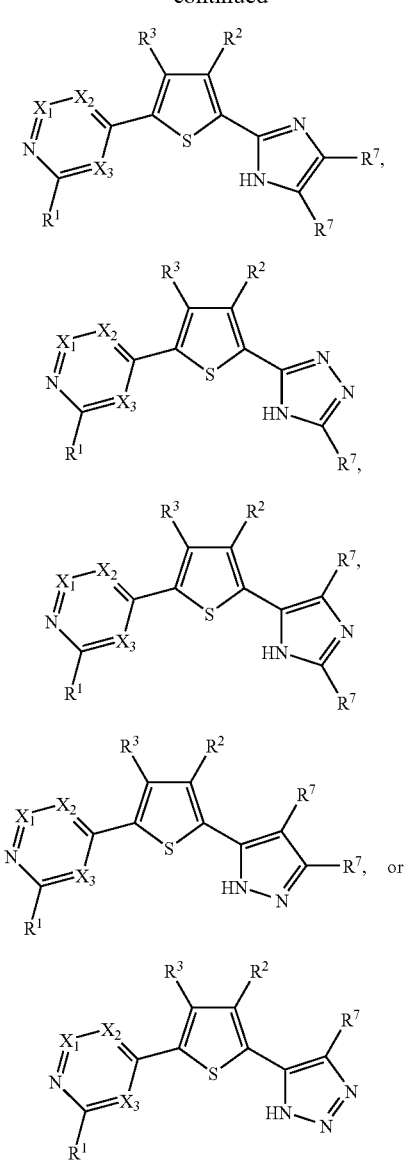

In still other embodiments, for compounds of general formulas I, I-A, I-B, I-C, I-D, I-E, or I-F, $X_2$ is N, and $X_1$ and $X_3$ are each $CR^7$. In yet other embodiments, $X_3$ is N, and $X_1$ and $X_2$ are each $CR^7$. In still other embodiments, $X_1$, $X_2$ and $X_3$ are each $CR^7$. In further embodiments, $R^7$ is hydrogen, halogen or a $C_{1-6}$ alkyl group.

In other embodiments, for compounds of general formula I, I-A, I-B, I-C, I-D, I-E, or I-F, $R^1$ is $-V_1-R^{1c}$ or $-V_1-T_1-R^{1b}$ wherein:

$V_1$ is $-NR^{1a}$, $-NR^{1a}-C(O)-$, $-NR^{1a}-C(NR^{1a})-$, $NR^{1a}C(O)O-$, or $-NR^{1a}S(O)_2-$;

each occurrence of $R^{1a}$ is independently hydrogen, $C_{1-6}$alkyl group, or 3-10-membered cycloalkyl group;

$T_1$ is $C_1-C_6$alkylene chain wherein the alkylene chain optionally is interrupted by $-N(R^{1a})-$, or $-O-$;

each occurrence of $R^{1b}$ is independently hydrogen, halogen, $-N(R^{1a})_2$, $-N(R^{1a})C(O)R^{1a}$;

each occurrence of $R^{1c}$ is independently hydrogen, a $C_{1-6}$ alkyl group optionally substituted by halogen or hydroxyl, or a 6-10-membered aryl group optionally substituted by $C_{1-6}$ alkyl or $C_{1-6}$ alkyloxy.

In other embodiments, for compounds of general formula I, I-A, I-B, I-C, I-D, I-E, or I-F, $R^2$ is a 3-10-membered cycloaliphatic, 4-10-membered heterocyclyl having 1-5 heteroatoms independently selected from nitrogen, oxygen, or sulfur 6-10-membered aryl, or 5-10-membered heteroaryl having 1-5 heteroatoms independently selected from nitrogen, oxygen, or sulfur, optionally substituted with 1-4 independent occurrences of $R^9$, wherein $R^9$ is $-R^{9a}$, $-T_2-R^{9d}$, or $-V_2-T_2-R^{9d}$, and:

each occurrence of $R^{9a}$ is independently halogen, $-CN$, $-NO_2$, $-R^{9c}$, $-N(R^{9b})_2$, $-OR^{9b}$, $-SR^{9c}$, $-S(O)_2R^{9c}$, $-C(O)R^{9b}$, $-C(O)OR^{9b}$, $-C(O)N(R^{9b})_2$, $-S(O)_2N(R^{9b})_2$, $-OC(O)N(R^{9b})_2$, $-N(R^{9e})C(O)R^{9b}$, $-N(R^{9e})SO_2R^{9c}$, $-N(R^{9e})C(O)OR^{9b}$, $-N(R^{9e})C(O)N(R^{9b})_2$, or $-N(R^{9e})SO_2N(R^{9b})_2$, or two occurrences of $R^{9b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{9b}$ is independently hydrogen or an optionally substituted group selected from $C_1$-$C_6$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{9c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{9d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{9e}$ is independently hydrogen or an optionally substituted $C_{1-6}$ aliphatic group;

each occurrence of $V_2$ is independently $-N(R^{9e})-$, $-S-$, $-S(O)-$, $-S(O)_2-$, $-C(O)-$, $-C(O)O-$, $-C(O)N(R^{9e})-$, $-S(O)_2N(R^{9e})-$, $-OC(O)N(R^{9e})-$, $-N(R^{9e})C(O)-$, $-N(R^{9e})SO_2-$, $-N(R^{9e})C(O)O-$, $-NR^{9e}C(O)N(R^{9e})-$, $-N(R^{9e})SO_2N(R^{9e})-$, $-OC(O)-$, or $-C(O)N(R^{9e})-O-$; and $T_2$ is an optionally substituted $C_1$-$C_6$alkylene chain wherein the alkylene chain optionally is interrupted by $-N(R^{7a})-$, $-O-$, $-S-$, $-S(O)-$, $-S(O)_2-$, $-C(O)-$, $-C(O)O-$, $-C(O)N(R^{7a})-$, $-S(O)_2N(R^{7a})-$, $-OC(O)N(R^{7a})-$, $-N(R^{7a})C(O)-$, $-N(R^{7a})SO_2-$, $-N(R^{7a})C(O)O-$, $-NR^{7a}C(O)N(R^{7a})-$, $-N(R^{7a})S(O)_2N(R^{7a})-$, $-OC(O)-$, or $-C(O)N(R^{7a})-O-$ or wherein $T_3$ or a portion thereof optionally forms part of an optionally substituted 3-7 membered cycloaliphatic or heterocyclyl ring.

In still other embodiments for compounds of general formula I, I-A, I-B, I-C, I-D, I-E, or I-F, $R^2$ is a phenyl group substituted with 1-3 independent occurrences of halo, $C_{1-3}$ alkyl, CN, $C_{1-3}$haloalkyl, $-OC_{1-3}$ alkyl, $-OC_{1-3}$haloalkyl, $-NHC(O)C_{1-3}$ alkyl, $-NHC(O)NHC_{1-3}$ alkyl, NHS$(O)_2C_{1-3}$ alkyl, or $-C(O)H$. In further other embodiments for compounds of general formula I, $R^2$ is a phenyl group substituted with 1-3 independent occurrences of halo.

In yet other embodiments, for compounds of general formula I, I-A, I-B, I-C, I-D, I-E, or I-F, and subsets thereof, $R^3$ is H or CN.

In other embodiments, for compounds of general formula I, I-A, I-B, I-C, I-D, I-E, or I-F, $R^{4'}$ is H, or —Z—$R^6$, wherein:

Z is $C_{1-3}$ alkylene chain, and $R^6$ is a 6-10-membered aryl group.

In other embodiments, for compounds of general formula I, I-A, I-B, I-C, I-D, I-E, or I-F, $R^7$ is independently hydrogen, halogen, a $C_{1-6}$ alkyl group, or —Z—$R^8$, wherein:

Z is selected from $C_{1-3}$ alkylene chain, or —$CO_2$—, and $R^8$ is a $C_{1-6}$ alkyl group, a 4-10-membered heterocyclyl group having 1-5 heteroatoms independently selected from nitrogen, oxygen, or sulfur, or a 6-10-membered aryl group each of which is optionally substituted by halogen.

In other embodiments, the compound has the structure of formula II:

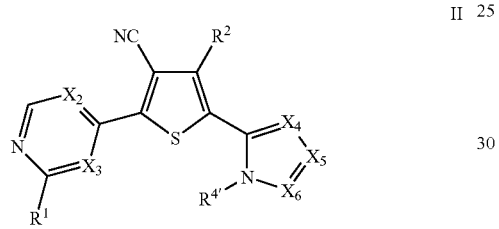

II

In some embodiments, for compounds of formula I, I-A, I-B, I-C, I-D, I-E, I-F or II:

$R^1$ is —$V_1$—$R^{1c}$, where $V_1$ is —$NR^{1a}CO$—, or —$N(R^{1a})_2$; and $R^2$ is a phenyl group substituted with 1-3 independent occurrences of halo, $C_{1-3}$ alkyl, —CN, $C_{1-3}$haloalkyl, —$OC_{1-3}$ alkyl, —$OC_{1-3}$haloalkyl, —NHC(O)$C_{1-3}$ alkyl, —NHC(O)NHC$_{1-3}$ alkyl, NHS(O)$_2C_{1-3}$alkyl, or —C(O)H.

Preferred $R^{1a}$ is independently hydrogen, a $C_{1-6}$alkyl group, or a 3-10-membered cycloalkyl group, and $R^{1c}$ is independently hydrogen, a $C_{1-6}$ alkyl group optionally substituted by halogen or hydroxyl, or a 6-10-membered aryl group optionally substituted by $C_{1-6}$ alkyl or $C_{1-6}$alkyloxy.

Preferred $R^2$ is a phenyl group optionally substituted with 1-3 independent occurrences of halo.

In some embodiments for compounds of formula I, I-A, I-B, I-C, I-D, I-E, I-F or II, $X_4$ is N and $X_5$ and $X_6$ are each $CR^7$.

In other embodiments, for compounds of formula I, I-A, I-B, I-C, I-D, I-E, I-F or II, $X_4$ is N, $X_5$ is N, and $X_6$ is $CR^7$.

In other embodiments, for compounds of formula I, I-A, I-B, I-C, I-D, I-E, I-F or II, $R^7$ is hydrogen, halogen or a $C_{1-6}$ alkyl group.

In other embodiments, for compounds of formula I, I-A, I-B, I-C, I-D, I-E, I-F or II, any combination of preferable group of each symbol mentioned above is used.

Table 1 below depicts certain compounds represented by compounds of general formula I.

TABLE 1

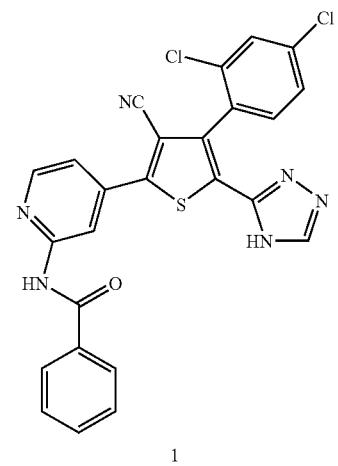

1

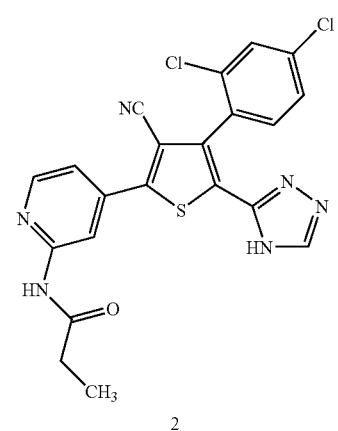

2

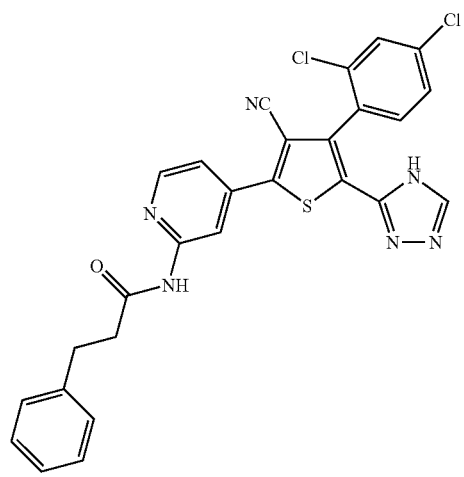

3

TABLE 1-continued
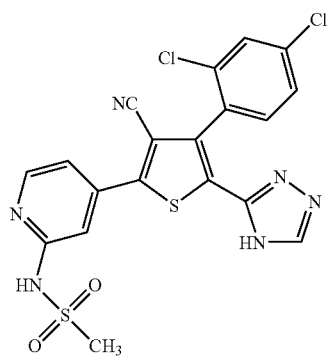
4
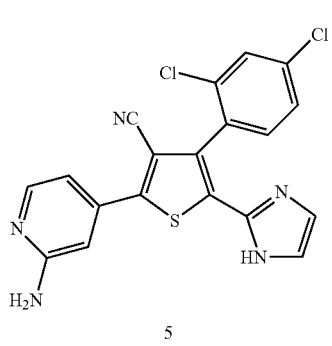
5
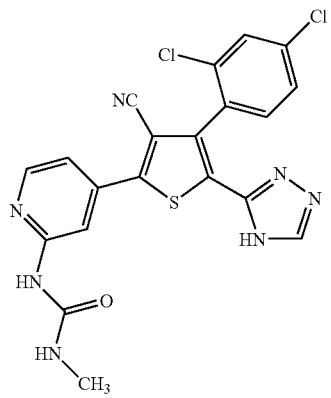
6
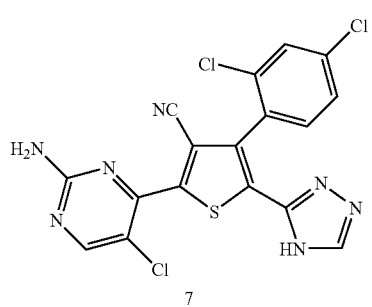
7
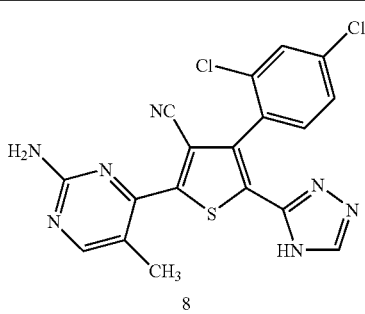
8
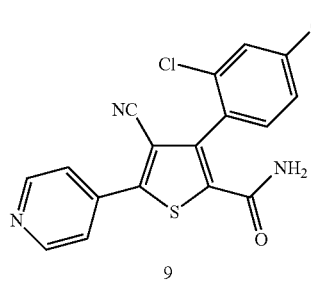
9
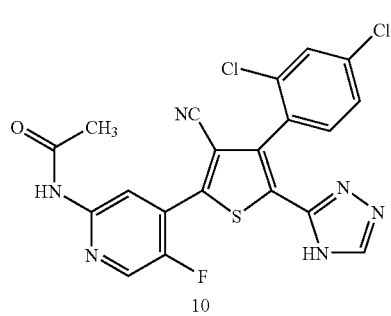
10
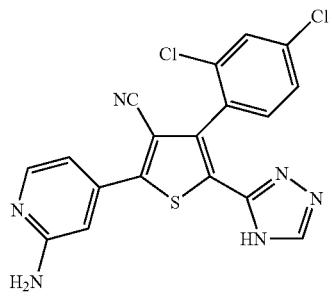
11
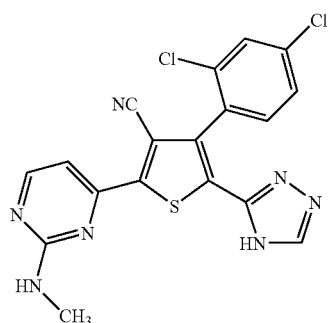
12

TABLE 1-continued
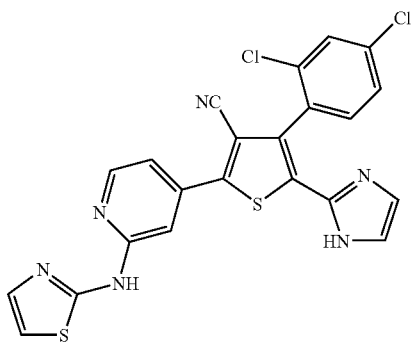
13
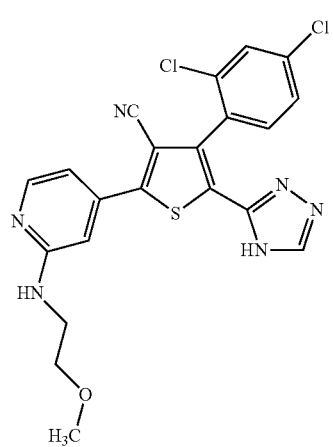
14
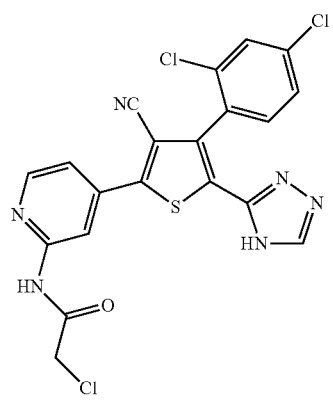
15
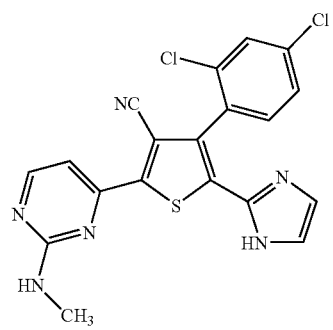
16
TABLE 1-continued
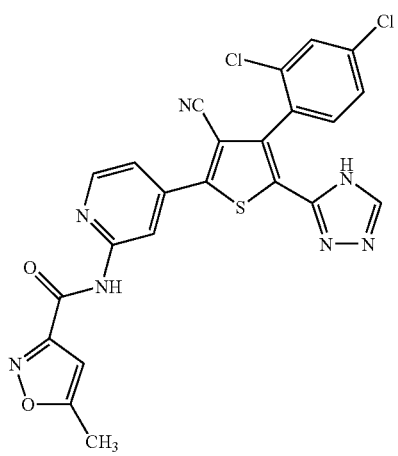
17
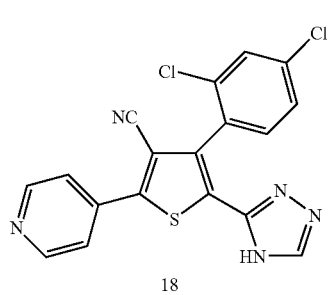
18
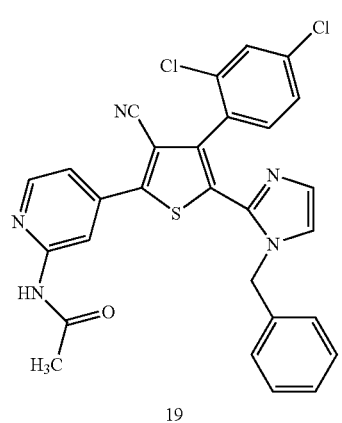
19
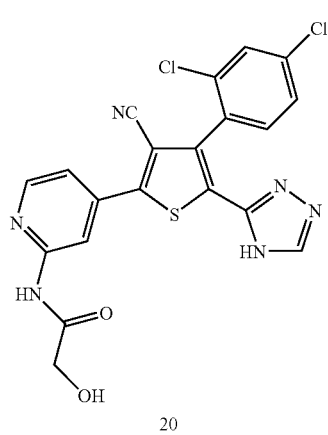
20

TABLE 1-continued
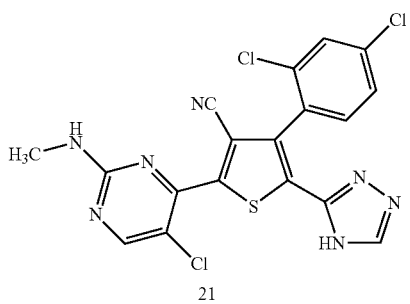
21
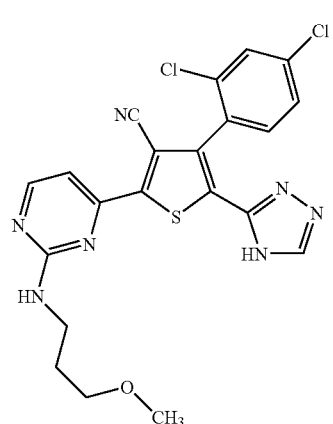
22
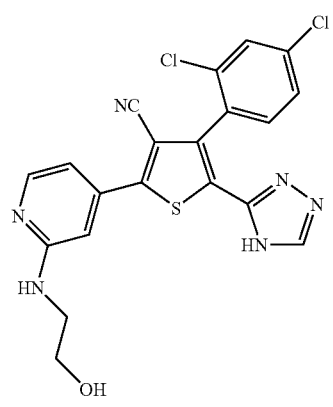
23
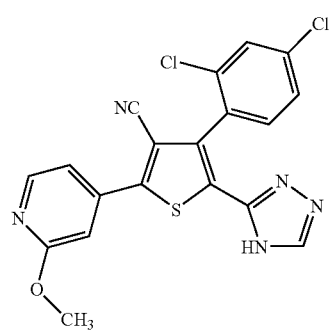
24
TABLE 1-continued
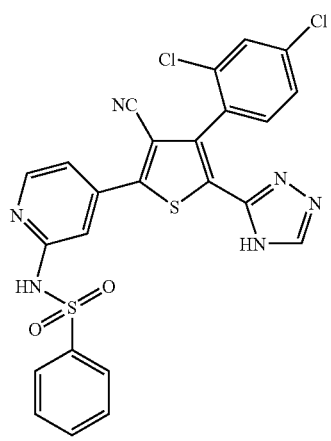
25
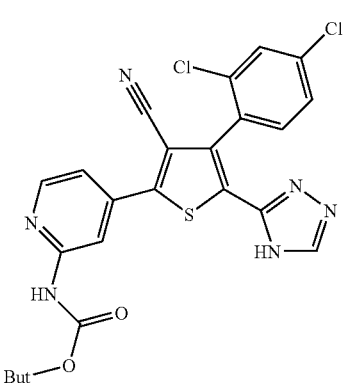
26
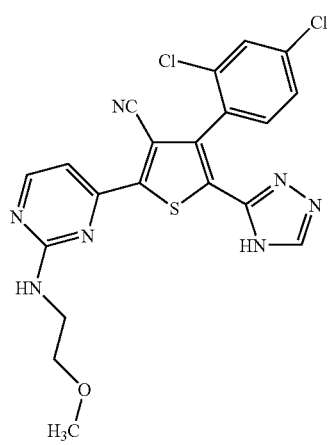
27

TABLE 1-continued
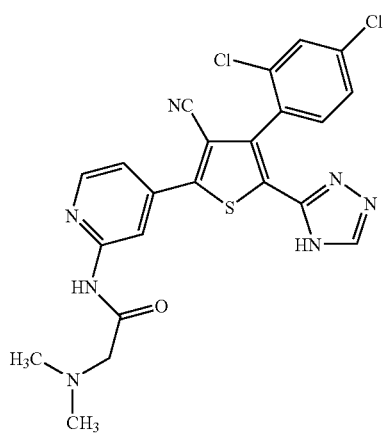
28
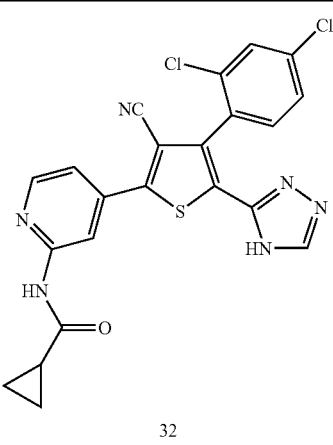
32
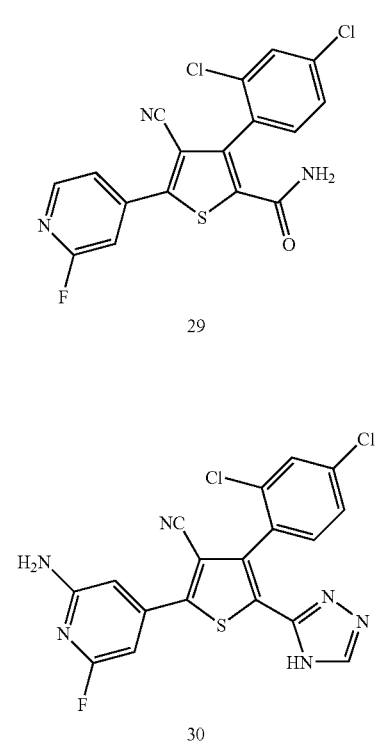
29
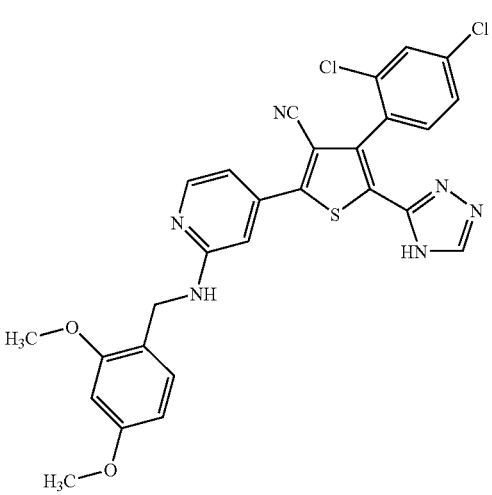
33
30
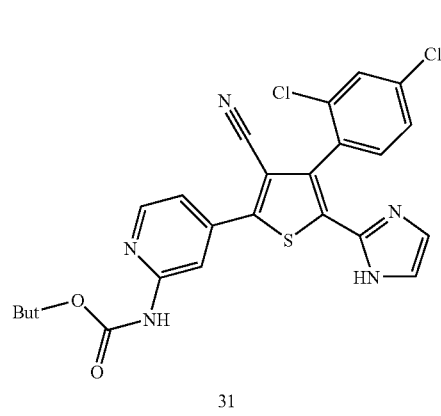
31
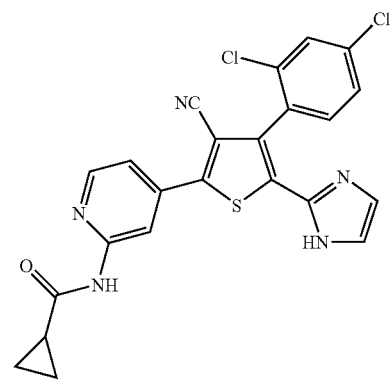
34

TABLE 1-continued
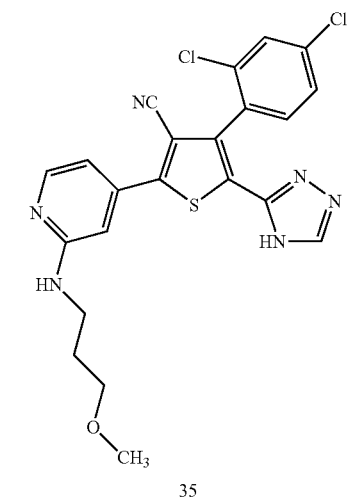
35
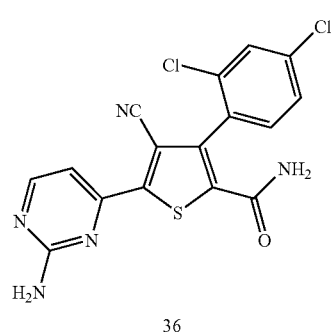
36
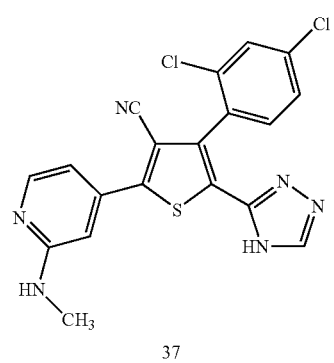
37
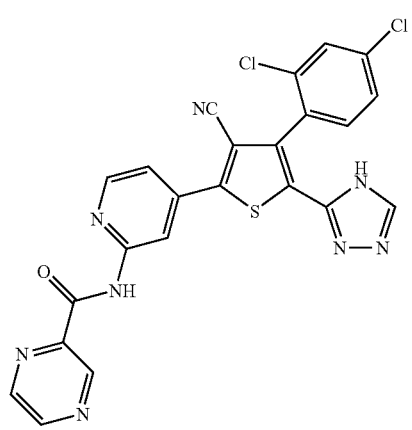
38
TABLE 1-continued
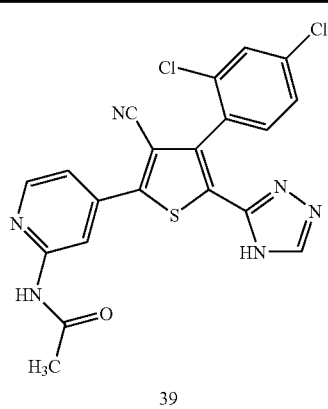
39
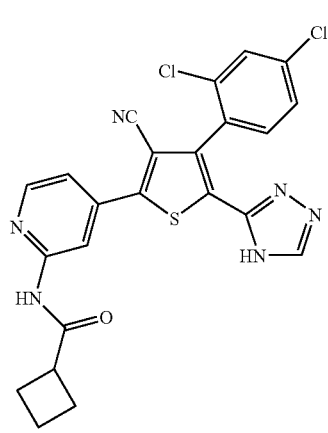
40
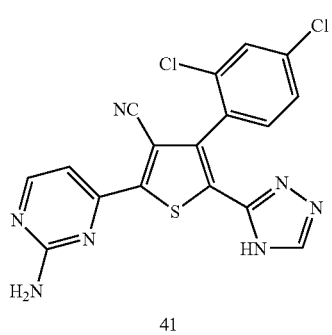
41
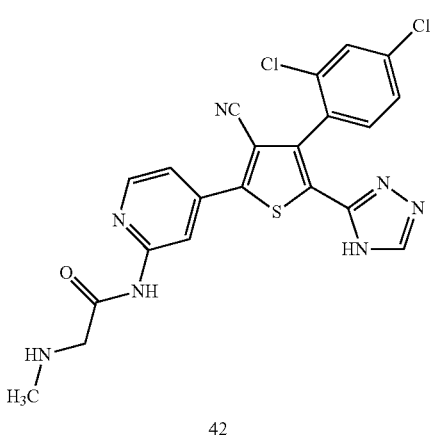 [SMILES: CNCC(=O)Nc1cc(-c2sc(-c3nnc[nH]3)c(-c3ccc(Cl)cc3Cl)c2C#N)ccn1]
42

TABLE 1-continued
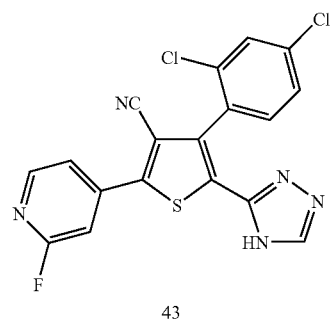
43
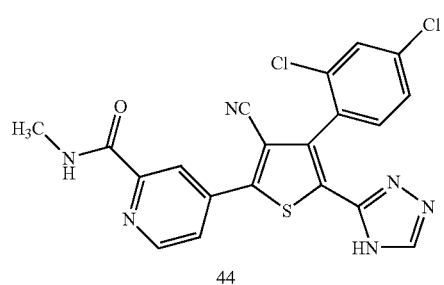
44
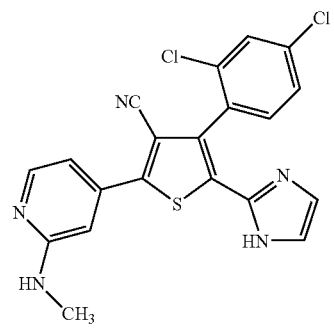
45
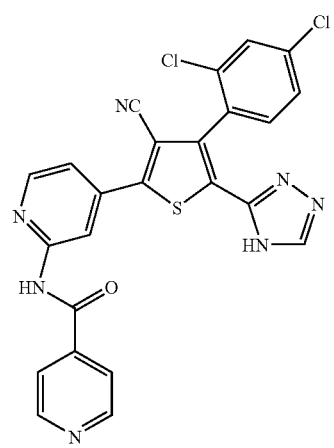
46
TABLE 1-continued
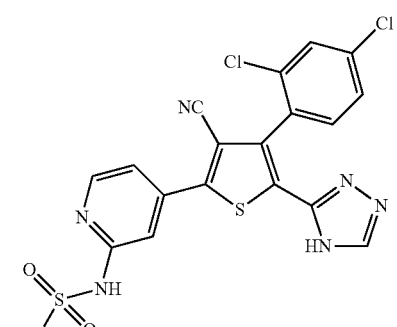
47
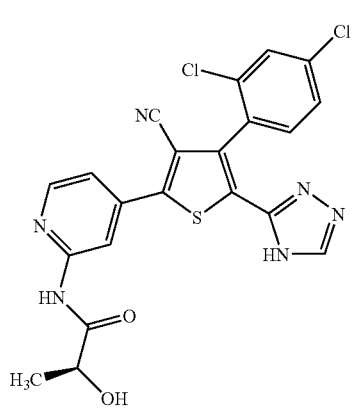
48
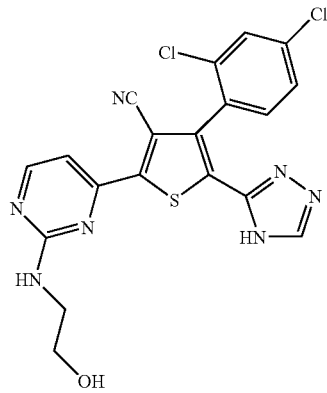
49

TABLE 1-continued
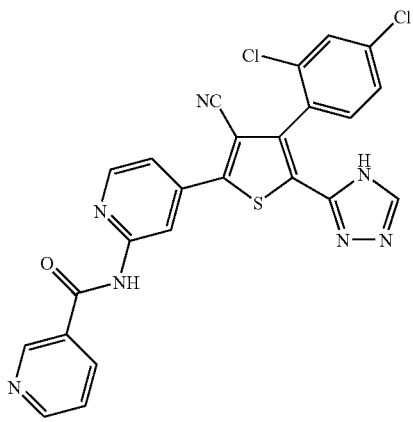
50
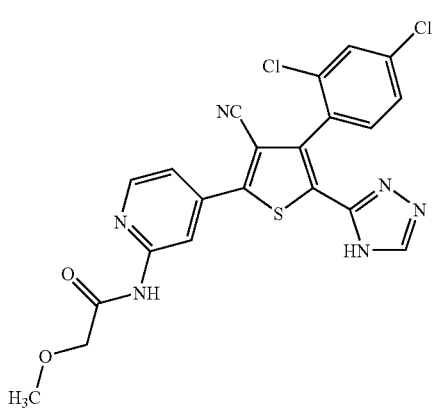
51
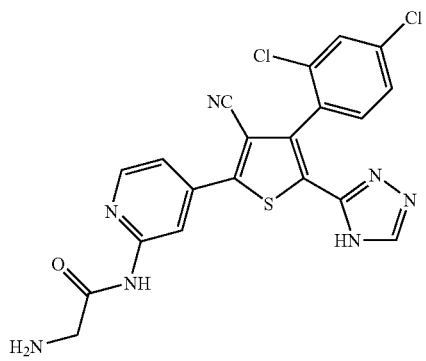
52
TABLE 1-continued
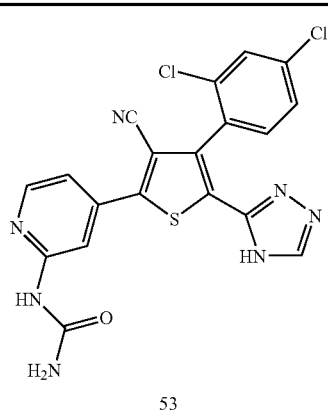
53
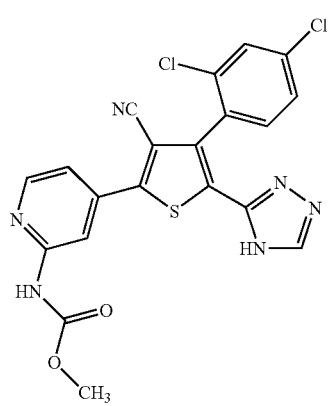
54
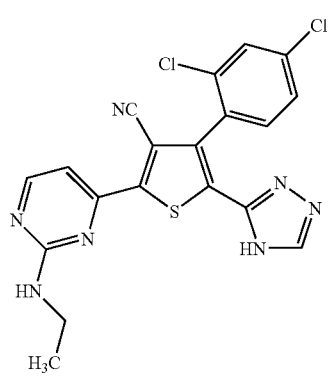
55
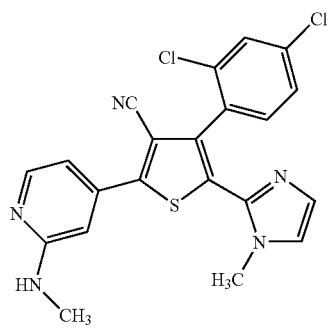
56

TABLE 1-continued
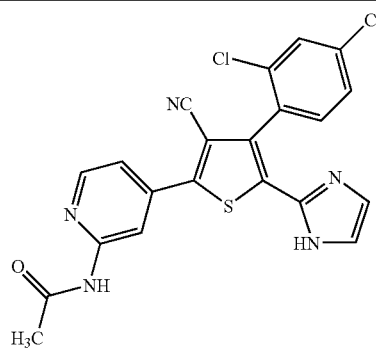
57
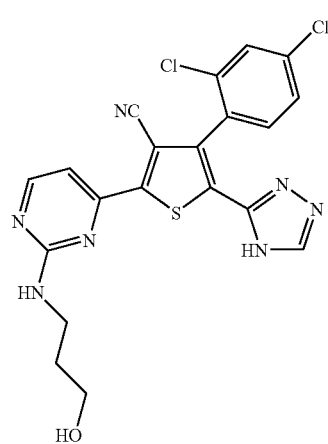
58
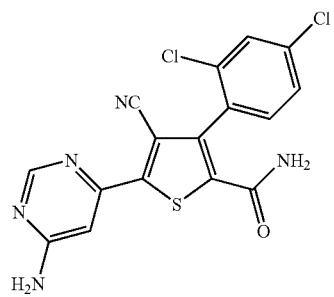
59
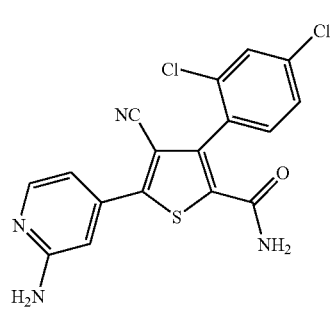
60
TABLE 1-continued
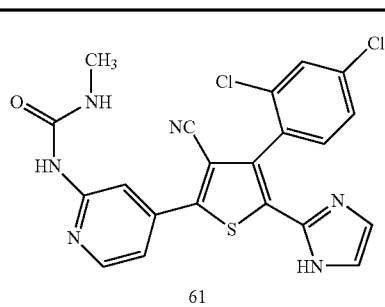
61
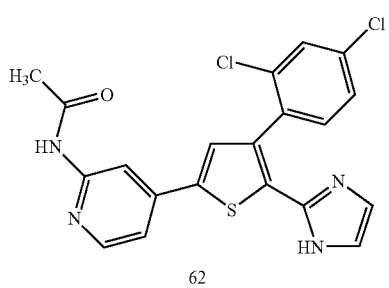 [SMILES: CC(=O)Nc1cc(-c2cc(-c3ccc(Cl)cc3Cl)c(-c3ncc[nH]3)s2)ccn1]
62
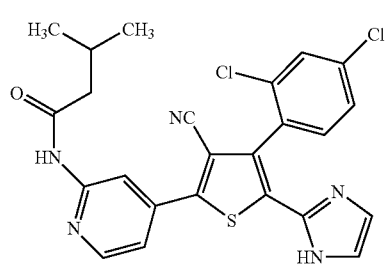
63
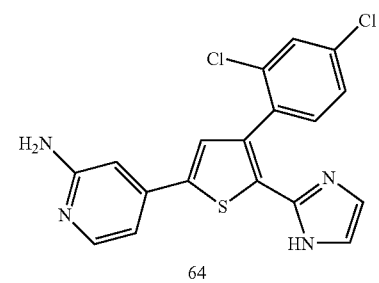 [SMILES: Nc1cc(-c2cc(-c3ccc(Cl)cc3Cl)c(-c3ncc[nH]3)s2)ccn1]
64
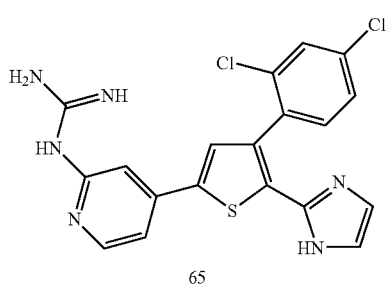
65

TABLE 1-continued
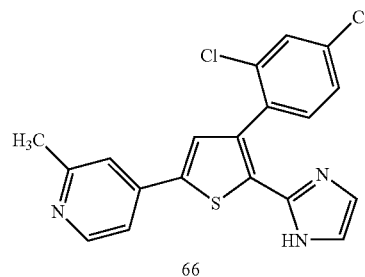
66
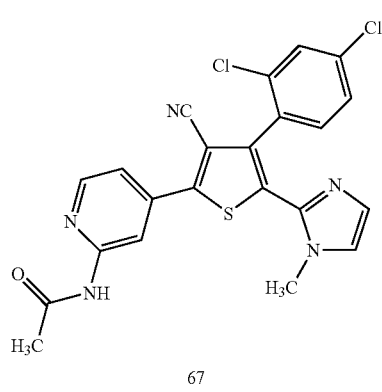
67
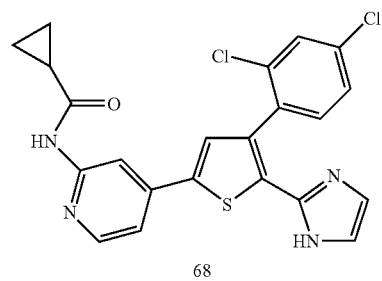 [SMILES: O=C(Nc1cc(-c2cc(-c3ccc(Cl)cc3Cl)c(-c3ncc[nH]3)s2)ccn1)C1CC1]
68
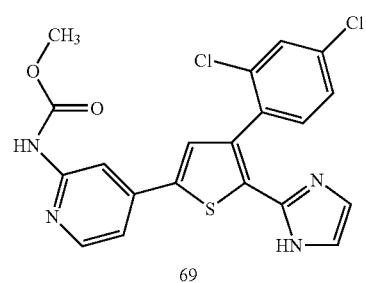 [SMILES: COC(=O)Nc1cc(-c2cc(-c3ccc(Cl)cc3Cl)c(-c3ncc[nH]3)s2)ccn1]
69
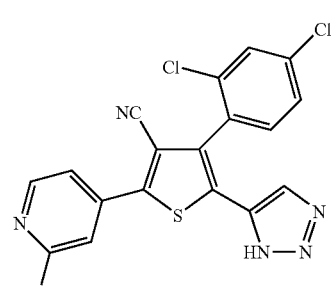
70
TABLE 1-continued
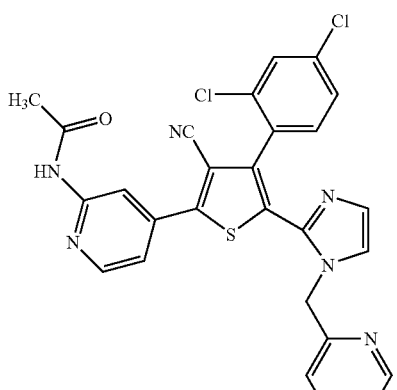
71
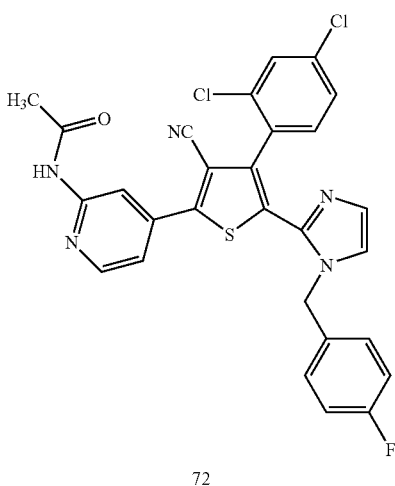
72
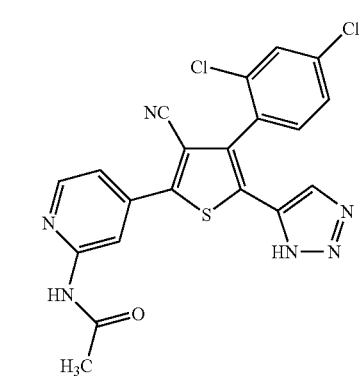
73
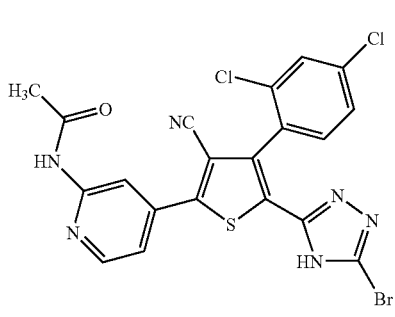
74

TABLE 1-continued
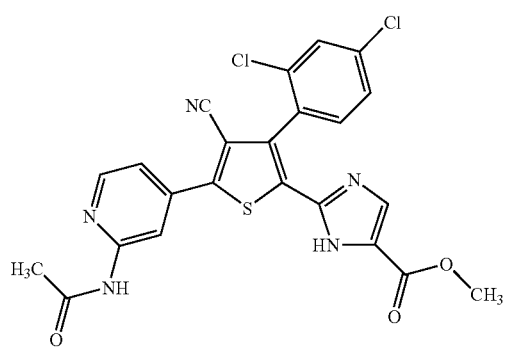
75
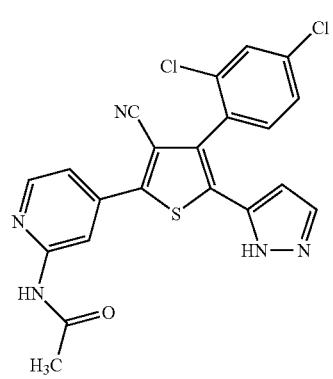
76
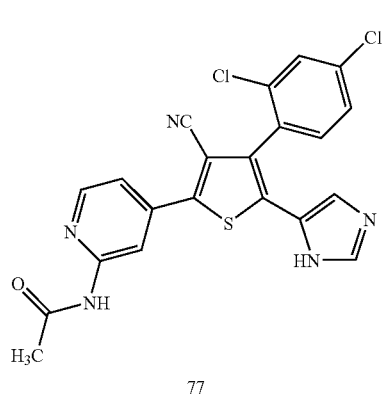
77
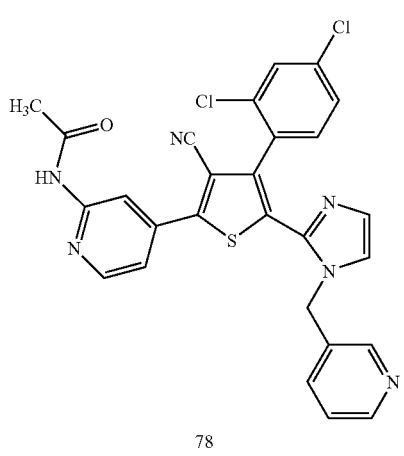
78
TABLE 1-continued
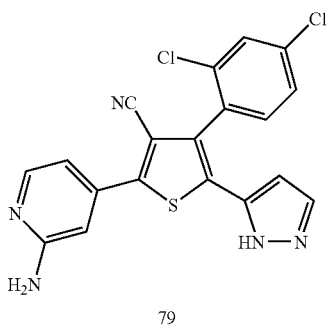
79
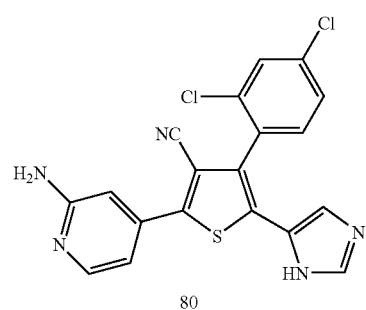
80
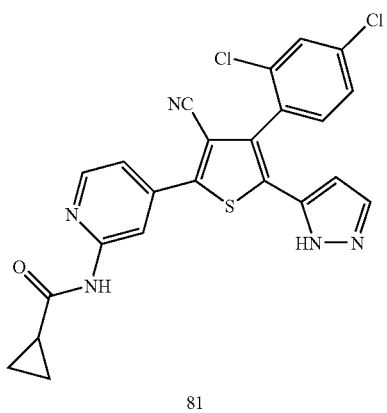
81
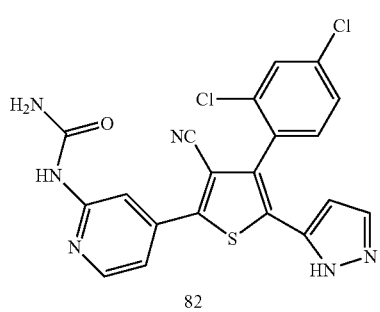
82
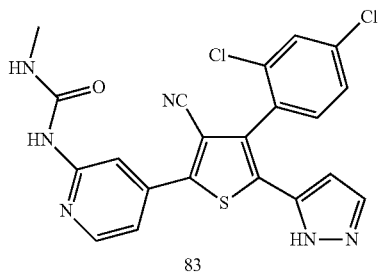 [SMILES: CNC(=O)Nc1cc(-c2sc(-c3ccn[nH]3)c(-c3ccc(Cl)cc3Cl)c2C#N)ccn1]
83

TABLE 1-continued

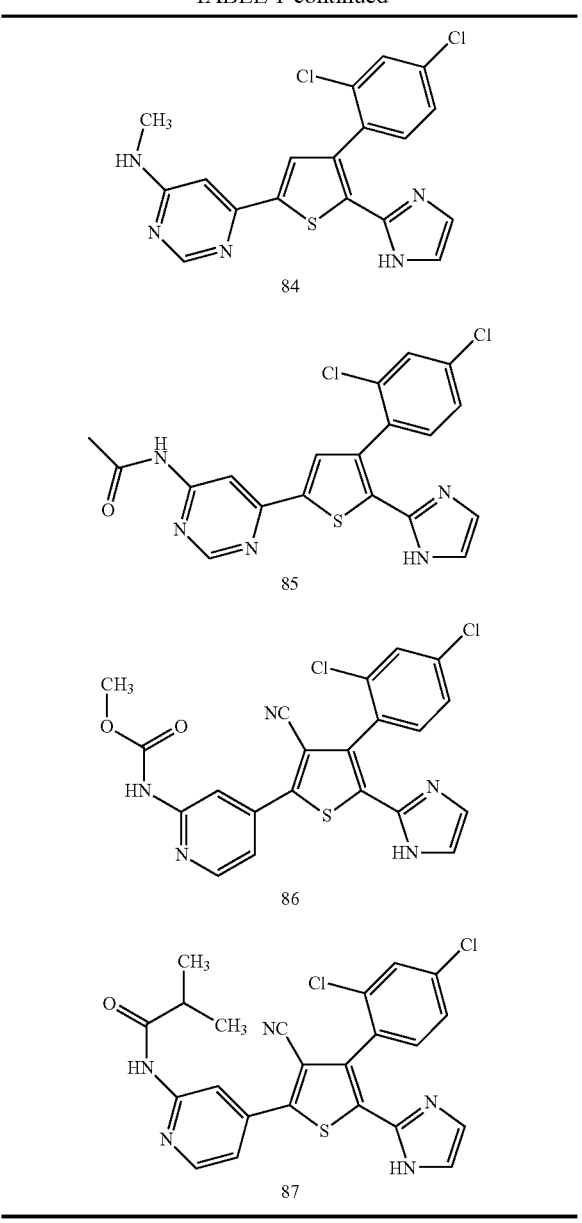

84

85

86

87

4 General Synthetic Methods and Intermediates

The compounds of the present invention can be prepared by methods known to one of ordinary skill in the art and/or by reference to the schemes shown below and the synthetic examples that follow. Exemplary synthetic routes are set forth in Schemes 1-14 below, and in the Examples.

Scheme 1: Synthesis of 3-substituted 4-cyano-5-pyridine-4-ylthiophene-2-triazoles

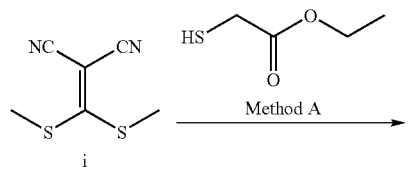

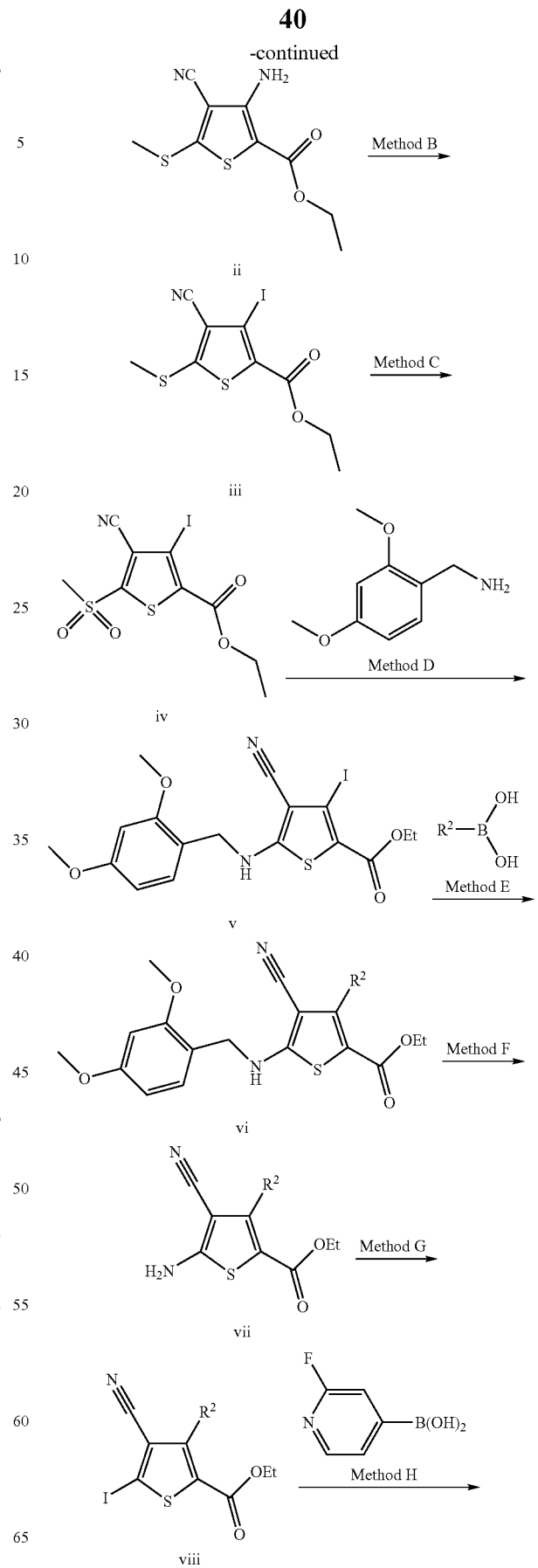

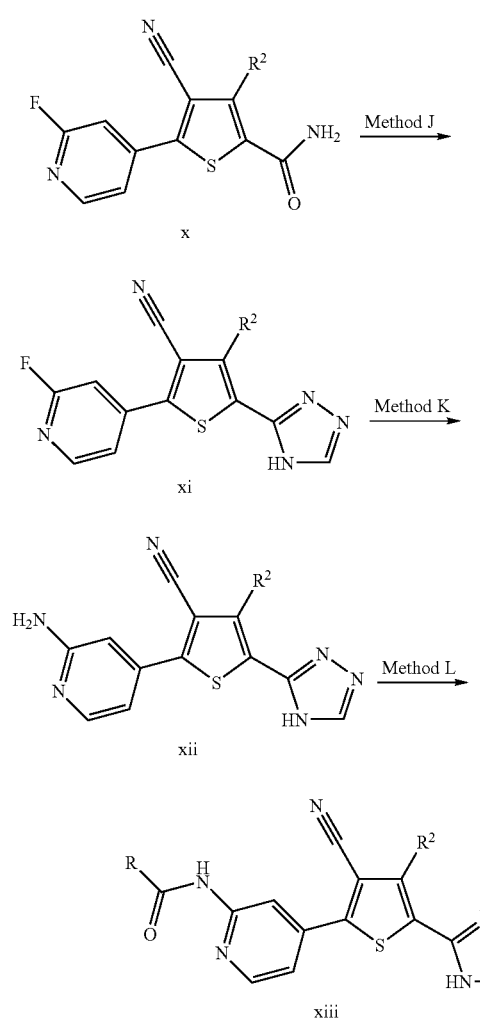

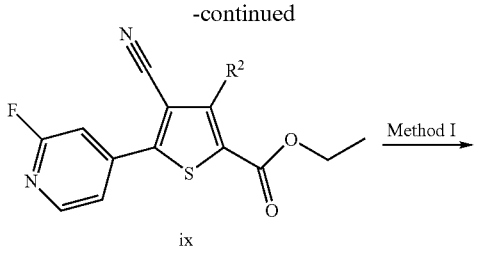

Scheme 1 above shows a general route for preparing compounds of formula xiii. As shown in Scheme 1, i is treated with ethyl thioacetate in the presence of a suitable base, such as TEA in MeOH under elevated temperature to afford ii (Method A), which is subjected to Sandmeyer reaction using appropriate reagents, such as methylene iodide and amyl nitrite in ACN (Method B). The product iii is then oxidized to sulfone iv using an appropriate oxidant, such as m-CPBA in DCM (Method C). Displacement of a sulfone is achieved using 2,4-dimethoxybenzylamine in THF at elevated temperature (Method D) to give v. Suzuki coupling of the latter compound with boronic acids is achieved using an appropriate catalyst, such as $Pd(dba)_2/tBu_3 \cdot BF_4$, in the presence of a suitable base, such as sodium carbonate in DME-water mixture under elevated temperature to afford compounds of formula vi (Method E). Deprotection of dimethoxybenzyl group is achieved with a suitable acid, such as TFA in DCM (Method F). Amines vii are then subjected to Sandmeyer reaction using appropriate reagents, such as methylene iodide and amyl nitrite in ACN (Method G). Esters viii can coupled with fluorpyridineboronic acid under standard Suzuki conditions, such as $Pd(PPh_3)_4$, $Na_2CO_3$, DME/water, microwave irradiation (Method H) to afford esters ix. Esters ix can be hydrolyzed using a suitable base, such as NaOH in aqueous conditions using cosolvents, such as TIM and MeOH to afford carboxylic acids followed by coupling with ammonia using a suitable coupling reagent, such as EDCI and HOBT in DCM to give amides x (Method I). Treatment of amides x with DMFDMA under elevated temperature gives intermediate enamines that are transformed to triazoles xi using hydrazine in acetic acid upon heating (Method J). Treatment of xi with ammonia in methanol under microwave irradiation affords aminopyridines xii (Method K) that can be subsequently coupled with acyl halides in the presence of a suitable base, such as TEA in DCM followed by treatment with a mild base, such as sodium bicarbonate to afford amides of formula xiii (Method L).

Scheme 2: Alternative synthesis of 3-substituted 4-cyano-5-pyridine-4-ylthiophene-2-triazoles

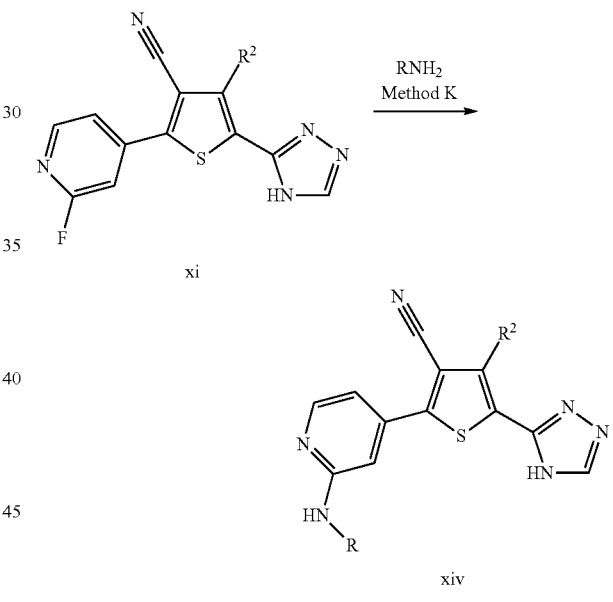

Scheme 2 above shows an alternative route for preparing compounds of formula xiv. As shown in Scheme 2, compounds xi can be heated with amines under microwave irradiation to give aminopyridines xiv (Method K).

Scheme 3: Alternative synthesis of 3-substituted 4-cyano-5-pyridine-4-ylthiophene-2-triazoles

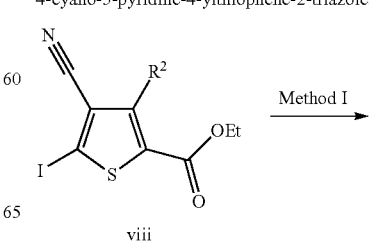

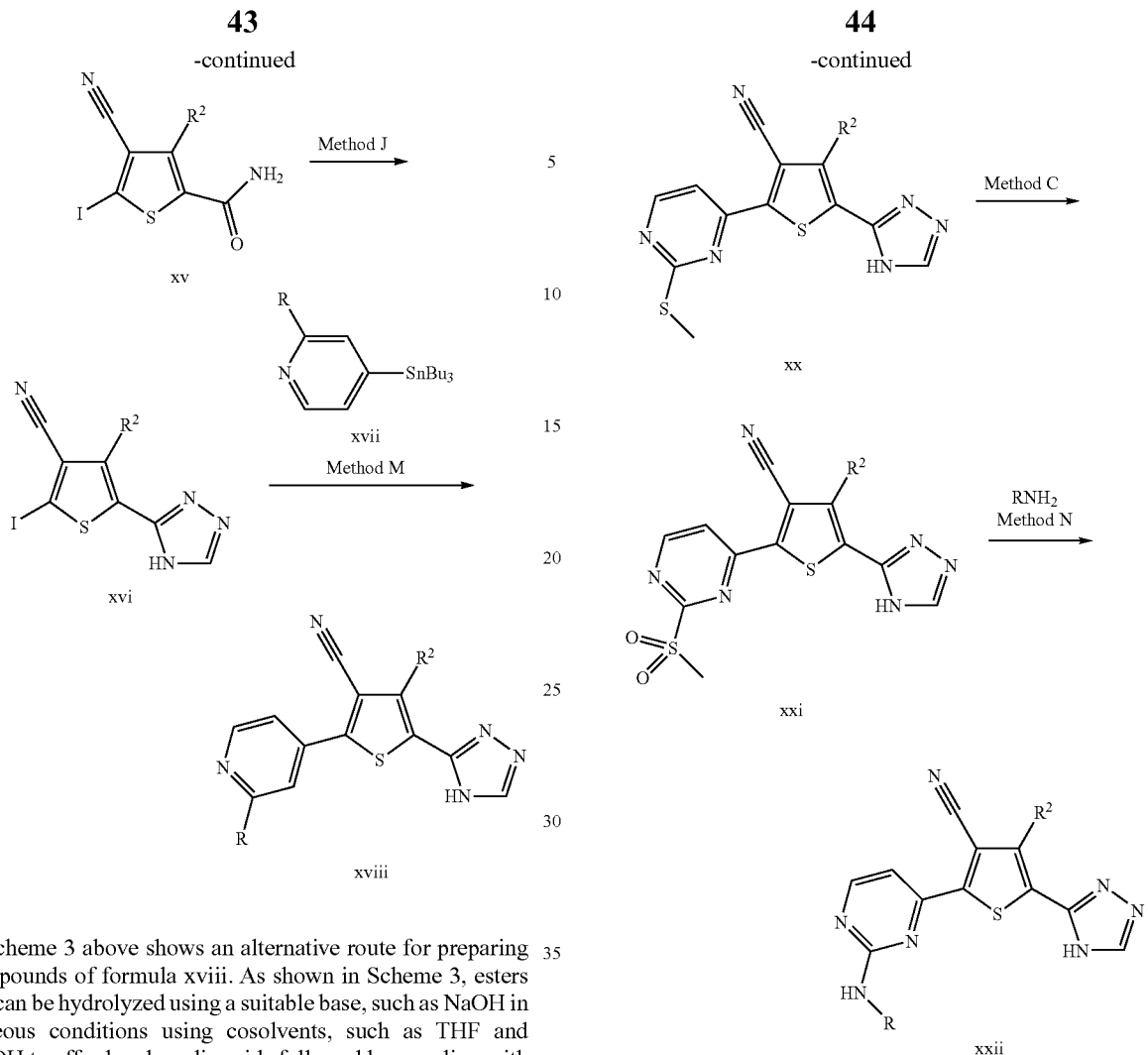

Scheme 3 above shows an alternative route for preparing compounds of formula xviii. As shown in Scheme 3, esters viii can be hydrolyzed using a suitable base, such as NaOH in aqueous conditions using cosolvents, such as THF and MeOH to afford carboxylic acids followed by coupling with ammonia using a suitable coupling reagent, such as EDCI and HOBT in DCM to give amides xv (Method I). Treatment of amides xv with DMFDMA under microwave irradiation gives intermediate enamines that are transformed to triazoles xvi using hydrazine in acetic acid under microwave irradiation (Method J). Compounds xvi can be then coupled with stannanes xvii under suitable conditions, for example Pd(PPh$_3$)$_4$, CuI, LiCl in dioxane at elevated temperature to give compounds xviii (Method M).

Scheme 4: Synthesis of 3-substituted 4-cyano-5-pyrimidine-4-ylthiophene-2-triazoles

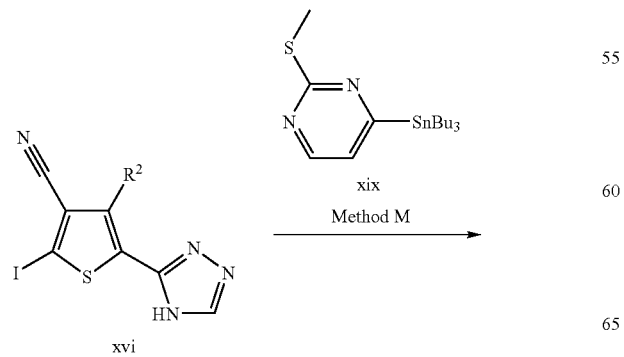

Scheme 4 above shows a general route for preparing compounds of formula xxii. As shown in Scheme 4, compounds xvi can be then coupled with stannane xix under suitable conditions, for example Pd(PPh$_3$)$_4$, CuI, LiCl in dioxane at elevated temperature to give compounds xx (Method M). Oxidation of thioethers xx to sulfones xxi can be achieved using a suitable oxidant, for example mCPBA in DCM (Method C). Sulfones xxi can be displaced by treatment with amines in a suitable solvent, for example THF to afford aminopyrimidines xxii (method N).

Scheme 5: General route for the synthesis of 3-substituted 4-cyano-5-aryl-thiophene-2-imidazoles

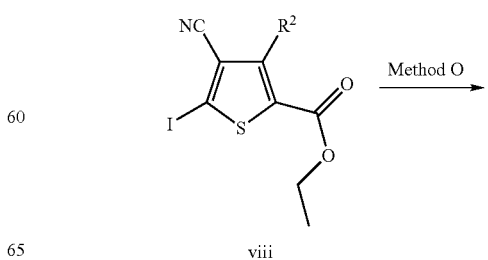

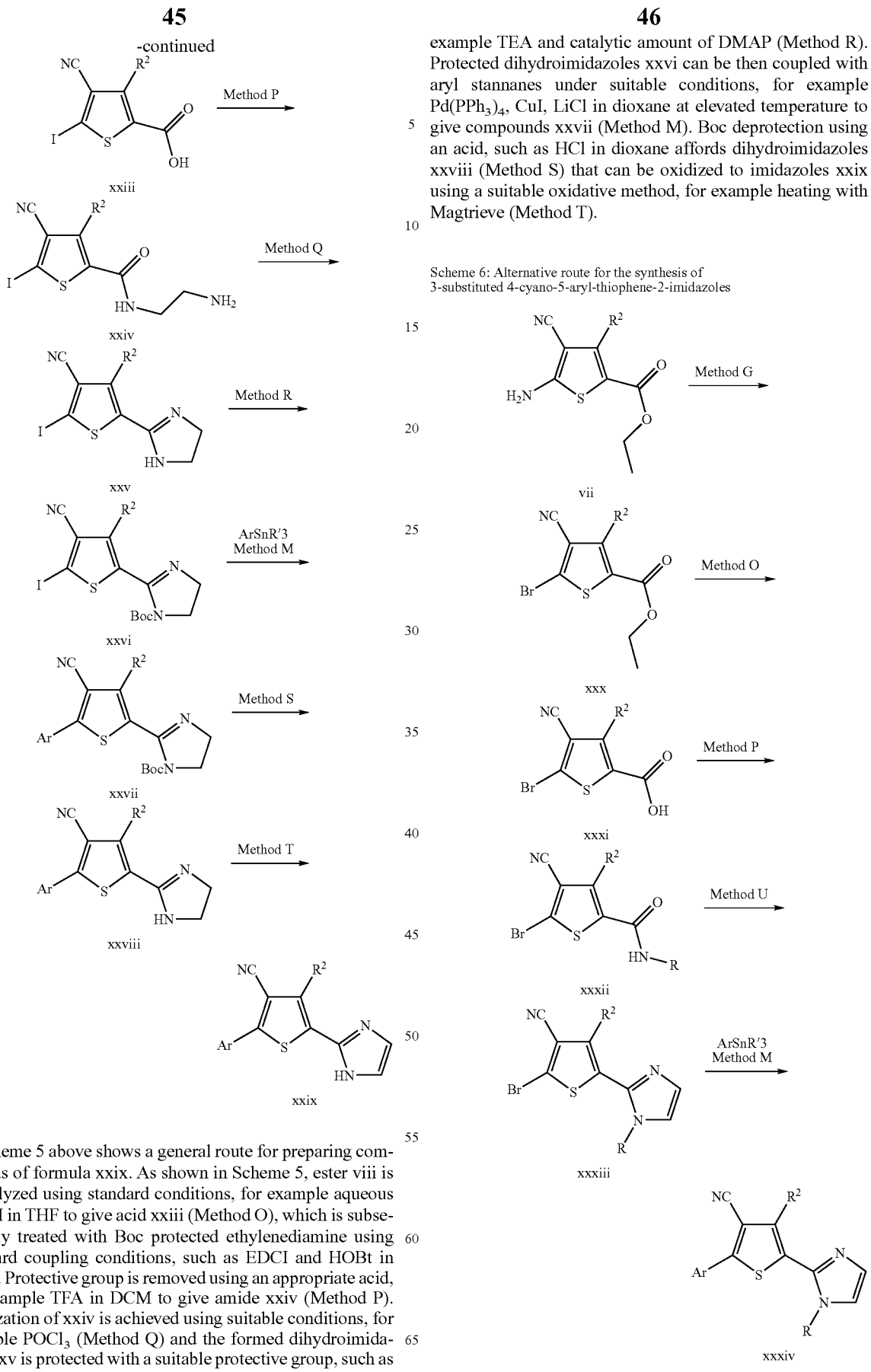

example TEA and catalytic amount of DMAP (Method R). Protected dihydroimidazoles xxvi can be then coupled with aryl stannanes under suitable conditions, for example Pd(PPh$_3$)$_4$, CuI, LiCl in dioxane at elevated temperature to give compounds xxvii (Method M). Boc deprotection using an acid, such as HCl in dioxane affords dihydroimidazoles xxviii (Method S) that can be oxidized to imidazoles xxix using a suitable oxidative method, for example heating with Magtrieve (Method T).

Scheme 6: Alternative route for the synthesis of 3-substituted 4-cyano-5-aryl-thiophene-2-imidazoles Scheme 5 above shows a general route for preparing compounds of formula xxix. As shown in Scheme 5, ester viii is hydrolyzed using standard conditions, for example aqueous NaOH in THF to give acid xxiii (Method O), which is subsequently treated with Boc protected ethylenediamine using standard coupling conditions, such as EDCI and HOBt in DCM. Protective group is removed using an appropriate acid, for example TFA in DCM to give amide xxiv (Method P). Cyclization of xxiv is achieved using suitable conditions, for example POCl$_3$ (Method Q) and the formed dihydroimidazole xxv is protected with a suitable protective group, such as Boc by treatment with Boc$_2$O in a presence of a base, for Scheme 6 above shows an alternative route for preparing compounds of formula xxxiv. As shown in Scheme 6, ester vii is subjected to Sandmeyer reaction using for instance copper (II) bromide and tert. butyl nitrite (Method G) to afford xxx, which is hydrolyzed using standard conditions, for example aqueous NaOH in THF to give acid xxxi (Method O). Acid xxxi is subsequently treated with an amine using standard coupling conditions, such as EDCI and HOBt in DCM to afford amides xxxii (Method P). Cyclization to imidazoles is achieved through a 3-step one pot process that involves treatment with phosphorus pentachloride and HCl in dioxane to afford carbimidoyl chloride intermediate, which is then treated with aminoacetaldehyde dimethylacetal followed by HCl in dioxane at elevated temperature to give xxxiii (Method U). Compounds xxxiii can be then coupled with aryl stannanes under suitable conditions, for example Pd(PPh$_3$)$_4$, CuI, LiCl in dioxane at elevated temperature to give compounds xxxiv (Method M).

Where appropriate, the above described transformations of thiophene nitriles can be also applied to thiophenes with R$_3$ substituents other than nitrile group.

Alternatively, lithium intermediates xxxvi can be transformed to stannanes by quenching with suitable tin halide, such as tributyltin chloride (Method X). Stannanes xxxviii are then coupled with aryl halides, triflates, or mesylates using appropriate conditions, such as Pd(PPh$_3$)$_4$, CuI, LiCl in a suitable solvent, such as dioxane at elevated temperature to give compounds of formula xxxix (Method M).

Scheme 8: General route for the construction of halogenated 1,2,4-triazoles

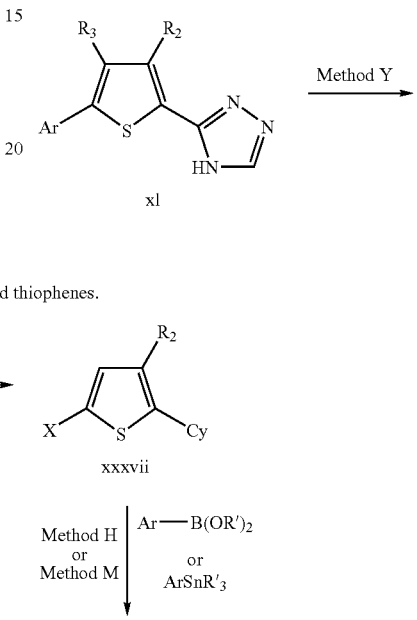

Scheme 7: General method for the introduction of aryl group to 2-unsubstituted thiophenes.

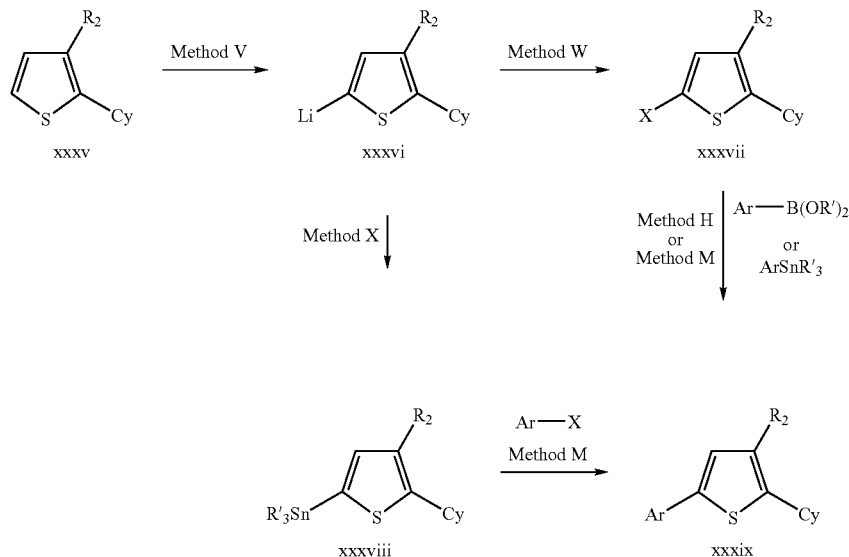

Scheme 7 above shows a general route for introducing aryl to 2-position on thiophene core. 2-unsubstituted thiophene xxxv can be treated with suitable base, such as n-BuLi in THF at low temperature, to produce lithiated thiophene intermediate xxxvi (Method V). The intermediate organolithium species can be quenched with halogen molecule, for example iodine in a suitable solvent, such as THF to afford halogenated compounds of formula xxxvii (Method W). Halides xxxvii can be coupled with aryl stannanes under suitable conditions, for example Pd(PPh$_3$)$_4$, CuI, LiCl in a suitable solvent, such as dioxane at elevated temperature to give compounds of formula xxxix (Method M), or boronic acids or esters with an appropriate catalyst, for example Pd(PPh$_3$)$_4$, in the presence of a suitable base, such as sodium carbonate in DME-water mixture at elevated temperature (Method H) to afford compounds of formula xxxix.

-continued

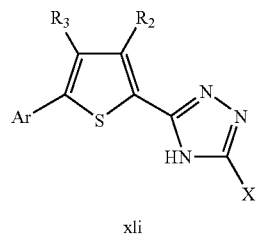

As shown in Scheme 8, triazoles xl are treated with a suitable halogenating agent, like NBS in a suitable solvent, for example tetrachloromethane to afford compounds of formula xli (Method Y).

Scheme 9: Alternative method for the construction of substituted 2-imidazolyl.

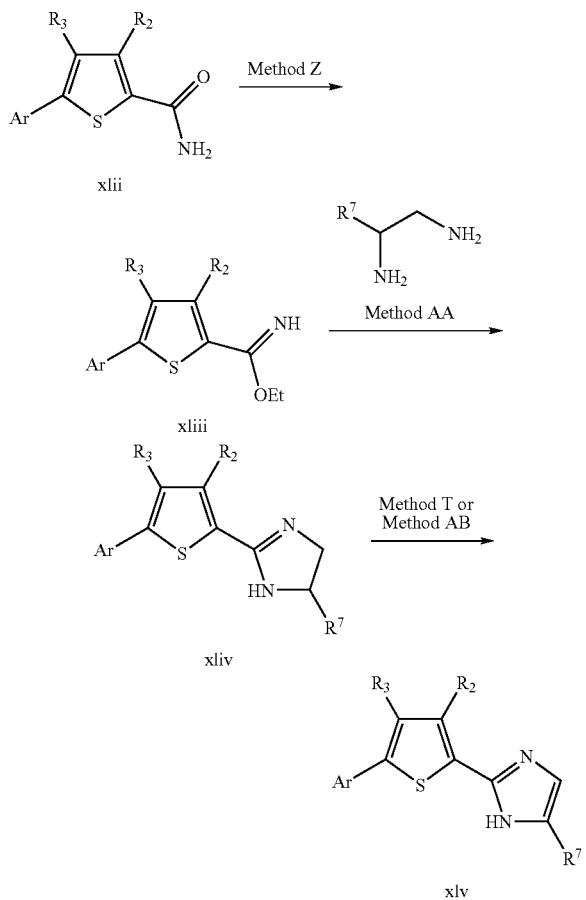

As shown in scheme 9, treatment of amides xlii with an alkylating agent, such as Meerwein's reagent in DCM gives iminoesters xliii (Method Z), which are then treated with diamines using appropriate conditions, for example ethanol at elevated temperature (Method AA). Formed dihydroimidazoles xliv can be then oxidized in a same manner as in Method T, or when $R_7$ is a leaving group, elimination can be carried out using a base, such as DBU in DCM (Method AB).

Scheme 10: General route for the construction of substituted 4 (5)-imidazolyl.

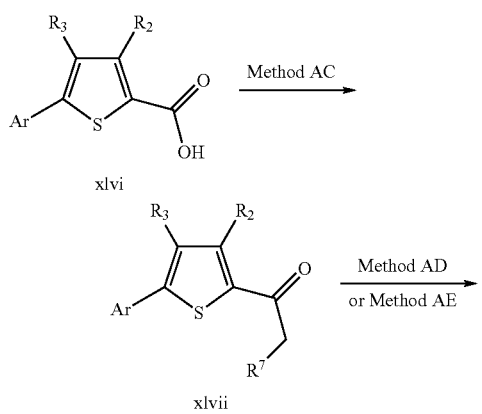

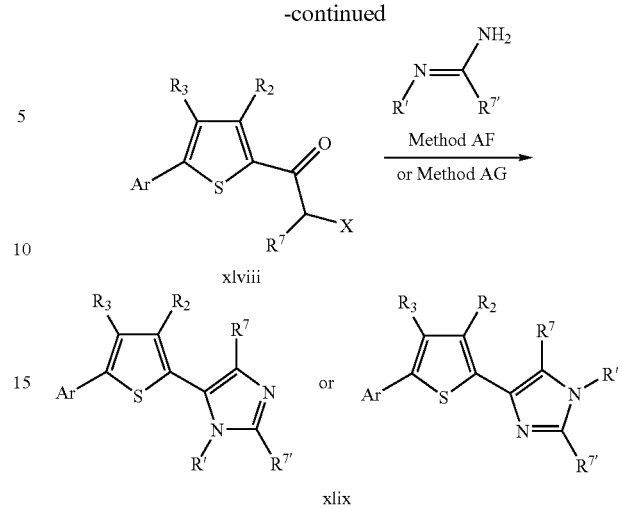

As shown in Scheme 10, acids xlvi are transformed to ketones using a suitable synthetic sequence, for example through a coupling with N,O-dimethylhydroxylamine and subsequent treatment of the formed Weinreb amides with alkyllithium reagents in a suitable solvent, like THF (Method AC). Ketones xlvii are then halogenated with a suitable reagent, such as bromine or NBS in an appropriate solvent, like DCM (Method AD) to form compounds xlviii (X=halogen). Alternatively, treatment of ketones xlvii with a suitable oxidative sulfonylating agent, like hydroxy(tosyloxy)iodobenzene using suitable conditions, for example heating in acetonitrile (Method AE) affords sulfonyl esters of formula xliii (X=$OSO_2R$).

Treatment of xlviii with amidine reagents in the presence of a suitable base, like potassium carbonate in a suitable solvent, such as THF-water mixture at elevated temperature or microwave irradiation affords the final imidazoles il (Method AF). Alternatively, compounds xlviii can be treated with large excess of amides, such as formamide using microwave irradiation to afford imidazoles il (Method AG).

Scheme 11: General route for the construction of 3 (5)-pyrrazolyl.

As shown in Scheme 11, ketones xlvii are treated with DMFDMA to afford intermediate enamines followed by reaction with substituted hydrazine, or hydrazine hydrate in a suitable solvent, for example acetic acid to give pyrazoles l (Method AH).

Scheme 12: General route for the construction of 1,2,3-triazolyl.

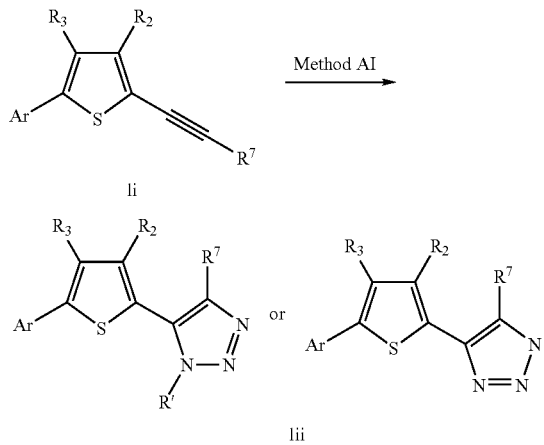

As shown in Scheme 12, alkynes li, which can be prepared by the known Stille- or Sonogashira-coupling reaction of halides and appropriate alkyne derivative, are treated with azides, inorganic or organic a suitable solvent, such as dioxane at elevated temperature to afford triazoles of formula lii (Method AI).

Scheme 13: General route for the construction of tetrazolyl.

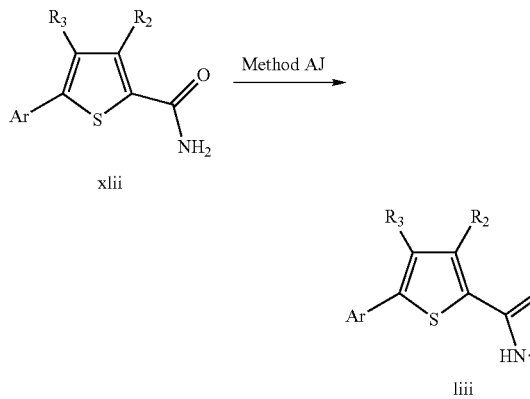

As shown in Scheme 13, amides xlii are treated with an azide source, for example sodium azide using a suitable Lewis acid, for example silicon tetrachloride in an appropriate solvent, such as acetonitrile to give tetrazoles liiii (Method AJ).

Scheme 14: General method for the introduction of 2-acylaminopyridines by Buchwald reaction.

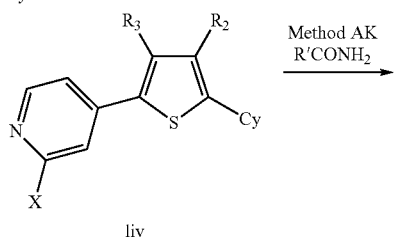

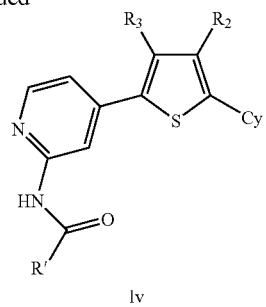

Scheme 14 above shows a general route for the transformation of 2-halopyridyl to 2-acylaminopyridyl by Buchwald reaction to give the compounds formula lv.

As shown in Scheme 14, compounds liv can be treated with amides or carboxamides in the presence of a suitable catalyst, such as $Pd_2 dba_3$, XantPhos, base like cesium carbonate in an appropriate solvent, for example dioxane at elevated temperature or under microwave irradiation to give acylaminopyridines lv (Method AK).

5. Uses, Formulation and Administration

As discussed above, the present invention provides compounds that are useful as inhibitors of PI3K enzymes, and thus the present compounds are useful for treating proliferative, inflammatory, or cardiovascular disorders such as tumor and/or cancerous cell growth mediated by PI3K. In particular, the compounds are useful in the treatment of cancers in a subject, including, but not limited to, lung and bronchus, prostate, breast, pancreas, colon and recum, thyroid, liver and intrahepatic bile duct, hepatocellular, gastric, glioma/glioblastoma, endometrial, melanoma, kidney, and renal pelvis, urinary bladder, utering corpus, uterine cervix, ovary, multiple myeloma, esophagus, acute myelogenous leukemia, chronic myelogenous leukemia, lymphocytic leukemia, myeloid leukemia, brain, oral cavity, and pharynx, small intestine, non-Hodgkin lymphoma, and villous colon adenoma.

In some embodiments, compounds of the invention are suitable for the treatment of breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, or ovarian cancer.

In other embodiments, compounds of the invention are suitable for the treatment of inflammatory and cardiovascular disorders including, but not limited to, allergies/anaphylaxis, acute and chronic inflammation, rheumatoid arthritis; autoimmunity disorders, thrombosis, hypertension, cardiac hypertrophy, and heart failure.

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of PI3K.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component (s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, or cardiovascular disorder is provided comprising administering an effective amount of a compound, or a pharmaceutical composition to a subject in need thereof. In certain embodiments of the present invention an "effective amount" of the compound or pharmaceutical composition is that amount effective for treating a proliferative, inflammatory, or cardiovascular disorder, or is that amount effective for treating cancer. In other embodiments, an "effective amount" of a compound is an amount which inhibits binding of PI3K and thereby blocks the resulting signaling cascades that lead to the abnormal activity of growth factors, receptor tyrosine kinases, protein serine/threonine kinases, G protein coupled receptors and phospholipid kinases and phosphatases.

The compounds and compositions, according to the method of the present invention, may be administered using any amount and any route of administration effective for treating the disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient (s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

While one or more of the inventive compounds may be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

In one embodiment, the compounds of this invention are used in combination with other therapeutic agents, such as other inhibitors of PI3K. In some embodiments, a compound of the invention is administered in conjunction with a therapeutic agent selected from the group consisting of cytotoxic agents, radiotherapy, and immunotherapy. It is understood that other combinations may be undertaken while remaining within the scope of the invention.

Another aspect of the invention relates to inhibiting PI3K, activity in a biological sample or a patient, which method comprises administering to the patient, or contacting said biological sample with a compound of formula I or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/or salts thereof are used in combination with pharmaceutically acceptable carriers to treat disorders, symptoms and diseases where PI3K kinase plays a role.

EXPERIMENTAL PROCEDURES

I. Preparation of Exemplary Compounds

Definitions

AcOH acetic acid
ACN acetonitrile
ATP adenosine triphosphate
BCA bicinchoninic acid
BSA bovine serum albumin
BOC tert-butoxycarbonyl
BuLi butyllithium
m-CPBA m-chloroperbenzoic acid
DCE dichloroethane
DCM dichloromethane
DDQ 2,3-dichloro-5,6-dicyano-1,4-benzoquinone
DIPEA diisopropylethyl amine
DMEM Dulbecco's Modified Eagle's Medium
DMF N,N-dimethylformamide
DMFDMA N,N-dimethylformamide dimethyl acetal
DMSO dimethylsulfoxide
DPPA diphenylphosphoryl azide
DTT dithiothreitol
dppf diphenylphosphinoferrocene
EDCI N-(3-dimethylaminopropyl)-N'-ethylcarbodiimide hydrochloride
EDTA ethylenediaminetetraacetic acid
EtOAc ethyl acetate
EtOH ethanol
FA formic acid
FBS fetal bovine serum
h hours
HATU N,N,N',N'-tetramethyl-o-(7-azabenzotriazole-1-yl) uronium hexafluorophosphate
HBTU o-benzotriazol-1-yl-N,N,N',N'-tetramethyluronium hexafluorophosphate
HEPES N-(2-Hydroxyethyl)piperazine-N'-(2-ethanesulfonic acid)
HOBT 1-hydroxybenztriazole hydrate
FIRMS high resolution mass spectrum
LAH lithium aluminum hydride
LCMS liquid chromatography mass spectrum
LDA lithium diisopropylamide
LiHMDS Lithium bis(trimethylsilyl)amide
m/z mass to charge
Me methyl
MeOH methanol
min minutes
MS mass spectrum
MTT methylthiazoletetrazolium
MWI microwave irradiation
PBS phosphate buffered saline
PKA cAMP-dependent protein kinase
rt room temperature
TEA triethylamine
TFFA trifluoroacetic anhydride
THF tetrahydrofuran
TMB 3,3',5,5'-Tetramethylbenzidine
TMEDA Tetramethylethylenediamine
WST (4-[3-(4-iodophenyl)-2-(4-nitrophenyl)-2H-5-tetrazolio]-1,3-benzene disulfonate sodium salt)
Analytical LC-MS Methods
LCMS Conditions Spectra were run on a Phenominex Luna 5 µm C18 50×4.6 mm column on a Hewlett-Packard HP1100 using the following gradients:

Method Formic Acid (FA): Acetonitrile containing 0 to 100 percent 0.1% formic acid in water (2.5 ml/min for a 3 minute run).

Method Ammonium Acetate (AA): Acetonitrile containing 0 to 100 percent 10 mM ammonium acetate in water (2.5 ml/min for a 3 minute run).

NMR spectrum is shown by proton NMR, with tetramethylsilane as the internal standard and using 300 MHz Bruker Avance spectrometer equipped with a 5 mm QNP probe and 400 MHz Bruker Avance II spectrometer equipped with a 5 mm QNP probe for the measurement; δ values are expressed in ppm.
Example 1
Synthesis of N-(4-(3-cyano-4-(2,4-dichlorophenyl)-5-(4H-1,2,4-triazol-3-yl)thiophen-2-yl)pyridin-2-yl)cyclopropanecarboxamide (32)
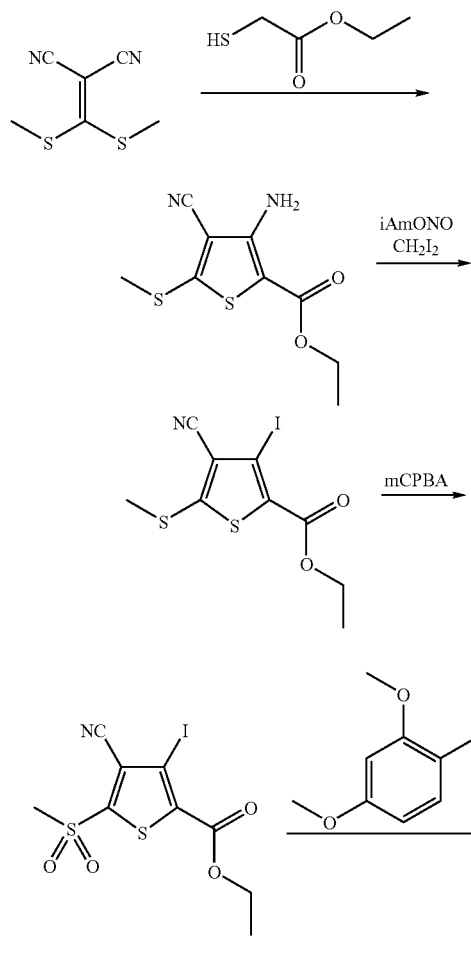
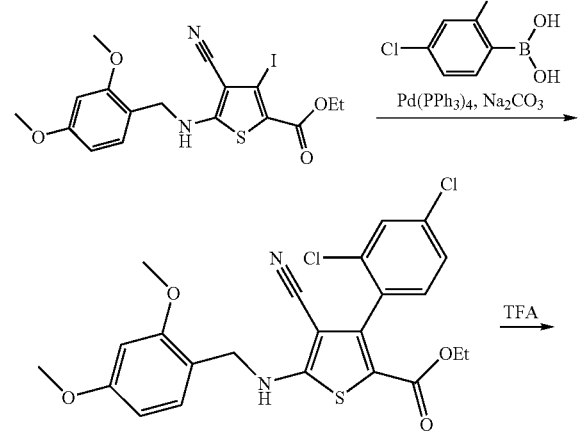
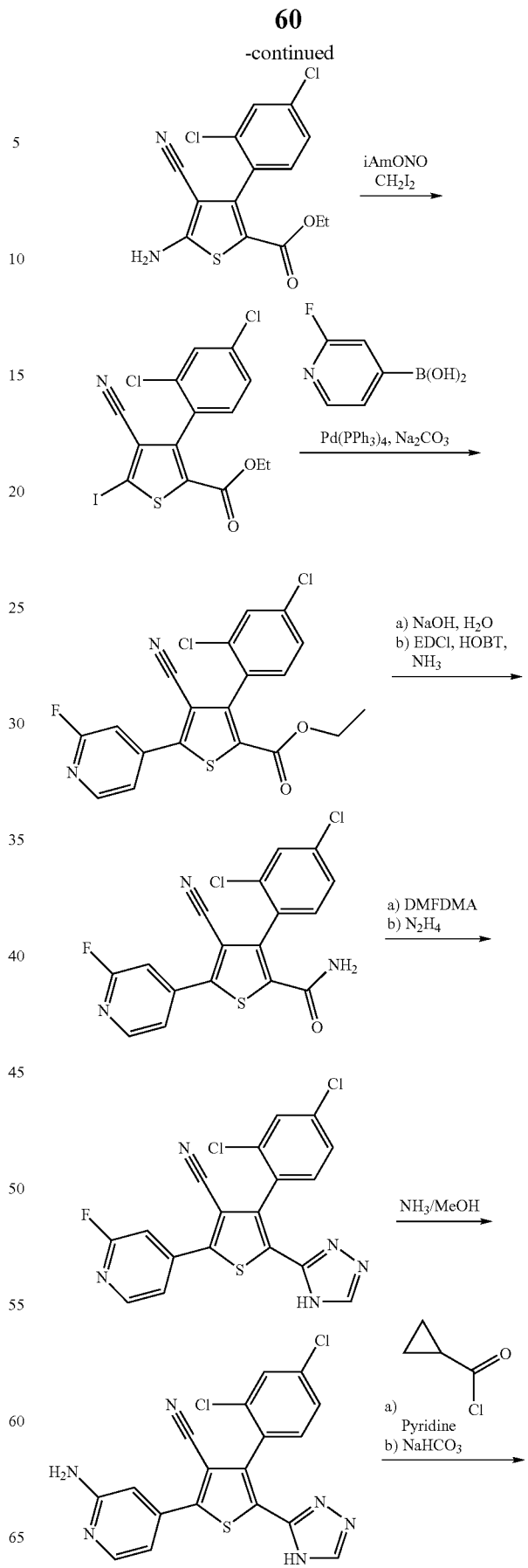

-continued

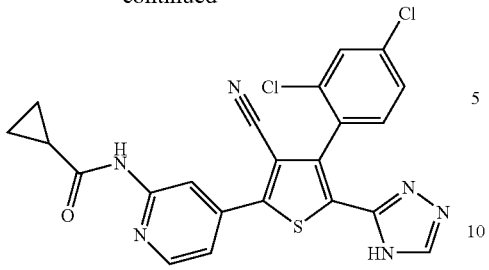

Step 1: Ethyl 3-amino-4-cyano-5-(methylsulfanyl) thiophene-2-carboxylate

A mixture of [bis(methylsulfanyl)methylene]malononitrile (40 g, 230 mmol), ethylthioglycolate (29 g, 230 mmol) and TEA (24 mL, 173 mmol) in MeOH (600 mL) was allowed to stir at reflux for 2 h. The reaction mixture was allowed to cool overnight and the precipitate was filtered off, washed with cold MeOH (3×50 mL) to give ethyl 3-amino-4-cyano-5-(methylsulfanyl)thiophene-2-carboxylate (52.4 g, 99%). LCMS: (FA) ES+ 275.

Step 2: Ethyl 4-cyano-3-iodo-5-(methylsulfanyl) thiophene-2-carboxylate

Ethyl 3-amino-5-(methylsulfanyl)thiophene-2-carboxylate (10 g, 41.3 mmol) was dissolved in acetonitrile (50 mL) under an atmosphere of argon. Diiodomethane (11.6 mL, 0.144 mol) was added and the mixture was heated at 40° C. Isoamyl nitrite (12.1 g, 0.103 mol) was added and the reaction was allowed to cool to room temperature and stirred for 2 hours. Mixture was cooled down at 0° C., diluted with hexane (50 mL) and the precipitate was filtered off, washed with 10:1 hexane-acetonitrile mixture (10 mL), 3:1 hexane-ether (10 mL) and hexane (10 mL). The precipitate was dried to afford ethyl 4-cyano-3-iodo-5-(methylsulfanyl)thiophene-2-carboxylate (6.90 g, 45%). LCMS: (FA) ES+ 354. $^1$H NMR (400 MHz, $d_1$-chloroform) δ: 4.38 (q, 2H), 2.70 (s, 3H), 1.40 (t, 3H).

Step 3: Ethyl 4-cyano-3-iodo-5-(methylsulfonyl) thiophene-2-carboxylate

Ethyl 4-cyano-3-iodo-5-(methylsulfanyl)thiophene-2-carboxylate (7.2 g, 20.4 mmol) was dissolved in DCM (200 mL) and THF (100 mL) and m-CPBA (9.14 g, 40.8 mmol) was added. The reaction mixture was stirred at rt overnight. Sodium sulfite (5.14 g, 40.8 mmol) was added, stirred for 10 minutes followed by addition of potassium carbonate (8.45, 61.2 mmol). The suspension was stirred at rt for 1 hour and filtered through celite, washed with DCM and the solvent was evaporated to afford ethyl 3-iodo-4-cyano-5-(methylsulfonyl)thiophene-2-carboxylate (6.80 g, 78%). LCMS: (FA) ES+ 386. $^1$H NMR (400 MHz, $d_1$-chloroform) δ: 4.45 (q, 2H), 3.38 (s, 3H), 1.43 (t, 3H).

Step 4: Ethyl 4-cyano-5-[(2,4-dimethoxybenzyl) amino]-3-iodothiophene-2-carboxylate Ethyl 4-cyano-3-iodo-5-(methylsulfonyl)thiophene-2-carboxylate (5.60 g, 0.0145 mol) and 2,4-dimethoxybenzylamine (3.51 mL, 0.0234 mol) were combined in tetrahydrofuran (100 mL) and stirred at 60° C. for 3 days. The reaction was concentrated in vacuo, diluted with dichloromethane and hexanes and the resultant precipitate was filtered to yield the title compound (5.56, 81%) as a yellow solid. LCMS: (FA) ES+, 473. $^1$H NMR (400 MHz, $d_6$-DMSO) δ: 9.05 (s, 1H) 7.10 (d, 1H, J=8.57 Hz), 6.60-6.50 (m, 2H), 4.30 (s, 2H), 4.22-4.14 (m, 2H), 3.80 (s, 3H), 3.75 (s, 3H), 1.26-1.21 (m, 3H).

Step 5: Ethyl 4-cyano-3-(2,4-dichlorophenyl)-5-[(2, 4-dimethoxybenzyl)amino]thiophene-2-carboxylate Ethyl 4-cyano-5-[(2,4-dimethoxybenzyl)amino]-3-iodothiophene-2-carboxylate (3.18 g, 0.00673 mol) 2,4-dichlorophenylboronic acid (2.72 g, 0.0143 mol), Pd(dba)$_2$ (0.33 g, 0.00036 mol), PtBu$_3$.BF$_4$ (0.21 g, 0.00072 mmol) and sodium carbonate (2.42 g, 0.0228 mol) were suspended in 1,2-dimethoxyethane (250 mL) and water (80 mL). The suspension was flushed with argon and the reaction mixture was heated at reflux for 7 hours. The reaction mixture was diluted with a saturated solution of sodium bicarbonate in water and extracted with ethyl acetate. The organic extracts were washed with brine, dried over anhydrous sodium sulfate, filtered and concentrated in vacuo. Column chromatography was performed to yield the title compound (2.92 g, 88%). LCMS: (FA) ES+, 491. $^1$H NMR (400 MHz, $d_6$-DMSO) δ: 9.05 (bs, 1H) 7.75 (d, 1H, J=2.00 Hz), 7.52-7.48 (m, 1H), 7.40 (d, 1H, J=8.28 Hz), 7.19 (d, 1H, J=8.53 Hz), 6.62-6.53 (m, 2H), 4.35 (bs, 2H), 4.04-3.92 (m, 2H), 3.83 (s, 3H), 3.76 (s, 3H), 1.01-0.96 (m, 3H).

Step 6: Ethyl 5-amino-4-cyano-3-(2,4-dichlorophenyl)thiophene-2-carboxylate

Ethyl 4-cyano-3-(2,4-dichlorophenyl)-5-[(2,4-dimethoxybenzyl)amino]thiophene-2-carboxylate (4.70 g, 0.00956 mol) was dissolved in dichloromethane (100 mL). Trifluoroacetic acid (25 mL) was added and the solution was stirred at room temperature for 10 minutes. The reaction was concentrated in vacuo, diluted with ethyl acetate and filtered. The filtrate was washed with saturated sodium bicarbonate and brine, dried over anhydrous sodium sulfate, filtered and concentrated in vacuo. Column chromatography was performed to yield the title compound (2.92 g, 90%) as a yellow solid. LCMS: (FA) ES+, 341. $^1$H NMR (400 MHz, $d_6$-DMSO) δ: 8.17 (s, 2H) 7.75 (d, 1H, J=2.00 Hz), 7.52-7.48 (m, 1H), 7.39 (d, 1H, J=8.28 Hz), 4.05-3.92 (m, 2H), 1.02-0.96 (m, 3H).

Step 7: Ethyl 4-cyano-3-(2,4-dichlorophenyl)-5-iodothiophene-2-carboxylate

To a suspension of ethyl 5-amino-4-cyano-3-(2,4-dichlorophenyl)thiophene-2-carboxylate (2.92 g, 0.00856 mol) in acetonitrile (10 mL) was added diiodomethane (2.41 mL, 0.0300 mol) under an atmosphere of argon and was heated at 38° C. Isoamyl nitrite (2.61 g, 0.0214 mol) was added dropwise and the reaction mixture was cooled to room temperature and stirred for one hour. The reaction was concentrated in vacuo and column chromatography was performed to yield the title compound (1.44 g, 37%) as an orange solid. $^1$H NMR (400 MHz, $d_1$-chloroform) δ: 7.53 (d, 1H, J=2.00 Hz), 7.38-7.34 (m, 1H), 7.21 (d, 1H, J=8.28 Hz), 4.25-4.15 (m, 2H), 1.21-1.16 (m, 3H).

Step 8: Ethyl 4-cyano-3-(2,4-dichlorophenyl)-5-(2-fluoropyridin-4-yl)thiophene-2-carboxylate A mixture of ethyl 4-cyano-3-(2,4-dichlorophenyl)-5-iodothiophene-2-carboxylate (1.81 g, 0.00400 mol), 2-Fluoro- 4-pyridinylboronic acid (1.13 g, 0.00801 mol), Tetrakis (triphenylphosphine)palladium(0) (0.231 g, 0.0002 mol) and sodium carbonate (1.27 g, 0.0120 mol) in 1,2-Dimethoxyethane (20 mL) and Water (10 mL) was heated under microwave irradiation at 140° C. for 15 min. The reaction mixture was diluted with EtOAc and sat. NaHCO₃. The layers were separated and the aqueous layer was extracted 2× with EtOAc. The combined organic extracts were washed with brine, dried over Na₂SO₄, filtered and concentrated to in vacuo to a brown oil. The residue was loaded onto a 24 g Analogix silica gel column and eluted with hexane (3 min) to 50% EtOAc in hexanes (25 min gradient). The appropriate fractions were concentrated to a white solid (1.25 g, 74%). LCMS: (FA) ES⁺, 421, 423. ¹H NMR (400 MHz, d₆-DMSO) δ 8.42 (d, J=5.28 Hz, 1H), 7.65 (td, J=5.27, 1.51, 1.51 Hz, 1H), 7.57 (d, J=2.00 Hz, 1H), 7.45-7.34 (m, 1H), 7.29 (d, J=8.26 Hz, 1H), 4.34-4.17 (m, 1H), 1.21 (t, J=7.14, 7.14 Hz, 1H).

Step 9: 4-cyano-3-(2,4-dichlorophenyl)-5-(2-fluoropyridin-4-yl)thiophene-2-carboxamide Ethyl 4-cyano-3-(2,4-dichlorophenyl)-5-(2-fluoropyridin-4-yl)thiophene-2-carboxylate (2.33 g, 0.00553 mol) was dissolved in acetonitrile (100 mL) and 1M sodium hydroxide in water (42 mL, 0.0420 mol) was added. The mixture was stirred overnight at room temperature. The mixture was concentrated and the residue was acidified with 1N HCl. The solid was collected, dried, and used in the next step without purification. The above solid was dissolved in methylene chloride (248 mL) and N-(3-dimethylaminopropyl)-N'-ethylcarbodiimide hydrochloride (2.29 g, 0.0120 mol) and 1-hydroxybenzotriazole hydrate (1.694 g, 0.01106 mol) were added. The mixture was stirred at room temperature for 15 minutes and 33% ammonium hydroxide (20.0 mL, 0.231 mol) was added. The stirring was continued for 2 hours. The mixture was diluted with DCM and washed with water and brine. The organic layer was dried and purified by column chromatography on silica gel (80 g), elution hexane to 60% EtOAc in hexane over 30 minutes. The product was obtained as white solid (1.18 g, 55%). LCMS: (FA) ES⁺, 392, 394. ¹H NMR (400 MHz, d₆-DMSO) δ 8.50 (d, J=5.27 Hz, 1H), 7.85 (d, J=1.79 Hz, 1H), 7.79 (td, J=5.21, 1.52, 1.52 Hz, 1H), 7.65 (s, 1H), 7.63-7.55 (m, 2H), 7.42 (bs, 1H), Step 10: 4-(2,4-dichlorophenyl)-2-(2-fluoropyridin-4-yl)-5-(4H-1,2,4-triazol-3-yl)thiophene-3-carbonitrile A mixture of 4-cyano-3-(2,4-dichlorophenyl)-5-(2-fluoropyridin-4-yl)thiophene-2-carboxamide (0.90 g, 0.0022 mol) in 1,1-dimethoxy-N,N-dimethylmethanamine (5.50 g, 0.045 mol) was stirred at 85° C. overnight. The mixture was evaporated to dryness and the residue was dissolved in acetic acid (14 mL, 0.2 mol) and hydrazine hydrate (1.4 mL, 0.02 mol) was added. The mixture was stirred at 85° C. for 5 hours. The solvent was removed and the residue was suspended in water. The precipitate was collected and dried in an oven to afford the product (0.86 g, 90%). LCMS: (FA) ES⁺, 416, 418. ¹H NMR (400 MHz, d₄-Methanol) δ 8.42 (s, 1H), 8.41 (d, J=5.21 Hz, 1H), 7.81 (td, J=5.33, 1.58, 1.58 Hz, 1H), 7.63 (t, J=1.18, 1.18 Hz, 1H), 7.60 (s, 1H), 7.48-7.46 (m, 2H).

Step 11: 2-(2-aminopyridin-4-yl)-4-(2,4-dichlorophenyl)-5-(4H-1,2,4-triazol-3-yl)thiophene-3-carbonitrile A mixture of 4-(2,4-dichlorophenyl)-2-(2-fluoropyridin-4-yl)-5-(4H-1,2,4-triazol-3-yl)thiophene-3-carbonitrile (0.600 g, 0.00144 mol) and 7 M ammonia in methanol (40 mL, 0.280 mol) was irradiated in a microwave at 150° C. for 8 hours. Solvent was evaporated and the residue was purified by column chromatography on silica gel (40 g), gradient DCM to 6% MeOH in DCM over 30 minutes to afford the title compound as yellow solid (0.26 g, 44%). LCMS: (FA) ES⁺, 413, 415. ¹H NMR (400 MHz, d₄-Methanol) δ 8.40 (s, 1H), 8.05 (dd, J=5.16, 1.10 Hz, 1H), 7.61 (dd, J=1.54, 0.76 Hz, 1H), 7.46-7.42 (m, 2H), 7.03-7.00 (m, 2H)

Step 12: N-(4-(3-cyano-4-(2,4-dichlorophenyl)-5-(4H-1,2,4-triazol-3-yl)thiophen-2-yl)pyridin-2-yl)cyclopropanecarboxamide (32-A)

To a mixture of 2-(2-aminopyridin-4-yl)-4-(2,4-dichlorophenyl)-5-(4H-1,2,4-triazol-3-yl)thiophene-3-carbonitrile (0.100 g, 0.24 mmol) in pyridine (0.39 mL, 4.8 mmol) and methylene chloride (10 mL) was added cyclopropanecarbonyl chloride 0.050 mL, 0.54 mmol) at 0° C. The mixture was stirred at 0° C. for 2 hours. Saturated sodium bicarbonate solution (5 mL) was added and the mixture was vigorously stirred for 15 min. The mixture was extracted with DCM, dried, filtered and evaporated and the residue was purified by column chromatography on silica gel (40 g) using DCM to 3% MeOH in DCM over 30 minutes to afford the product (0.041 g, 36%). LCMS: (FA) ES⁺, 481, 483. ¹H NMR (400 MHz, d₄-Methanol) δ 8.49-8.42 (m, 2H), 8.40 (s, 1H), 7.66 (dd, J=5.58, 1.76 Hz, 1H), 7.62 (t, J=1.16, 1.16 Hz, 1H), 7.46-7.44 (m, 2H), 1.99-1.87 (m, 1H), 1.11-1.03 (m, 2H), 1.00-0.94 (m, 2H)

Compounds in the following table were prepared from the appropriate starting materials in a method analogous to that of Example 1:

| | |
|---|---|
| 1 | LCMS: (FA) ES+ 517, 519. |
| 2 | LCMS: (FA) ES+ 469, 471. |
| 3 | LCMS: (FA) ES+ 545, 547. |
| 4 | LCMS: (FA) ES+ 491, 493. |
| 6 | LCMS: (FA) ES+ 470, 472. |
| 9 | LCMS: (FA) ES+ 374, 376. |
| 11 | LCMS: (FA) ES+ 413, 415. |
| 15 | LCMS: (FA) ES+ 490, 492. |
| 17 | LCMS: (FA) ES+ 522, 524. |
| 18 | LCMS: (FA) ES+ 398, 400. |
| 20 | LCMS: (FA) ES+ 471, 473. |
| 24 | LCMS: (FA) ES+ 428, 430. |
| 25 | LCMS: (FA) ES+ 553, 555. |
| 28 | LCMS: (FA) ES+ 498, 500. |
| 29 | LCMS: (FA) ES+ 392, 394. |
| 30 | LCMS: (FA) ES+ 431, 433. |
| 38 | LCMS: (FA) ES+ 519, 521. |
| 39 | LCMS: (FA) ES+ 455, 457. |
| 40 | LCMS: (FA) ES+ 495, 497. |
| 42 | LCMS: (FA) ES+ 484, 486. |
| 43 | LCMS: (FA) ES+ 416, 418. |
| 46 | LCMS: (FA) ES+ 518, 520. |
| 47 | LCMS: (FA) ES+ 492, 494. |
| 48 | LCMS: (FA) ES+ 485, 487. |
| 50 | LCMS: (FA) ES+ 518, 520. |
| 51 | LCMS: (FA) ES+ 485, 487. |
| 52 | LCMS: (FA) ES+ 470, 472. |
| 53 | LCMS: (FA) ES+ 456, 458. |
| 54 | LCMS: (FA) ES+ 471, 473. |
| 60 | LCMS: (FA) ES+ 389, 391. |

Example 2

Synthesis of 4-(2,4-dichlorophenyl)-2-(2-(methylamino)pyridin-4-yl)-5-(4H-1,2,4-triazol-3-yl)thiophene-3-carbonitrile (Compound 37)

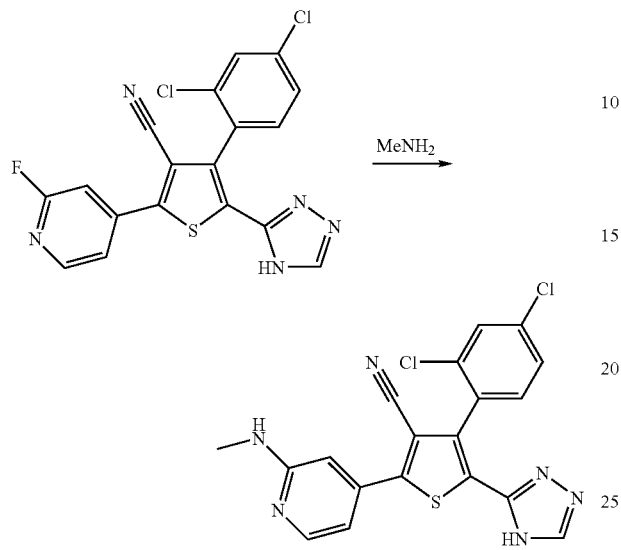

A solution of 4-(2,4-dichlorophenyl)-2-(2-fluoropyridin-4-yl)-5-(4H-1,2,4-triazol-3-yl)thiophene-3-carbonitrile (0.100 g, 0.000240 mol) and 1M Methylamine in methanol (4 mL, 0.004 mol) 0.000163 mol) was heated at 80° C. for 5 hours. The solvent was removed and the residue was purified using a silica gel chromatography (12 g), elution DCM to 5% MeOH in DCM over 20 minutes to afford the title compound (0.045 g, 44%). LCMS: (FA) ES+, 427, 429. $^1$H NMR (400 MHz, $d_4$-Methanol) δ 8.38 (s, 1H), 8.12-8.07 (m, 1H), 7.60 (dd, J=1.56, 0.77 Hz, 1H), 7.44-7.42 (m, 2H), 6.94 (dd, J=4.67, 1.66 Hz, 1H), 6.93 (s, 1H), 2.92 (s, 3H).

Compounds in the following table were prepared from the appropriate starting materials in a method analogous to that of Example 2:

| | |
|---|---|
| 14 | LCMS: (FA) ES+ 471, 473. |
| 23 | LCMS: (FA) ES+ 457, 459. |
| 33 | LCMS: (FA) ES+ 563, 565. |
| 35 | LCMS: (FA) ES+ 485, 487. |

Example 3

Synthesis of tert-butyl 4-(3-cyano-4-(2,4-dichlorophenyl)-5-(4H-1,2,4-triazol-3-yl)thiophen-2-yl)pyridin-2-ylcarbamate (Compound 26)

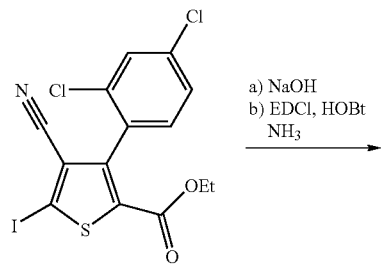

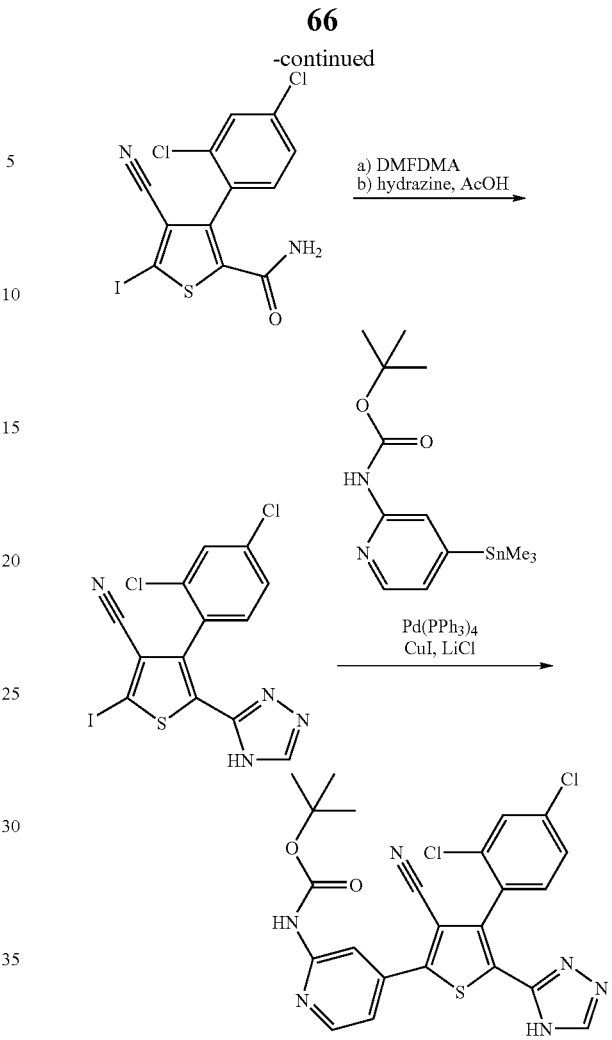

Step 1: 4-cyano-3-(2,4-dichlorophenyl)-5-iodothiophene-2-carboxylic acid

To a solution of ethyl 4-cyano-3-(2,4-dichlorophenyl)-5-iodothiophene-2-carboxylate (1.44 g, 0.00318 mol) in tetrahydrofuran (20 mL) and water (10 mL) was added a solution of 1.00M sodium hydroxide in water (16 mL). The solution was allowed to stir overnight. The reaction was quenched with a solution of 1N HCl (18 mL) and extracted with ethyl acetate. The organic extracts were washed with brine, dried over anhydrous sodium sulfate, filtered and concentrated in vacuo to afford the crude title compound (1.50 g, 100%) used directly in the next reaction. LCMS: (FA) ES−, 422. $^1$H NMR (400 MHz, $d_6$-DMSO) δ: 7.68 (d, 1H, J=2.0 Hz), 7.46-7.34 (m, 2H).

Step 2: 4-cyano-3-(2,4-dichlorophenyl)-5-iodothiophene-2-carboxylamide 4-cyano-3-(2,4-dichlorophenyl)-5-iodothiophene-2-carboxylic acid (1.30 g, 0.00306 mol) was dissolved in dichloromethane (30 mL). N-(3-dimethylaminopropyl)-N'-ethylcarbodiimide hydrochloride (1.27 g, 0.00661 mol) and 1-hydroxybenzotriazole (0.880 g, 0.00651 mol) were added to the solution and the reaction was stirred for 30 minutes. Ammonium hydroxide (5.97 mL, 30% aqueous solution, 0.153 mol) was added to the solution and the biphasic mixture was stirred for 2 hours. The reaction mixture was concentrated, diluted with water and extracted with ethyl acetate.

The organic extract was dried over anhydrous magnesium sulfate, filtered and column chromatography was performed to yield the title compound (1.21 g, 89%). LCMS: (FA) ES+, 423. ¹H NMR (400 MHz, d₆-DMSO) δ: 7.79 (d, 1H, J=2.0 Hz), 7.68 (bs, 1H), 7.57-7.45 (m, 2H), 7.30 (bs, 1H).

Step 3: 4-(2,4-dichlorophenyl)-2-iodo-5-(4H-1,2,4-triazol-3-yl)thiophene-3-carbonitrile A mixture of 4-cyano-3-(2,4-dichlorophenyl)-5-iodothiophene-2-carboxylamide (1.33 g, 0.00314 mol) and 1,1-dimethoxy-N,N-dimethylmethanamine (10.0 mL, 0.0753 mol) was irradiated in the microwave at 120° C. (300 watts) for 30 minutes. The reaction was concentrated in vacuo. The residue dissolved in acetic acid (1.0 mL, 0.18 mol) and hydrazine hydrate (0.69 mL, 0.014 mol) and subjected to microwave irradiation at 120° C. (300 watts) for 15 minutes. The solvent was removed in vacuo and the residue was azeotroped with toluene. Column chromatography was performed to yield the title compound (1.25 g, 85%). LCMS: (FA) ES+, 447. ¹H NMR (400 MHz, d₄-methanol) δ: 8.35 (s, 1H) 7.60 (d, 1H, J=2.0 Hz), 7.45-7.35 (m, 2H).

Step 4: tert-butyl 4-(3-cyano-4-(2,4-dichlorophenyl)-5-(4H-1,2,4-triazol-3-yl)thiophen-2-yl)pyridin-2-ylcarbamate A mixture of 4-(2,4-dichlorophenyl)-2-iodo-5-(4H-1,2,4-triazol-3-yl)thiophene-3-carbonitrile (0.180 g, 0.0004 mol), tert-butyl[4-(trimethylstannyl)pyridin-2-yl]carbamate (0.285 g, 0.0008 mol), lithium chloride (0.051 g, 0.0012 mol), copper(I) iodide (0.023 g, 0.00012 mol), tetrakis(triphenylphosphine)palladium (0.046 g, 0.00004 mol) was dissolved in dioxane (20 mL) and heated to reflux for 3 hours under an atmosphere of argon. The solvent was removed and the residue was purified using ISCO chromatography on silica gel, elution 20% ethyl acetate in hexanes to ethyl acetate to afford the title compound (0.270 g, 40%). LCMS: (FA) ES+, 513, 515. ¹H NMR (400 MHz, d₄-methanol) δ: 8.39 (s, 1H), 8.38 (d, J=6.31 Hz, 1H), 8.23 (s, 1H), 7.55-7.50 (m, 1H), 7.47 (dd, J=5.28, 1.56 Hz, 1H), 7.39-7.35 (m, 2H), 1.54 (s, 9H).

Compounds in the following table were prepared from the appropriate starting materials in a method analogous to that of Example 3:

| | |
|---|---|
| 10 | LCMS: (FA) ES+ 473, 475. |
| 44 | LCMS: (FA) ES+ 455, 457. |
| 59 | LCMS: (FA) ES+ 390, 392. |

Example 4

Synthesis 4-(2,4-dichlorophenyl)-2-[2-(methylamino)pyrimidin-4-yl]-5-(4H-1,2,4-triazol-3-yl)thiophene-3-carbonitrile (Compound 12)

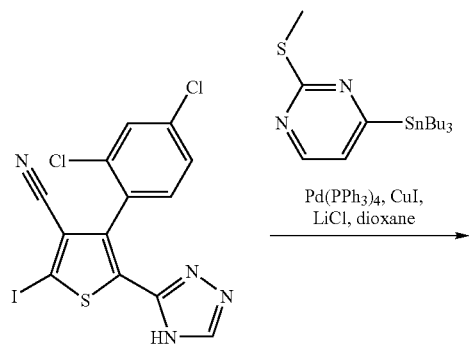

Step 1: 4-(2,4-dichlorophenyl)-2-[2-(methylsulfanyl)pyrimidin-4-yl]-5-(4H-1,2,4-triazol-3-yl)thiophene-3-carbonitrile 4-(2,4-dichlorophenyl)-2-iodo-5-(4H-1,2,4-triazol-3-yl)thiophene-3-carbonitrile (0.140 g, 0.313 mmol), Lithium chloride (0.0398 g, 0.939 mmol), Copper(I) iodide (0.0179 g, 0.0939 mmol), and Tetrakis(triphenylphosphine)palladium (0) (0.0362 g, 0.0313 mmol) were combined in a 100 mL round-bottom flask under an atmosphere of Argon. 1,4-Dioxane (8.75 mL, 0.112 mol) was added followed by 4-tributylstannyl-2-thiomethylpyrimidine (0.194 g, 0.470 mmol). The solution was heated to reflux for 2 hours. The solvent was concentrated in vacuo and the residue was purified using ISCO chromatography on silica gel, elution 20% ethyl acetate in hexanes to ethyl acetate to afford the title compound (0.066 g, 47%). LCMS: (FA) ES+, 445, 447. ¹H NMR (400 MHz, d₁-chloroform) δ: 8.67 (d, J=5.21 Hz, 1H), 8.21 (s, 1H), 7.86 (d, J=5.20 Hz, 1H), 7.60-7.55 (m, 1H), 7.44-7.34 (m, 2H), 2.66 (s, 3H).

Step 2: 4-(2,4-dichlorophenyl)-2-[2-(methylsulfonyl)pyrimidin-4-yl]-5-(4H-1,2,4-triazol-3-yl)thiophene-3-carbonitrile 4-(2,4-dichlorophenyl)-2-[2-(methylsulfanyl)pyrimidin-4-yl]-5-(4H-1,2,4-triazol-3-yl)thiophene-3-carbonitrile

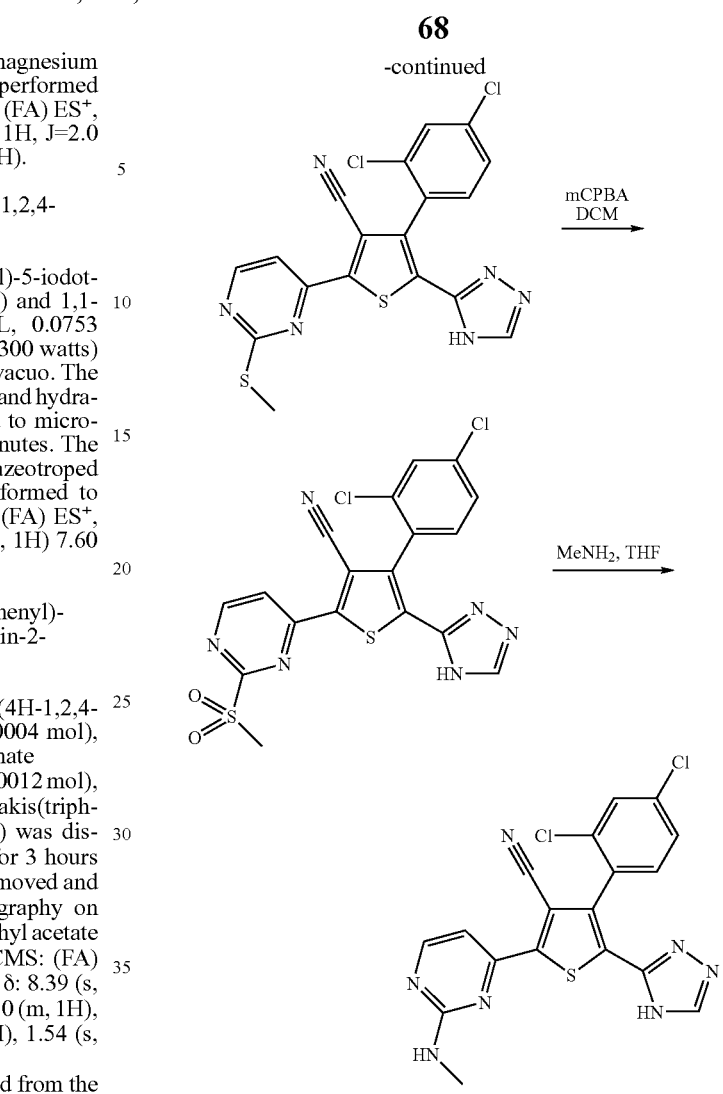

(0.0660 g, 0.148 mmol) was dissolved in Methylene chloride (5.5 mL, 0.086 mol) and Tetrahydrofuran (3.3 mL, 0.041 mol) and m-Chloroperbenzoic acid (0.0996 g, 0.444 mmol) was added. The mixture was stirred at room temperature for 4 hours. The solvent was concentrated in vacuo and the residue was purified using ISCO chromatography on silica gel, elution 40% ethyl acetate in hexanes to ethyl acetate to afford the title compound (0.047 g, 66%). LCMS: (FA) ES+, 477, 479. $^1$H NMR (400 MHz, $d_1$-chloroform) δ: 10.75 (bs, 1H), 9.08 (d, J=5.32 Hz, 1H), 8.35 (d, J=5.32 Hz, 1H), 8.25 (s, 1H), 7.59 (d, J=1.94 Hz, 1H), 7.42 (dd, J=8.22, 2.00 Hz, 1H), 7.36 (d, J=8.22 Hz, 1H), 3.48 (s, 3H).

Step 3: 4-(2,4-dichlorophenyl)-2-[2-(methylamino)pyrimidin-4-yl]-5-(4H-1,2,4-triazol-3-yl)thiophene-3-carbonitrile 4-(2,4-dichlorophenyl)-2-[2-(methylsulfonyl)pyrimidin-4-yl]-5-(4H-1,2,4-triazol-3-yl)thiophene-3-carbonitrile (0.047 g, 0.10 mmol) was dissolved in 2.0 M of Methylamine in Tetrahydrofuran (1.74 mL, 0.00349 mol) and the mixture was stirred at room temperature for 1 hour. The solvent was concentrated in vacuo and the residue was purified using ISCO chromatography on silica gel, elution 30% ethyl acetate in hexanes to ethyl acetate to afford the title compound (0.037 g, 81%). LCMS: (FA) ES+, 428, 430. $^1$H NMR (400 MHz, $d_4$-methanol) δ: 8.07-8.01 (m, 1H), 7.99 (s, 1H), 7.24-7.21 (m, 1H), 7.09-7.02 (m, 2H), 6.97 (d, J=5.04 Hz, 1H), 2.62 (s, 3H).

Compounds in the following table were prepared from the appropriate starting materials in a method analogous to that of Example 4:

| | |
|---|---|
| 7 | LCMS: (FA) ES+ 448, 450. |
| 8 | LCMS: (FA) ES+ 428, 430. |
| 21 | LCMS: (FA) ES+ 462, 464. |
| 22 | LCMS: (FA) ES+ 486, 488. |
| 27 | LCMS: (FA) ES+ 472, 474. |
| 36 | LCMS: (FA) ES+ 390, 392. |
| 41 | LCMS: (FA) ES+ 414, 416. |
| 49 | LCMS: (FA) ES+ 458, 460. |
| 55 | LCMS: (FA) ES+ 442, 444. |
| 58 | LCMS: (FA) ES+ 472, 474. |

Example 5

N-{4-[3-cyano-4-(2,4-dichlorophenyl)-5-(1H-imidazol-2-yl)-2-thienyl]pyridin-2-yl}cyclopropanecarboxamide (Compound 34)

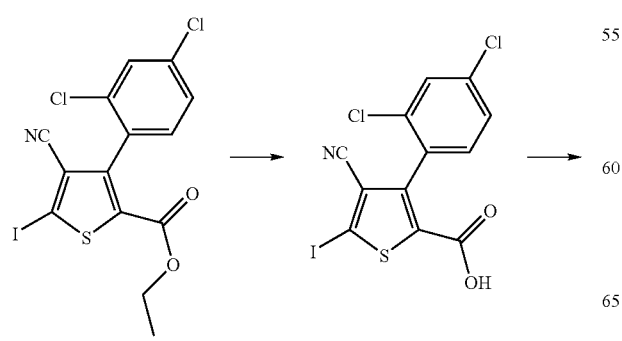

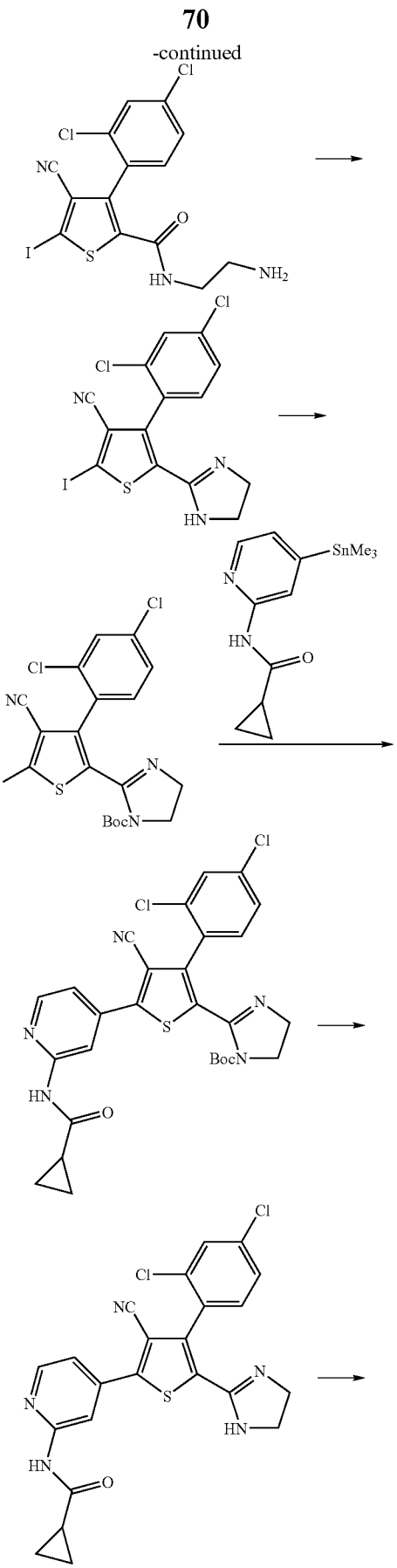

-continued

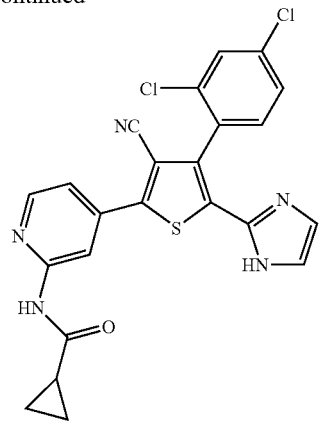

Step 1: 4-cyano-3-(2,4-dichlorophenyl)-5-iodothiophene-2-carboxylic acid

To a solution of ethyl 4-cyano-3-(2,4-dichlorophenyl)-5-iodothiophene-2-carboxylate (1.26 g, 0.00279 mol) in Tetrahydrofuran (20 mL, 0.3 mol) was added water (9.2 mL, 0.51 mol) and 1M NaOH (19.5 mL, 0.0195 mol) and the solution was stirred at room temperature for 2 days. The mixture was acidified by 1M HCl (20 mL), extracted with EtOAc (3×100 mL). The organic extracts were combined, dried over Na2SO4, filtered and evaporated to afford the product (1.17 g, 99%). LCMS: (FA) ES+, 424, 426. $^1$H NMR (400 MHz, d$_1$-chloroform) δ: 7.62-7.60 (m, 1H) 7.45-7.41 (m, 1H), 7.36-7.33 (m, 1H).

Step 2: N-(2-aminoethyl)-4-cyano-3-(2,4-dichlorophenyl)-5-iodothiophene-2-carboxamide A mixture of 4-cyano-3-(2,4-dichlorophenyl)-5-iodothiophene-2-carboxylic acid (1.17 g, 0.00276 mol), N-(2-aminoethyl)(tert-butoxy)carboxamide (0.690 mL, 0.00414 mol), N-(3-Dimethylaminopropyl)-N'-ethylcarbodiimide hydrochloride (1.06 g, 0.00552 mol) and 1-Hydroxybenzotriazole (0.746 g, 0.00552 mol) in Methylene chloride (40 mL, 0.6 mol) was stirred at room temperature overnight. The mixture was washed with water (2×20 mL), dried with MgSO4, filtered and evaporated. The residue was purified using ISCO chromatography on silica gel, elution 30% ethyl acetate in hexanes to ethyl acetate to afford the intermediate (1.40 g, 90%). LCMS: (FA) ES+, 566, 568. The Boc-protected material was dissolved in 1,4-Dioxane (40 mL, 0.5 mol), 4.00 M HCl in dioxane (8.00 mL, 0.032 mol) and the mixture was stirred at room temperature for 30 minutes. The solvent was evaporated to dryness and the residue was dissolved in DCM (100 mL). Sodium hydroxide (7.2 g, 0.18 mol) in 10 ml of water was added and the mixture was stirred vigorously for 10 minutes. Organic layer was separated and the aqueous phase was extracted twice with DCM. The combined DCM layers were dried with MgSO4, filtered and evaporated to afford the free base (1.16 g, 90%). LCMS: (FA) ES+, 466, 468. $^1$H NMR (400 MHz, d$_6$-DMSO) δ: 7.80-7.78 (m, 1H) 7.57-7.53 (m, 1H), 7.51-7.48 (m, 1H), 3.72-3.63 (m, 1H), 3.51-3.43 (m, 1H), 3.07-3.02 (m, 2H).

Step 3: 4-(2,4-dichlorophenyl)-5-(4,5-dihydro-1H-imidazol-2-yl)-2-iodothiophene-3-carbonitrile To a mixture of N-(2-aminoethyl)-4-cyano-3-(2,4-dichlorophenyl)-5-iodothiophene-2-carboxamide (1.16 g, 0.00249 mol) in Toluene (20 mL, 0.19 mol) in a pressure vessel was added Phosphoryl chloride (2.0 mL, 0.022 mol) and the mixture was heated at 120° C. for 3 hours. Solvent was evaporated and the residue was diluted with water, treated with 1N NaOH (10 mL) and extracted with DCM (5×50 mL). The combined DCM layers were washed with brine, dried with MgSO4, filtered and concentrated to afford the product (1.00 g, 89%). LCMS: (FA) ES+, 448, 450. $^1$H NMR (400 MHz, d$_6$-DMSO) δ: 7.81-7.78 (m, 1H) 7.56-7.52 (m, 1H), 7.50-7.47 (m, 1H), 3.67-3.59 (m, 2H), 3.25-3.17 (m, 2H).

Step 4: tert-butyl 2-[4-cyano-3-(2,4-dichlorophenyl)-5-iodo-2-thienyl]-4,5-dihydro-1H-imidazole-1-carboxylate To a solution of 4-(2,4-dichlorophenyl)-5-(4,5-dihydro-1H-imidazol-2-yl)-2-iodothiophene-3-carbonitrile (0.859 g, 1.92 mmol) in DCM (18.6 mL, 290 mmol) at 0° C. was added triethylamine (0.313 mL, 2.24 mmol) followed by di-tert-Butyldicarbonate (0.489 g, 2.24 mmol). The mixture was stirred at room temperature for 3 days. Water (10 mL) and DCM (100 mL) were added, organic layer was separated and the aqueous layer was extracted with DCM (2×50 mL). Combined organic layers were washed with saturated NaHCO3 (10 mL) and brine (20 mL), dried with MgSO4, filtered and evaporated. The residue was purified using ISCO chromatography on silica gel, elution 5 to 55% ethyl acetate in hexanes to afford the product (0.615 g, 58%). LCMS: (FA) ES+, 548, 550. $^1$H NMR (400 MHz, d$_6$-DMSO) δ: 7.78-7.76 (m, 1H) 7.55-7.51 (m, 1H), 7.35-7.31 (m, 1H), 3.77-3.63 (m, 4H), 1.24 (s, 9H).

Step 5: tert-butyl 2-[4-cyano-5-{2-[(cyclopropylcarbonyl)amino]pyridin-4-yl}-3-(2,4-dichlorophenyl)-2-thienyl]-4,5-dihydro-1H-imidazole-1-carboxylate tert-butyl 2-[4-cyano-3-(2,4-dichlorophenyl)-5-iodo-2-thienyl]-4,5-dihydro-1H-imidazole-1-carboxylate (0.500 g, 0.912 mmol), N-[4-(trimethylstannyl)pyridin-2-yl]cyclopropanecarboxamide (0.445 g, 1.37 mmol), Lithium chloride (0.116 g, 2.74 mmol), Copper(I) iodide (0.0521 g, 0.274 mmol) and Tetrakis(triphenylphosphine)palladium(0) (0.105 g, 0.0912 mmol) were combined in a 100 mL round-bottom flask under an atmosphere of argon and 1,4-Dioxane (45.3 mL, 0.580 mol) was added. The solution was heated to reflux for 2 hours. The reaction was concentrated in vacuo and the residue was purified using ISCO chromatography on silica gel, elution 10 to 70% ethyl acetate in hexanes to afford the product (0.315 g, 59%). LCMS: (FA) ES+, 582, 584. $^1$H NMR (400 MHz, d$_1$-chloroform) δ: 8.62-8.58 (m, 1H) 8.41-8.38 (m, 1H), 8.26 (s, 1H), 7.54-7.50 (m, 1H), 7.50-7.48 (m, 1H), 7.40-7.37 (m, 1H), 7.33-7.29 (m, 1H), 3.96-3.73 (m, 4H), 1.56-1.54 (m, 1H), 1.32 (s, 9H), 1.17-1.11 (m, 2H), 0.95-0.88 (m, 2H).

Step 6: N-{4-[3-cyano-4-(2,4-dichlorophenyl)-5-(4,5-dihydro-1H-imidazol-2-yl)-2-thienyl]pyridin-2-yl}cyclopropanecarboxamide To a solution of tert-butyl 2-[4-cyano-5-{2-[(cyclopropylcarbonyl)amino]pyridin-4-yl}-3-(2,4-dichlorophenyl)-2-thienyl]-4,5-dihydro-1H-imidazole-1-carboxylate (0.315 g, 0.541 mmol) in 1,4-Dioxane (4.00 mL, 51.2 mmol) was added 4.00 M of Hydrochloric acid in 1,4-Dioxane (1.35 mL, 5.41 mmol), stirred at room temperature overnight. Solvent was evaporated, residue was diluted with DCM (50 mL) and washed with 1M NaOH (5 mL). Layers were separated and the aqueous phase was extracted with DCM (3×50 mL). Combined organic extracts were dried with MgSO4, filtered and evaporated. The residue was purified using ISCO chromatography on silica gel, elution 5 to 80% ethyl acetate in hexanes to afford the product (0.197 g, 76%). LCMS: (FA)

ES+, 482, 484. ¹H NMR (400 MHz, d₁-chloroform) δ: 8.66-8.64 (m, 1H) 8.41-8.38 (m, 1H), 8.25 (s, 1H), 7.61-7.59 (m, 1H), 7.48-7.45 (m, 1H), 7.44-7.41 (m, 1H), 7.37-7.34 (m, 1H), 3.97-3.68 (m, 2H), 3.60-3.25 (m, 2H), 1.57-1.52 (m, 1H), 1.17-1.11 (m, 2H), 0.95-0.88 (m, 2H).

Step 7: N-{4-[3-cyano-4-(2,4-dichlorophenyl)-5-(1H-imidazol-2-yl)-2-thienyl]pyridin-2-yl}cyclopropanecarboxamide A mixture of N-{4-[3-cyano-4-(2,4-dichlorophenyl)-5-(4,5-dihydro-1H-imidazol-2-yl)-2-thienyl]pyridin-2-yl}cyclopropanecarboxamide (0.0650 g, 0.135 mmol) and Magtrieve (0.143 g, 1.70 mmol) was taken up in toluene (5 mL) and heated at 120° C. for 4 hours. The mixture was cooled to room temperature, diluted with DCM (10 mL) and filtered through a pad of celite. The solid residue was washed with 1% ammonia, 9% methanol in DCM mixture (10 mL) and solvent from the filtrate was evaporated. The residue was purified using ISCO chromatography on silica gel, elution 10 to 70% ethyl acetate in hexanes to afford the product (0.027 g, 47%). LCMS: (FA) ES+, 480, 482. ¹H NMR (400 MHz, d₆-DMSO) δ: 11.88 (s, 1H) 11.11 (m, 1H), 8.57-8.55 (m, 1H), 8.53-8.50 (m, 1H), 7.85-7.84 (m, 1H), 7.58-7.56 (m, 2H), 7.54-7.52 (m, 1H), 7.17-7.16 (m, 1H), 7.00-6.98 (m, 1H), 2.08-2.00 (m, 1H), 0.87-0.81 (m, 4H).

Compounds in the following table were prepared from the appropriate starting materials in a method analogous to that of Example 5:

| | |
|---|---|
| 5 | LCMS: (FA) ES+ 412, 414. |
| 13 | LCMS: (AA) ES+495, 497. |
| 16 | LCMS: (FA) ES+ 427, 429. |
| 31 | LCMS: (FA) ES+ 512, 514. |
| 45 | LCMS: (FA) ES+ 426, 428. |
| 56 | LCMS: (FA) ES+ 440, 442. |
| 57 | LCMS: (FA) ES+ 454, 456. |
| 61 | LCMS: (FA) ES+ 469, 471. |
| 63 | LCMS: (FA) ES+ 496, 498. |
| 86 | LCMS: (FA) ES+ 470, 472. |
| 87 | LCMS: (FA) ES+ 482, 484. |

Example 6

Synthesis N-{4-[5-(1-benzyl-1H-imidazol-2-yl)-3-cyano-4-(2,4-dichlorophenyl)-2-thienyl]pyridin-2-yl}acetamide (Compound 19)

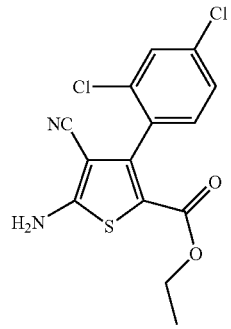
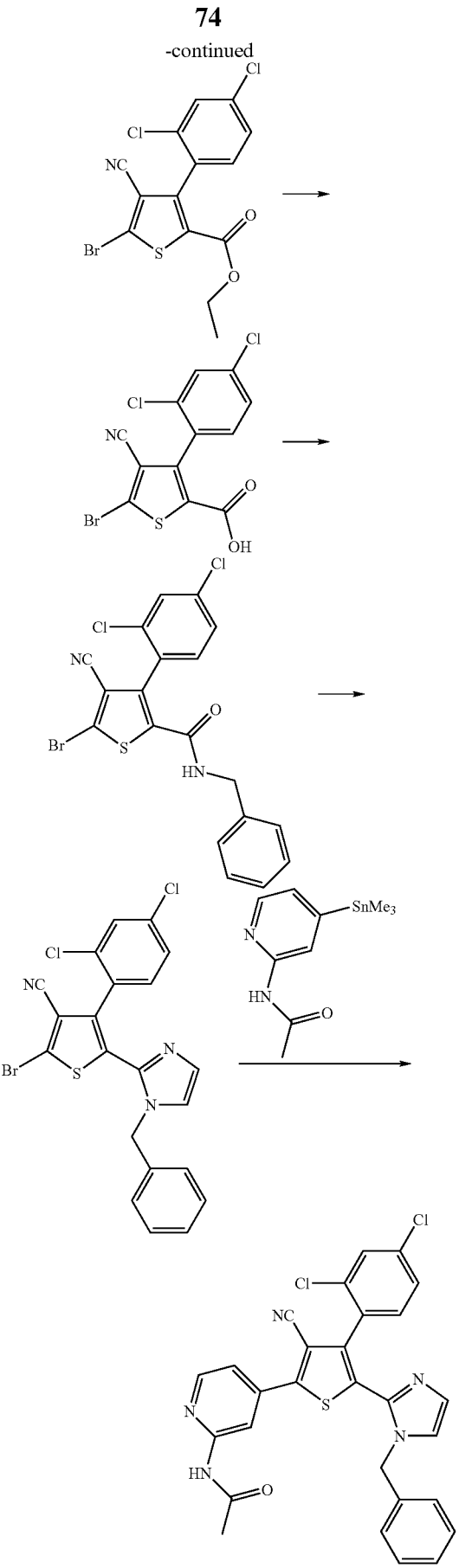

Step 1: Ethyl 5-bromo-4-cyano-3-(2,4-dichlorophenyl)thiophene-2-carboxylate

Copper(II) Bromide (9.75 g, 0.0437 mol) was dissolved in acetonitrile (194 mL, 3.72 mol). To this solution was added tert-Butyl nitrite (6.97 mL, 0.0586 mol) slowly while warming to 50° C. Heating at 50° C. was continued for 30 minutes and a solution of ethyl 5-amino-4-cyano-3-(2,4-dichlorophenyl)thiophene-2-carboxylate (10.0 g, 0.0293 mol) in acetonitrile (260 mL, 5.1 mol) was added. The reaction mixture was heated at 80° C. for 30 minutes. Solvent was concentrated in vacuo and the residue was purified using ISCO chromatography on silica gel, solid load, elution with hexanes to 25% EA in hexanes over 30 minutes to give the product (8.8 g, 74%). LCMS: (FA) ES$^+$, 404, 406, 408. $^1$H NMR (400 MHz, d$_1$-chloroform) δ: 7.53 (d, J=2.01 Hz, 1H), 7.37 (dd, J=8.27, 2.03 Hz, 1H), 7.22 (d, J=8.27 Hz, 1H), 4.21 (dq, J=7.14, 7.10, 7.10, 3.46 Hz, 2H), 1.19 (t, J=7.13, 7.13 Hz, 3H).

Step 2: 5-bromo-4-cyano-3-(2,4-dichlorophenyl)thiophene-2-carboxylic acid

Ethyl 5-bromo-4-cyano-3-(2,4-dichlorophenyl)thiophene-2-carboxylate (4.60 g, 0.0114 mol) was dissolved in Tetrahydrofuran (100 mL) and Water (20 mL) and 1.00 M of Sodium hydroxide in Water (34.1 mL, 0.0341 mol) was added The mixture was stirred at room temperature overnight. Reaction was quenched by addition of 1N HCl (36 mL), extracted with EA (3×), dried MgSO4, filtered and evaporated to give the product that was used without further purification (4.28 g, 100%). LCMS: (FA) ES$^-$, 374, 376, 378. $^1$H NMR (400 MHz, d$_1$-chloroform) δ: 7.52 (d, J=1.99 Hz, 1H), 7.35 (dd, J=8.28, 2.02 Hz, 1H), 7.21 (d, J=8.27 Hz, 1H).

Step 3: N-benzyl-5-bromo-4-cyano-3-(2,4-dichlorophenyl)thiophene-2-carboxamide 5-bromo-4-cyano-3-(2,4-dichlorophenyl)thiophene-2-carboxylic acid (0.623 g, 1.65 mmol), 1-Hydroxybenzotriazole hydrate (0.253 g, 1.65 mmol) and N-(3-Dimethylaminopropyl)-N'-ethylcarbodiimide hydrochloride (0.570 g, 2.97 mmol) were taken up in DCM (30 mL) and the mixture was stirred for 5 minutes at room temperature. N,N-Diisopropylethylamine (0.460 mL, 2.64 mmol) was added followed by benzylamine (0.216 mL, 1.98 mmol) and the solution was stirred at room temperature overnight. The mixture was quenched with water, extracted with DCM (3×50 mL), washed with water, brine, dried over Na$_2$SO$_4$, filtered and evaporated. The residue was purified using ISCO chromatography on silica gel, elution with 10-25% EA in hexanes to give the product (0.574 g, 74%). LCMS: (FA) ES$^+$, 465, 467, 469. $^1$H NMR (400 MHz, d$_1$-chloroform) δ: 7.46 (d, J=2.00 Hz, 1H), 7.32-7.27 (m, 4H), 7.26-7.23 (d, J=7.78 Hz, 1H), 6.99-6.96 (m, 2H), 5.38 (bs, 1H), 4.36 (d, J=5.52 Hz, 2H).

Step 4: 5-(1-benzyl-1H-imidazol-2-yl)-2-bromo-4-(2,4-dichlorophenyl)thiophene-3-carbonitrile N-benzyl-5-bromo-4-cyano-3-(2,4-dichlorophenyl)thiophene-2-carboxamide (0.180 g, 0.386 mmol) was dissolved in DCM (2 mL) and phosphorus pentachloride (0.0884 g, 0.425 mmol) and 4.00 M of Hydrochloric acid in 1,4-dioxane (0.050 mL, 0.20 mmol) were added. The mixture was heated in a sealed vial at 60° C. for 2 hours. After cooling down to room temperature, aminoacetaldehyde dimethyl acetal (0.252 mL, 2.32 mmol) was slowly added. The mixture was heated at 60° C. for additional 1 hour. After cooling to room temperature, 4.00 M of Hydrochloric acid in 1,4-dioxane (1.0 mL, 4.0 mmol) was added and the mixture was heated at 60° C. for 2 hours and at room temperature overnight. Solvent was concentrated and the residue was diluted with EA, washed with saturated NaHCO$_3$, brine, dried with Na$_2$SO$_4$, filtered and evaporated. The residue was purified using ISCO chromatography on silica gel, elution with 10-25% EA in hexanes to give the product (0.110 g, 58%). LCMS: (FA) ES$^+$, 488, 490, 492. $^1$H NMR (300 MHz, d$_1$-chloroform) δ: 7.28 (d, J=2.07 Hz, 1H), 7.26-7.15 (m, 5H), 7.11-7.08 (d, J=8.29 Hz, 1H), 6.85 (s, 1H), 6.73-6.70 (dd, J=6.97 Hz, 1.66 Hz, 2H). 4.85-4.70 (m, 2H).

Step 5: N-{4-[5-(1-benzyl-1H-imidazol-2-yl)-3-cyano-4-(2,4-dichlorophenyl)-2-thienyl]pyridin-2-yl}acetamide 5-(1-benzyl-1H-imidazol-2-yl)-2-bromo-4-(2,4-dichlorophenyl)thiophene-3-carbonitrile (107 mg, 0.219 mmol), N-[4-(trimethylstannyl)pyridin-2-yl]acetamide (85.0 mg, 0.284 mmol), Lithium chloride (30.0 mg, 0.708 mmol), Copper(I) iodide (4.70 mg, 0.0247 mmol) and Tetrakis(triphenylphosphine)palladium(0) (24.7 mg, 0.0214 mmol) were taken up in 1,4-Dioxane (3.0 mL) under an atmosphere of argon. The mixture was heated at 90° C. for 4 hours. The solvent was evaporated and the residue was purified using ISCO chromatography on silica gel, elution with 1-2% MeOH in DCM to give the product (0.071 g, 60%). LCMS: (FA) ES$^+$544, 546. $^1$H NMR (400 MHz, d$_1$-chloroform) δ: 8.59 (s, 1H), 8.40 (d, J=5.27 Hz, 1H), 8.03 (s, 1H), 7.52 (dd, J=5.27 Hz, 1.76 Hz, 1H), 7.30 (d, J=2.00 Hz, 1H), 7.27-7.16 (m, 6H), 6.87 (d, 1H), 6.77-6.75 (d, J=6.27 Hz, 2H), 4.90-4.78 (m, 2H), 2.25 (s, 3H)

Example 7

Synthesis of N-{4-[4-(2,4-dichlorophenyl)-5-(1H-imidazol-2-yl)-2-thienyl]pyridin-2-yl}acetamide (62)

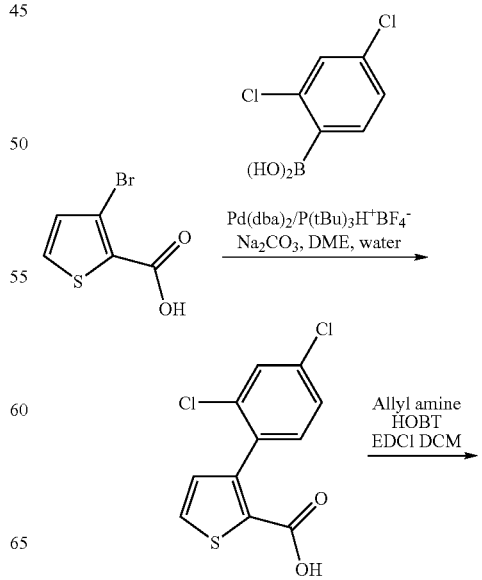

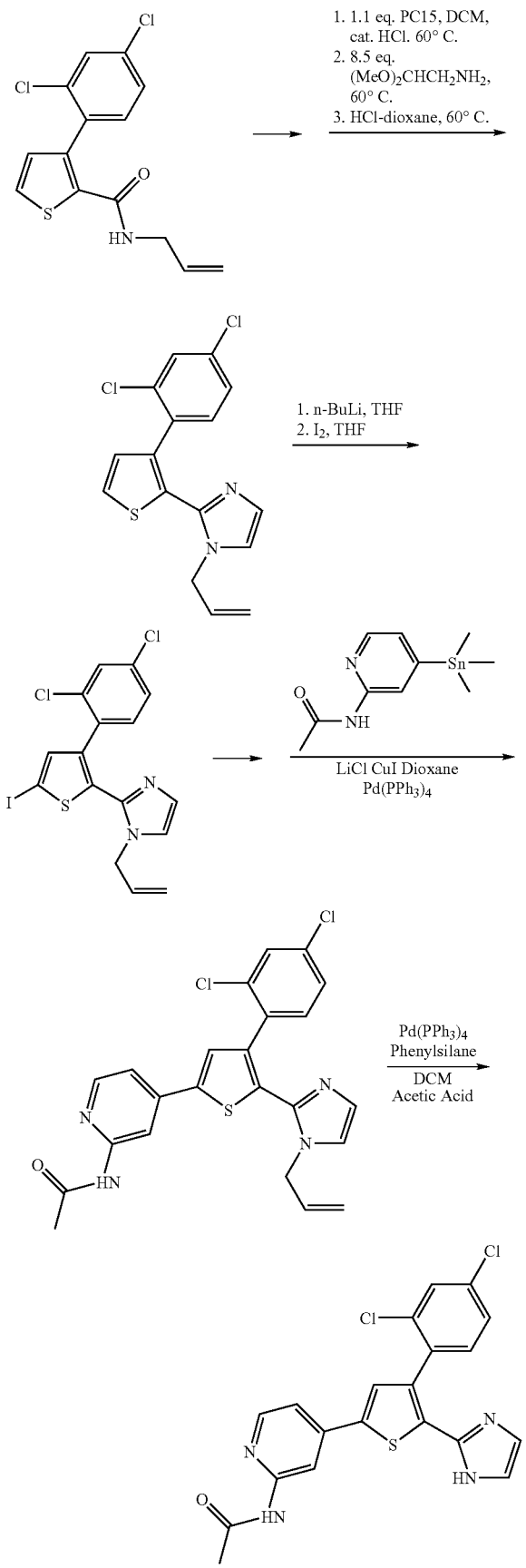

Step 1, Preparation of 3-(2,4-dichlorophenyl)thiophene-2-carboxylic acid

To a solution of tris(dibenzylideneacetone)dipalladium (1.33 g, 1.45 mmol) and tri-tert-butylphosphonium tetrafluoroborate (0.84 g, 2.90 mmol) in 1,2-dimethoxyethane (247 mL) was added water (83.5 mL) then the mixture was sonicated for 10 min under an atmosphere of Argon. To the mixture was added sodium carbonate (18.4 g, 174 mmol), 2,4-dichlorophenylboronic acid (22.1 g, 116 mmol) and 3-bromothiophene-2-carboxylic acid (12.0 g, 58.0 mmol) at room temperature. The resulting mixture was stirred for 30 min at 80° C. After cooling to room temperature, the reaction mixture was filtered through a Celite pad and the solid residue was washed with EtOAc (200 mL) and water (200 mL). The filtrate was evaporated to remove organic solvents and the remaining aqueous solution was basified with 1 N NaOH solution (300 mL) and diluted with water (300 mL). This layer was washed with DCM (3×300 mL). The combined DCM layers were extracted with 0.5 N NaOH (400 mL). All aqueous layers were combined, acidified by addition of conc HCl until pH 1~2 and the resulting suspension was extracted with EtOAc (4×800 mL). The combined organic layers were washed with brine, dried over $Na_2SO_4$, filtered, and concentrated in vacuo. The resulting colored solid was washed with EtOAc and DCM to give 10.2 g of product as an off white solid. The washings were concentrated in vacuo and were subjected to column chromatography ($SiO_2$, elution with 0-15% EtOAc in DCM) to provide additional 3.5 g of product. Solids were combined to give 13.7 g of title compound. (82% yield). LC/MS (FA) ES+ 225. $^1$H NMR (400 MHz, $d_6$-DMSO) δ: 12.97 (br s, 1H), 7.91 (d, J=5.3 Hz, 1H), 7.68 (d, J=2.2 Hz, 1H), 7.44 (dd, J=2.2, 8.3 Hz, 1H), 7.37 (d, J=8.3 Hz, 1H), 7.10 (d, J=5.3 Hz, 1H).

Step 2, Preparation of N-allyl-3-(2,4-dichlorophenyl) thiophene-2-carboxamide To a stirred solution of 3-(2,4-dichlorophenyl)thiophene-2-carboxylic acid (9.65 g, 35.3 mmol) in DCM (290 mL) was added HOBT (4.77 g, 35.3 mmol) and EDCI (10.8 g, 56.5 mmol) at room temperature and the mixture was stirred for 30 min. To the solution was added 2-propen-1-amine (10.6 mL, 141 mmol) then the resulting mixture was stirred for 5 hrs. The reaction mixture was evaporated and saturated $NH_4Cl$ (200 mL) was added to the residue. The mixture was extracted with EtOAc (200 mL×3). The combined organic layers were washed with brine, dried over $Na_2SO_4$, filtered, and concentrated in vacuo. The residue was purified by column chromatography ($SiO_2$, elution with 20% EtOAc in hexanes) to give 11.3 g of product (2) (91% yield). LC/MS (FA) ES+ 314. $^1$H NMR (400 MHz, $d_6$-DMSO) δ: 7.96-8.07 (br t, J=5.5 Hz, 1H), 7.75 (d, J=5.0 Hz, 1H), 7.66 (d, J=2.3 Hz, 1H), 7.45 (dd, J=2.3, 8.3 Hz, 1H), 7.36 (d, J=8.3 Hz, 1H), 7.08 (d, J=5.0 Hz, 1H), 5.69-5.80 (m, 1H), 4.98-5.06 (m, 2H), 3.68-3.74 (m, 2H).

Step 3, Preparation of 1-allyl-2-[3-(2,4-dichlorophenyl)-2-thienyl]-1H-imidazole To a solution of N-allyl-3-(2,4-dichlorophenyl)thiophene-2-carboxamide (8.60 g, 27.5 mmol) in DCM (309 mL, 4820 mmol) was added phosphorus pentachloride (6.54 g, 31.4 mmol) and 4 M hydrochloric acid in 1,4-dioxane (0.51 mL, 2.00 mmol) and the mixture was heated to 60° C. for 2 hrs. The reaction was cooled to room temperature and aminoacetaldehyde dimethyl acetal (33.9 mL, 311 mmol) was slowly added. The resulting mixture was heated at 60° C. for 2.5 hrs. To the reaction mixture was added 4 M hydrochloric acid in 1,4-dioxane (200 mL, 783 mmol) and the mixture was stirred at 60° C. overnight. After cooling to room temperature, the suspension was filtered through a Celite pad and the solid residue was washed with 1,4-dioxane. The filtrate was evaporated down and the resulting residue was dissolved in water (300 mL) and extracted with EtOAc (2×150 mL). The water layer was basified by addition of solid NaHCO$_3$ until pH 9, and the aqueous was extracted with EtOAc (3×300 mL). All organics were combined and dried over Na$_2$SO$_4$, filtered, and concentrated in vacuo. The residue was purified by column chromatography (SiO$_2$, elution with 8-25% EtOAc in DCM) to give crude product which was further purified by column chromatography (SiO$_2$, elution with 45% MeCN: 50% DCM: 5% EtOAc) to provide 7.12 g of product (76%). LC/MS (FA), ES+ 337. $^1$H NMR (400 MHz, d$_6$ DMSO) δ: 7.80 (d, J=5.3 Hz, 1H,), 7.68 (d, J=2.0 Hz, 1H), 7.35 (dd, J=2.0, 8.3 Hz, 1H), 7.26 (d, J=5.3 Hz, 1H), 7.13 (d, J=1.3 Hz, 1H), 7.08 (d, J=8.3 Hz, 1H), 6.98 (d, J=1.3 Hz, 1H), 5.47-5.58 (m, 1H), 4.98-5.02 (m, 1H), 4.75-4.82 (m, 1H), 4.19-4.23 (m, 2H).

Step 4, Preparation of 1-allyl-2-[3-(2,4-dichlorophenyl)-5-iodo-2-thienyl]-1H-imidazole To a solution of 1-allyl-2-[3-(2,4-dichlorophenyl)-2-thienyl]-1H-imidazole (2.50 g, 7.46 mmol) in THF (80.0 mL) cooled to −78° C. was added dropwise 2.50 M of n-butyl-lithium in hexane (3.28 mL, 8.20 mmol) and the mixture was stirred for 30 min. To the solution was added dropwise a solution of iodine (2.84 g, 11.2 mmol) in THF (10.0 mL) and the resulting solution was stirred for 15 min at −78° C. The reaction mixture was quenched by addition of saturated sodium bisulfite solution (200 mL) and the resulting mixture was warmed to room temperature while stirring for 30 min. The mixture was extracted with EtOAc (3×250 mL) and the combined organic layers were washed with brine (200 mL). The organic layer was dried over Na$_2$SO$_4$, filtered, and concentrated in vacuo. The residue was purified by column chromatography (SiO$_2$, elution with 1-6% EtOAc in hexane) to give crude product which was further purified by column chromatography (SiO$_2$, elution with 2% MeOH in DCM) to provide 2.57 g of product (71%). LC/MS (FA), ES+ 462. $^1$H NMR (400 MHz, d$_6$-DMSO) δ: 7.30 (d, J=2.2 Hz, 1H), 7.09 (s, 1H), 6.97 (dd, J=2.2, 8:2 Hz, 1H), 6.75 (d, J=1.3 Hz, 1H), 6.71 (d, J=8.2 Hz, 1H), 6.60 (d, J=1.3 Hz, 1H), 5.10-5.21 (m, 1H), 4.60-4.65 (m, 1H), 4.35-4.41 (m, 1H), 3.80-3.85 (m, 2H).

Step 5, Preparation of N-{4-[5-(1-allyl-1H-imidazol-2-yl)-4-(2,4-dichlorophenyl)-2-thienyl]pyridin-2-yl}acetamide 1-allyl-2-[3-(2,4-dichlorophenyl)-5-iodo-2-thienyl]-1H-imidazole (4) (2.00 g, 4.34 mmol), N-[4-(trimethylstannyl)pyridin-2-yl]acetamide (2.59 g, 8.67 mmol), tetrakis(triphenylphosphine)palladium (0.25 g, 0.22 mmol), CuI (0.25 g, 1.30 mmol), and LiCl (0.55 g, 13.0 mmol) were weighed into a round bottom flask, equipped with reflux condenser, and the flask was purged with Argon. To this mixture was added 1,4-dioxane (100 mL) and the resulting suspension was stirred for 5 hrs at 90° C. The reaction was cooled to room temperature and concentrated in vacuo. To the solid residue was added EtOAc and DCM then the suspension was filtered through a Celite pad. The filtrate was concentrated in vacuo and the residue was purified by column chromatography (SiO$_2$, elution with 45% CH$_3$CN: 50 DCM: 5% MeOH) to give crude product which was further purified by column chromatography (SiO$_2$, elution with 4-7% MeOH in DCM) to provide 1.03 g of product (51%). LC/MS (FA) ES+ 471. $^1$H NMR (400 MHz, d$_6$-DMSO) δ: 10.6 (s, 1H), 8.39 (s, 1H), 8.36 (d, J=5.3 Hz, 1H), 7.86 (s, 1H), 7.73 (d, J=2.3 Hz, 1H), 7.49 (dd, J=1.8, 5.3 Hz, 1H), 7.42 (dd, J=2.2, 8.3 Hz, 1H), 7.19-7.23 (m, 2H), 7.03 (d, J=1.1 Hz, 1H), 5.54-5.65 (m, 1H), 5.02-5.07 (m, 1H), 4.79-4.86 (m, 1H), 4.28-4.32 (m, 2H), 2.12 (s, 3H).

Step 6, Preparation of N-{4-[4-(2,4-dichlorophenyl)-5-(1H-imidazol-2-yl)-2-thienyl]pyridin-2-yl}acetamide (62-A)

To a solution of N-{4-[5-(1-allyl-1H-imidazol-2-yl)-4-(2,4-dichlorophenyl)-2-thienyl]pyridin-2-yl}acetamide (750 mg, 1.60 mmol) and tetrakis(triphenylphosphine)palladium (92.0 mg, 0.08 mmol) in DCM (12.0 mL) was added acetic acid (3.95 mL, 69.5 mmol) and phenylsilane (1.00 mL, 8.15 mmol) and the mixture was stirred for 24 hrs at 40° C. The reaction mixture was evaporated to remove volatiles and DCM added. To this solution was added saturated NaHCO$_3$ and the resulting mixture was stirred for 30 min. The mixture was extracted with DCM (3×100 mL) and the combined DCM layers were washed with brine. The organics were dried over Na$_2$SO$_4$, filtered, and concentrated in vacuo. The residue was partially purified by column chromatography (SiO$_2$, elution with 3-6% MeOH in DCM) to give crude product which was further purified by column chromatography (SiO$_2$, elution with 100% EtOAc) to provide 589 mg of the product (84%). LC/MS (FA) ES+ 431. $^1$H NMR (400 MHz, d$_6$ DMSO) δ: 11.8-11.9 (br s, 1H), 10.6 (s, 1H), 8.39 (s, 1H), 8.32 (d, J=5.2 Hz, 1H), 7.71 (d, J=1.7 Hz, 1H), 7.69 (s, 1H), 7.45-7.49 (m, 2H), 7.42 (d, J=8.5 Hz, 1H), 6.90-7.15 (br s, 2H), 2.12 (s, 3H).

Compounds in the following table were prepared from the appropriate starting materials in a method analogous to that of Example 7:

| | |
|---|---|
| 64 | LCMS: (FA) ES+ 387, 389. |
| 65 | LCMS: (FA) ES+ 429, 431. |
| 68 | LCMS: (FA) ES+ 455, 457. |
| 69 | LCMS: (FA) ES+ 445, 447. |

Example 8

Synthesis of 4-[4-(2,4-dichlorophenyl)-5-(1H-imidazol-2-yl)-2-thienyl]-2-methylpyridine (66)

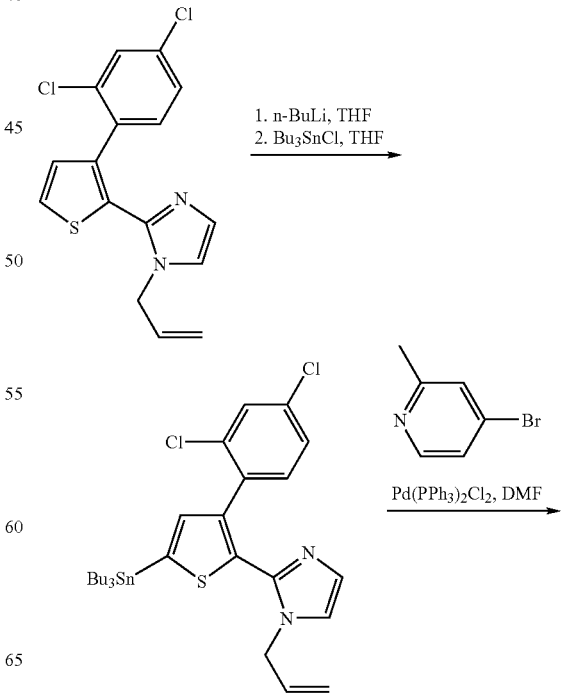

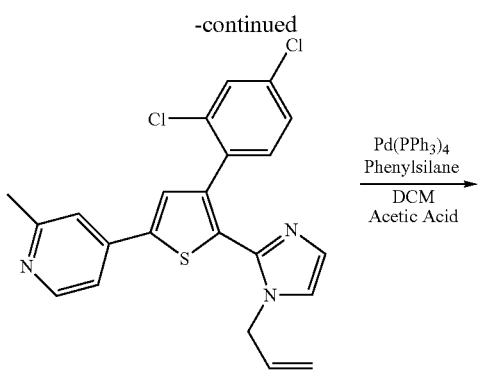

Step 1, Preparation of 1-allyl-2-[3-(2,4-dichlorophenyl)-5-(tributylstannyl)-2-thienyl]-1H-imidazole To a stirred solution of 1-allyl-2-[3-(2,4-dichlorophenyl)-2-thienyl]-1H-imidazole (3.40 g, 10.1 mmol) in THF (80 mL) was added dropwise 2.50 M of n-butyllithium in Hexane (4.46 mL, 11.2 mmol) at −78° C. and the resulting solution was stirred for 30 min. A solution of tributyltin chloride (3.44 mL, 12.7 mmol) in THF (40.0 mL) was added dropwise into the cold solution and then the resulting mixture was stirred for 1 hr at −78° C. The reaction mixture was quenched by addition of water (150 ml) and the resulting mixture was extracted with EtOAc (200 ml×3). The combined organic layers were washed with brine, dried using Na$_2$SO$_4$, filtered and concentrated in vacuo. The residue was purified by column chromatography (SiO$_2$, elution with 0-20% EtOAc in hexanes) to provide 3.5 g of product as a yellowish oil (71%). LC/MS (FA) ES+ 625. $^1$H NMR (400 MHz, d$_6$ DMSO) δ: 7.67 (d, J=2.0 Hz, 1H), 7.34 (dd, J=2.0, 8.3 Hz, 1H), 7.24 (t, J=10.5 Hz, 1H), 7.12 (d, J=1.2 Hz, 1H), 7.07 (d, J=8.3 Hz, 1H), 6.97 (d, J=1.2 Hz, 1H), 5.46-5.57 (m, 1H), 4.98 (dd, J=1.5, 10.2 Hz, 1H), 4.79 (dd, J=1.5, 17.1 Hz, 1H), 4.18-4.22 (m, 2H), 1.44-1.68 (m, 6H); 1.25-1.36 (m, 6H), 1.04-1.23 (m, 6H), 0.82-0.89 (m, 9H).

Step 2, Preparation of 4-[5-(1-allyl-1H-imidazol-2-yl)-4-(2,4-dichlorophenyl)-2-thienyl]-2-methylpyridine To a solution of 1-allyl-2-[3-(2,4-dichlorophenyl)-5-(tributylstannyl)-2-thienyl]-1H-imidazole (300 mg, 0.48 mmol) and 4-bromo-2-picoline (68.9 mg, 0.40 mmol) in DMF (10.0 mL) was added bis(triphenylphosphine)palladium dichloride (14.1 mg, 0.02 mmol) under atmosphere of Argon then the mixture was heated at 90° C. for 1 h. After cooling to room temperature, the solvent was evaporated and the residue was purified by column chromatography (SiO$_2$, elution with 3-5% MeOH in DCM) to give 121 mg of product (67%). LC/MS (AA) ES+ 428. $^1$H NMR (400 MHz, d$_6$ DMSO) δ: 8.48 (d, J=4.8 Hz, 1H), 7.93 (s, 1H), 7.72 (d, J=2.1 Hz, 1H), 7.60 (br s, 1H), 7.50-7.53 (m, 1H), 7.41 (dd, J=2.1, 8.4 Hz, 1H), 7.18-7.21 (m, 2H), 7.03 (d, J=1.1 Hz, 1H), 5.53-5.64 (m, 1H), 5.04 (dd, J=1.3, 10.3 Hz, 1H), 4.82 (dd, J=1.3, 17.1 Hz, 1H), 4.26-4.31 (m, 2H), 2.51 (s, 3H).

Step 3, Preparation of 4-[4-(2,4-dichlorophenyl)-5-(1H-imidazol-2-yl)-2-thienyl]-2-methylpyridine (66-A)

To a solution of 4-[5-(1-allyl-1H-imidazol-2-yl)-4-(2,4-dichlorophenyl)-2-thienyl]-2-methylpyridine (115 mg, 0.26 mmol) in DCM (10.0 mL) was added phenylsilane (0.16 mL, 1.28 mmol), acetic acid (0.66 mL, 11.5 mmol), and tetrakis(triphenylphosphine)palladium (14.8 mg, 0.01 mmol) at room temperature then the mixture was stirred for 2 h at 40° C. After cooling to room temperature, the solvent was evaporated under reduced pressure and the residual acetic acid was quenched by addition of saturated NaHCO$_3$ (50 mL). The mixture was extracted with DCM (3×70 mL), and the combined DCM layers were dried over Na$_2$SO$_4$, filtered, and concentrated in vacuo. The residue was purified by column chromatography (SiO$_2$, elution with 3-5% MeOH in DCM) to give crude product which was further purified by column chromatography (SiO$_2$, elution with 100% EtOAc) to provide 51 mg of product (49% yield). LC/MS (FA) ES+ 388. $^1$H NMR (400 MHz, d$_6$ DMSO) δ: 11.7 (br s, 1H), 8.46 (d, J=5.3 Hz, 1H), 7.76 (s, 1H), 7.72 (d, J=2.1 Hz, 1H), 7.57 (br s, 1H), 7.46-7.50 (m, 2H), 7.41 (d, J=8.3 Hz, 1H), 7.10 (br s, 1H), 6.95 (br s, 1H), 2.49 (s, 3H).

Compounds in the following table were prepared from the appropriate starting materials in a method analogous to that of Example 8:

| | |
|---|---|
| 84 | LCMS: (AA) ES+ 402, 404. |
| 85 | LCMS: (FA) ES+ 430, 432. |

Example 9

Synthesis of N-{4-[3-cyano-4-(2,4-dichlorophenyl)-5-(1H-1,2,3-triazol-5-yl)-2-thienyl]pyridin-2-yl}acetamide (70 and 73)

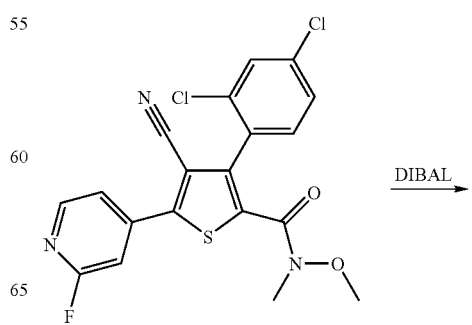

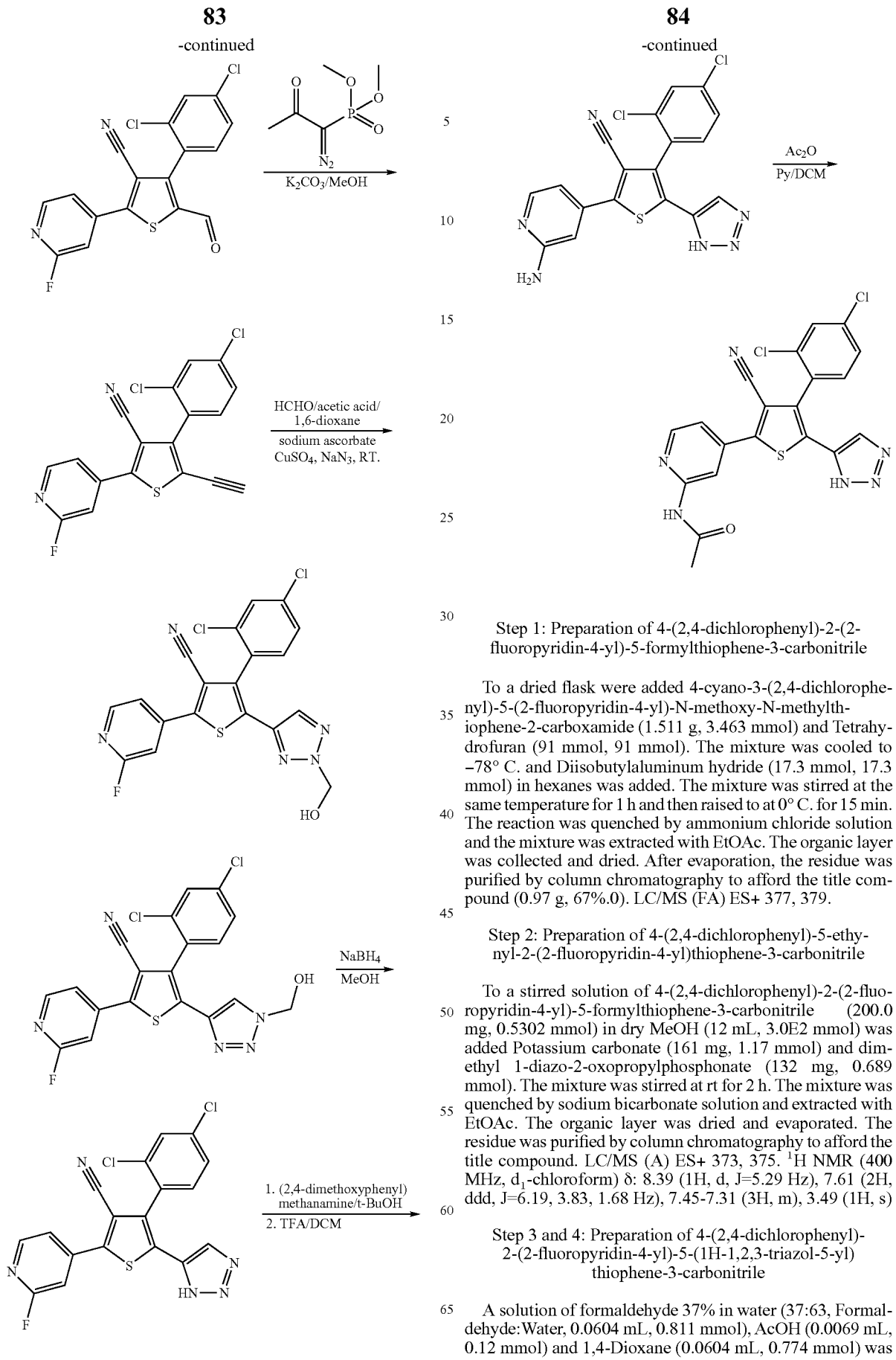

Step 1: Preparation of 4-(2,4-dichlorophenyl)-2-(2-fluoropyridin-4-yl)-5-formylthiophene-3-carbonitrile To a dried flask were added 4-cyano-3-(2,4-dichlorophenyl)-5-(2-fluoropyridin-4-yl)-N-methoxy-N-methylthiophene-2-carboxamide (1.511 g, 3.463 mmol) and Tetrahydrofuran (91 mmol, 91 mmol). The mixture was cooled to −78° C. and Diisobutylaluminum hydride (17.3 mmol, 17.3 mmol) in hexanes was added. The mixture was stirred at the same temperature for 1 h and then raised to at 0° C. for 15 min. The reaction was quenched by ammonium chloride solution and the mixture was extracted with EtOAc. The organic layer was collected and dried. After evaporation, the residue was purified by column chromatography to afford the title compound (0.97 g, 67%.0). LC/MS (FA) ES+ 377, 379.

Step 2: Preparation of 4-(2,4-dichlorophenyl)-5-ethynyl-2-(2-fluoropyridin-4-yl)thiophene-3-carbonitrile To a stirred solution of 4-(2,4-dichlorophenyl)-2-(2-fluoropyridin-4-yl)-5-formylthiophene-3-carbonitrile (200.0 mg, 0.5302 mmol) in dry MeOH (12 mL, 3.0E2 mmol) was added Potassium carbonate (161 mg, 1.17 mmol) and dimethyl 1-diazo-2-oxopropylphosphonate (132 mg, 0.689 mmol). The mixture was stirred at rt for 2 h. The mixture was quenched by sodium bicarbonate solution and extracted with EtOAc. The organic layer was dried and evaporated. The residue was purified by column chromatography to afford the title compound. LC/MS (A) ES+ 373, 375. $^1$H NMR (400 MHz, $d_1$-chloroform) δ: 8.39 (1H, d, J=5.29 Hz), 7.61 (2H, ddd, J=6.19, 3.83, 1.68 Hz), 7.45-7.31 (3H, m), 3.49 (1H, s)

Step 3 and 4: Preparation of 4-(2,4-dichlorophenyl)-2-(2-fluoropyridin-4-yl)-5-(1H-1,2,3-triazol-5-yl)thiophene-3-carbonitrile A solution of formaldehyde 37% in water (37:63, Formaldehyde:Water, 0.0604 mL, 0.811 mmol), AcOH (0.0069 mL, 0.12 mmol) and 1,4-Dioxane (0.0604 mL, 0.774 mmol) was stirred 15 min before Sodium azide (0.0079 g, 0.12 mmol) was added, followed by 4-(2,4-dichlorophenyl)-5-ethynyl-2-(2-fluoropyridin-4-yl)thiophene-3-carbonitrile (0.030 g, 0.080 mmol). The mixture was stirred for another 10 min. Sodium ascorbate (0.0032 g, 0.016 mmol) was added and then followed by Copper(II) sulfate (0.00064 g, 0.0040 mmol). The mixture was stirred overnight. The mixture was diluted with water and extracted with EtOAc. The organic layer was dried and evaporated to afford a crude intermediate which was purified by column chromatography to afford a mixture of 2 isomers.

To the above intermediate in MeOH (1.0 mL, 25 mmol) was added Sodium tetrahydroborate (3.04 mg, 0.0804 mmol) and the mixture was stirred at rt for 4 h. The solvent was removed and the residue was dissolved in water (0.5 ml) and 1NHCl (0.5 ml). The precipitate was collected and dried in air to afford the title compound (33 mg, 89%). LC/MS (FA) ES+ 416, 418. $^1$H NMR (400 MHz, d$_4$-methanol) δ: 8.40 (1H, d, J=5.33 Hz), 7.79 (2H, m), 7.57 (2H, m), 7.50 (1H, d, J=8.26 Hz), 7.11 (1H, s)

Step 5: Preparation of 2-(2-aminopyridin-4-yl)-4-(2,4-dichlorophenyl)-5-(1H-1,2,3-triazol-5-yl)thiophene-3-carbonitrile (70)

A solution of 4-(2,4-dichlorophenyl)-2-(2-fluoropyridin-4-yl)-5-(1H-1,2,3-triazol-5-yl)thiophene-3-carbonitrile (0.103 g, 0.247 mmol), 2,4-dimethoxybenzylamine (0.247 g, 1.48 mmol) and DIPEA (0.0959 g, 0.742 mmol) in 1-Butanol (15 g, 2.0E2 mmol) was irradiated in microwave at 170° C. for 2 hrs. The mixture was concerntrated and the residue was purified by column chromatography to afford desired intermediate. LC/MS (FA) ES+ 563, 565. To the intermediate in DCM (5.9 mL, 93 mmol) was added TFA (2 mL, 20 mmol) and the mixture was stirred for 10 min. The reaction mixture was concerntrated and the residue in MeOH was treated with sodium bicarbonate and water. The mixture was concentrated and the mixture was purified by column chromatography to afford the title compound (48 mg, 47.0%). LC/MS (FA) ES+ 413, 415. $^1$H NMR (400 MHz, d$_4$-methanol) δ: 8.03 (1H, d, J=6.26 Hz), 7.74 (1H, d, J=1.93 Hz), 7.54 (1H, dd, J=8.27, 1.97 Hz), 7.46 (1H, d, J=8.26 Hz), 7.05 (1H, s), 7.01 (2H, m)

Step 6: Preparation of N-{4-[3-cyano-4-(2,4-dichlorophenyl)-5-(1H-1,2,3-triazol-5-yl)-2-thienyl]pyridin-2-yl}acetamide (73)

To a solution of 2-(2-aminopyridin-4-yl)-4-(2,4-dichlorophenyl)-5-(1H-1,2,3-triazol-5-yl)thiophene-3-carbonitrile (0.048 g, 0.12 mmol) in DCM (4 mL, 60 mmol) was added Pyridine (0.470 mL, 5.81 mmol) and Acetic anhydride (329 uL, 3.48 mmol) and the mixture was stirred at rt overnight. The mixture was concentrated and the residue was dissolved in MeOH (2.0 mL, 49 mmol) and Water (0.3 mL, 20 mmol). Sodium bicarbonate (0.5 g, 6 mmol) was added to the above mixture. The mixture was stirred at rt for 30 min. The reaction mixture was concentrated and the residue was dissolved in EtOAc and MeOH. The solid was filtered out. The organic solution was evaporated to dryness, purified by column chromatography and then further by HPLC to afford pure title compound (27 mg, 52%). LC/MS (FA) ES+ 455, 457; ES– 453, 455. $^1$H-NMR (400 MHz, DMSO-d$_6$) δ: 8.59 (1H, d, J=0.75 Hz), 8.51 (1H, d, J=5.29 Hz), 7.93 (1H, d, J=1.09 Hz), 7.54 (1H; dd, J=5.25, 1.76 Hz), 7.23 (1H, s), 7.64 (2H, d, J=1.92 Hz), 10.80 (1H, s), 2.13 (3H, s), 2.07 (1H, s)

Example 10

Synthesis of N-(4-{3-cyano-4-(2,4-dichlorophenyl)-5-[1-(4-fluorobenzyl)-1H-imidazol-2-yl]-2-thienyl}pyridin-2-yl)acetamide (72)

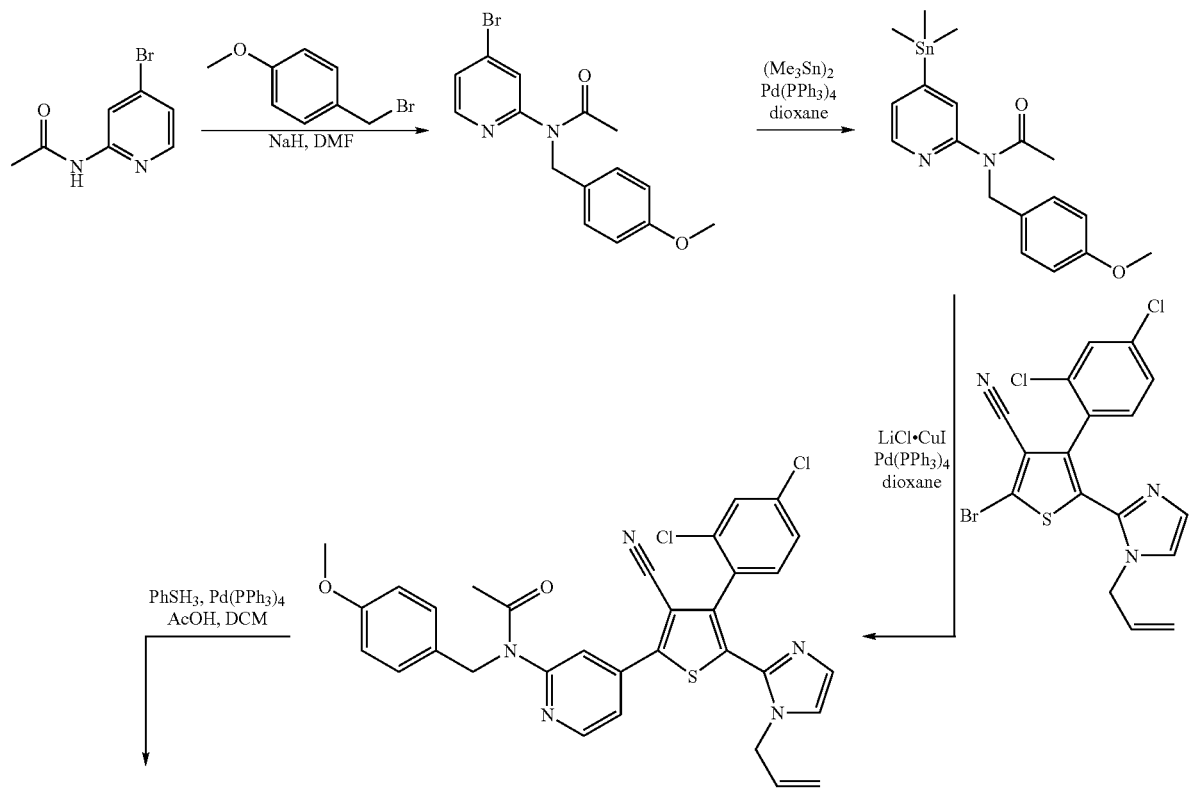

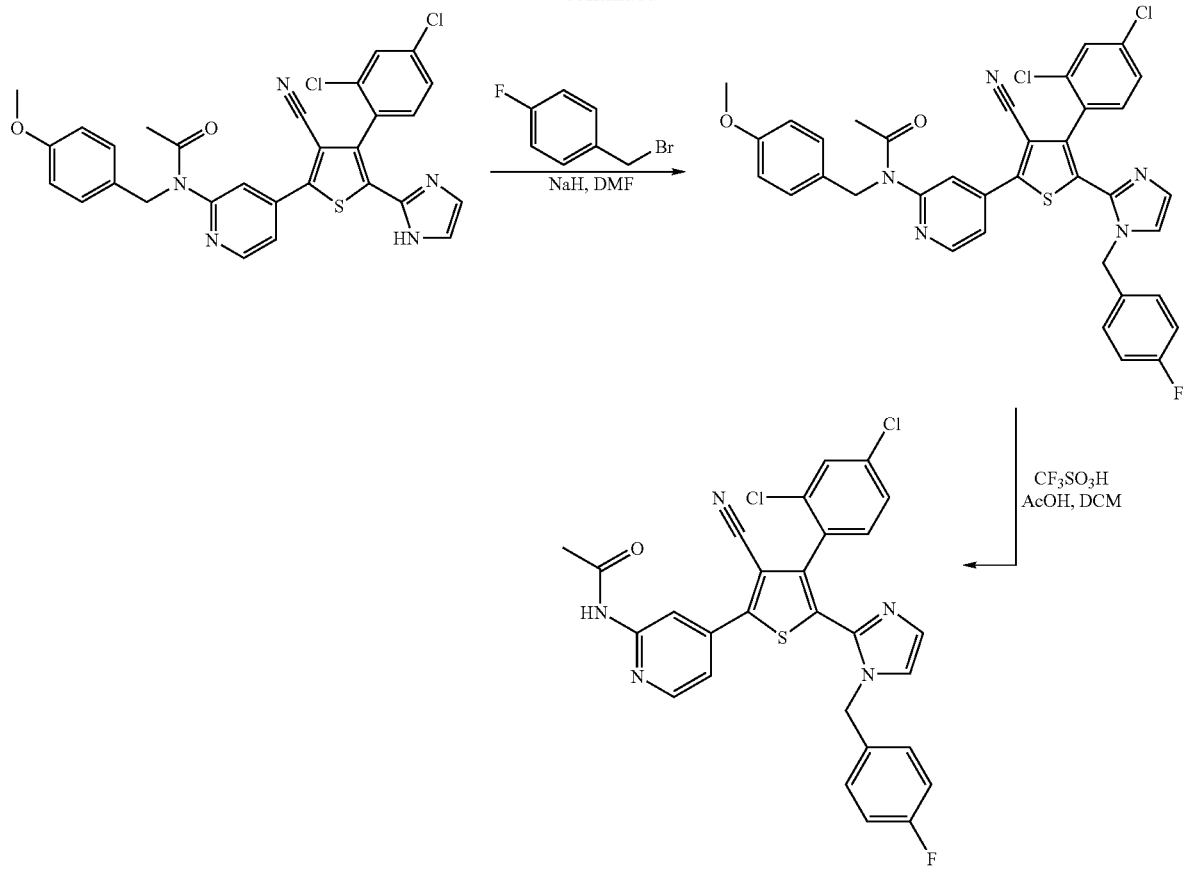

Step 1: N-(4-bromopyridin-2-yl)-N-(4-methoxybenzyl)acetamide

To a 20 mL vial charged with Sodium hydride (0.196 g, 7.76 mmol) was added dry N,N-Dimethylformamide (5.0 mL, 64 mmol), cooled with ice bath. N-(4-bromopyridin-2-yl)acetamide (1.50 g, 7.00 mmol) was added portionwise in ~3 min. The suspension was stirred at the same temperature for 15 min and turned into a clear solution. 4-methoxybenzyl bromide (1.55 g, 7.70 mmol) was added dropwise with a syringe and rinsed down with dry N,N-Dimethylformamide (2.0 mL, 26 mmol). The mixture was stirred at r.t. for 17 hours. The mixture was poured into ice chilled saturated $NaHCO_3$ (80 mL), extracted with EtOAc (2×100 mL), washed with water, brine, dried over anhydrous $Na_2SO_4$, filtered, evaporated in rotavpor to give a crude. Chromatograph using EtOAc/hexane (1/9 to 7/3) gave an oily product (1.80 g, yield 76.7%). LCMS: (AA) $ES^+$, 335, 337. $^1H$ NMR (400 MHz, $d_1$-chloroform) δ: 8.28-8.30 (d, J=5.27 Hz, 1H), 7.43 (s, 1H), 7.31-7.33 (dd, J=5.52, 1.51 Hz, 1H), 7.13-7.15 (d, J=8.78 Hz, 2H), 6.80-6.82 (d, J=8.78 Hz, 2H), 5.05 (s, 2H), 3.77 (s, 3H), 2.12 (s, 3H).

Step 2: N-(4-methoxybenzyl)-N-[4-(trimethylstannyl)pyridin-2-yl]acetamide

The mixture of N-(4-bromopyridin-2-yl)-N-(4-methoxybenzyl)acetamide (1.79 g, 5.34 mmol), Hexamethylditin (2.10 g, 6.41 mmol) and Tetrakis(triphenylphosphine)palladium(0) (0.308 g, 0.267 mmol) in dry 1,4-Dioxane (45 mL, 580 mmol) was heated to 95° C. (heating block) under $N_2$ for 3 hours. The mixture was evaporated in rotavapor and the residue was purified in a silica column using EtOAc/hexane (1/9 to 5/5) to give an oily product (1.82 g, 81.3%). LCMS: (AA) $ES^+$, 417, 419, 421. $^1H$ NMR (400 MHz, $d_1$-chloroform) δ: 8.40-8.41 (d, J=5.52 Hz, 1H), 7.21-7.32 (m, 1H), 7.13-7.15 (d, J=8.78 Hz, 2H), 6.99-7.02 (m, 1H), 6.77-6.80 (d, J=8.78 Hz, 2H), 4.98 (s, 2H), 3.76 (s, 3H), 2.01 (s, 3H), 0.21-0.36 (m, 9H).

Step 3: N-{4-[5-(1-allyl-1H-imidazol-2-yl)-3-cyano-4-(2,4-dichlorophenyl)-2-thienyl]pyridin-2-yl}-N-(4-methoxybenzyl)acetamide The mixture of 5-(1-allyl-1H-imidazol-2-yl)-2-bromo-4-(2,4-dichlorophenyl)thiophene-3-carbonitrile (0.840 g, 1.91 mmol), N-(4-methoxybenzyl)-N-[4-(trimethylstannyppyridin-2-yl]acetamide (0.992 g, 2.37 mmol) Lithium chloride (0.232 g, 5.46 mmol), Copper(I) iodide (0.104 g, 0.546 mmol) and Tetrakis(triphenylphosphine)palladium(0) (0.210 g, 0.182 mmol) in dry 1,4-Dioxane (50 mL, 600 mmol) was heated under $N_2$ to reflux for 1 hour. The mixture was cooled to r.t., evaporated in rotavapor. The residue was quenched with aqueous saturated $NaHCO_3$, extracted with DCM (2×150 mL), washed with water, brine, dried over $Na_2SO_4$, filtered, evaporated in rotavapor to give a brown solid. The solid was heated in EtOAc/DCM (50 mL/15 mL) to reflux for 15 min, cooled to r.t., filtered and washed with small amount of EtOAc. The filtrate was purified on a silica column using hexane as solvent A and hexane:concentrated aqueous $NH_4OH$:MeOH:DCM (67%:0.5%:10.5%:22%) as solvent B (A/B from 100/0 to 0/100 in 5 min then 100% B for 10 min)

to give a solid product (1.32 g, 75% pure by LCMS, yield 84.2%). LCMS: (AA) ES⁺, 614, 616. The product was used for next step without further purification.

Step 4: N-{4-[3-cyano-4-(2,4-dichlorophenyl)-5-(1H-imidazol-2-yl)-2-thienyl]pyridin-2-yl}-N-(4-methoxybenzyl)acetamide To the solution of N-{4-[5-(1-allyl-1H-imidazol-2-yl)-3-cyano-4-(2,4-dichlorophenyl)-2-thienyl]pyridin-2-yl}-N-(4-methoxybenzyl)acetamide (1.32 g, 1.61 mmol) and Tetrakis(triphenylphosphine)palladium(0) (93.1 mg, 0.0805 mmol) in Acetic acid (15 mL, 260 mmol) and Methylene chloride (30 mL, 500 mmol) under N₂ atmosphere was added dropwise PHENYLSILANE (1.10 mL, 8.92 mmol). The mixture was stirred at 40° C. for 2 hours. The solvent was removed in rotavapor then the residue was dried in high vacuum to give a residue. The residue was chromatographed in silica column using 7N NH3-MeOH/DCM (1/99, ~1 L), then EtOAc/DCM (30/70 to 60/40) to give an impure product. The second chromatograph using EtOAc/DCM (30/70 to 80/20) gave a pure product (0.469 g, yield 50.7%). LCMS: (AA) ES⁺, 574, 576; ES⁻, 572, 574. ¹H NMR (400 MHz, d₁-chloroform) δ: 8.60-8.62 (d, J=5.27 Hz, 1H), 7.71 (d, J=2.00 Hz, 1H), 7.63 (s, br, 1H), 7.55-7.57 (dd, J=5.27, 1.76 Hz, 1H), 7.50-7.52 (dd, J=8.28, 2.01 Hz, 1H), 7.40-7.42 (d, J=8.28 Hz, 1H). 7.18-7.20 (d, J=8.78 Hz, 2H), 7.07 (m, 2H), 6.80-6.82 (d, J=8.78 Hz, 2H), 5.14 (s, 2H), 3.76 (s, 3H), 2.19 (s, 3H).

Step 5: N-(4-{3-cyano-4-(2,4-dichlorophenyl)-5-[1-(4-fluorobenzyl)-1H-imidazol-2-yl]-2-thienyl}pyridin-2-yl)-N-(4-methoxybenzyl)acetamide To the solution of N-{4-[3-cyano-4-(2,4-dichlorophenyl)-5-(1H-imidazol-2-yl)-2-thienyl]pyridin-2-yl}-N-(4-methoxybenzyl)acetamide (60.0 mg, 0.104 mmol) in dry N,N-Dimethylformamide (5.0 mL, 64 mmol) was added Sodium hydride (3.96 mg, 0.157 mmol). The resulted red-brown solution was stirred at r.t. for 10 min. 4-Fluorobenzyl bromide (32.6 mg, 0.172 mmol) was added and the mixture was stirred at r.t. for 2 hours, The mixture was quenched with aqueous saturated NaHCO₃ (10 mL), diluted with water, extracted with DCM (4×25 mL), washed with water, brine, dried over Na₂SO₄, filtered, rotovaped to give a crude residue. Chromatograph in silica using DCM/EtOAc (30/70 to 0/100) afforded a solid product (0.055 g, yield 77.1%). LCMS: (AA) ES⁺, 682, 684. ¹H NMR (400 MHz, d₁-chloroform) δ: 8.60-8.62 (d, J=5.02 Hz, 1H), 7.63 (s, br, 1H), 7.51-7.53 (m, 1H), 7.34 (m, 1H), 7.14-7.26 (m, 5H), 6.92-6.97 (m, 2H), 6.80-6.86 (m, 3H), 6.70-6.73 (m, 2H), 5.14 (m, 2H), 4.71-4.84 (m, 2H), 3.76 (s, 3H), 2.19 (s, 3H).

Step 6: N-(4-{3-cyano-4-(2,4-dichlorophenyl)-5-[1-(4-fluorobenzyl)-1H-imidazol-2-yl]-2-thienyl}pyridin-2-yl)acetamide (72)

To the solution of [A] N-(4-{3-cyano-4-(2,4-dichlorophenyl)-5-[1-(4-fluorobenzyl)-1H-imidazol-2-yl]-2-thienyl}pyridin-2-yl)-N-(4-methoxybenzyl)acetamide (55.0 mg, 0.0806 mmol) in Acetic acid (1.0 mL, 18 mmol) was added Trifluoromethanesulfonic acid (0.10 mL, 1.1 mmol) and the mixture was stirred at r.t. for 20 hours. Methylene chloride (2.0 mL, 31 mmol) and Trifluoromethanesulfonic acid (0.10 mL, 1.1 mmol) were added and the mixture was stirred at r.t. for 20 hours. The mixture was rotovaped and azeotropped with toluene twice, dried in high vacuum. The residue was neutralized with aqueous saturated NaHCO₃ to pH ~8, extracted with EtOAc. The EtOAc solution was dried over Na₂SO₄, filtered, evaporated in rotavapor to give a crude residue. Chromatograph in a silica column using MeOH/DCM (0/100 to 2/98) afforded a solid product. The product was dissolved in small amount of acetonitrile and ~5 mL water, frozen in dry ice and lyophilized to give a powder product (20 mg, yield 44.1%). LCMS: (AA) ES⁺, 562, 564; FS⁻, 560, 562. ¹H NMR (400 MHz, d₄-methanol) δ: 8.62 (s, 1H), 8.47-8.48 (d, J=5.27 Hz, 1H), 7.53-7.55 (dd, J=5.27, 1.76 Hz, 1H), 7.47 (d, J=2.01 Hz, 1H), 7.33-7.36 (dd, J=8.28, 2.01 Hz, 1H), 7.26-7.27 (d, J=8.28 Hz, 1H), 7.16-7.19 (dd, J=7.28, 1.51 Hz, 2H), 6.98-7.02 (m, 2H), 6.83-6.86 (m, 2H), 4.98 (s, 2H), 2.21 (s, 3H).

Compounds in the following table were prepared from the appropriate starting materials in a method analogous to that of Example 10:

| | |
|---|---|
| 67 | LCMS: (AA) ES+ 468, 470. |
| 71 | LCMS: (AA) ES+ 545, 547. |
| 78 | LCMS: (AA) ES+ 545, 547. |

Example 11

Synthesis of N-{4-[5-(5-bromo-4H-1,2,4-triazol-3-yl)-3-cyano-4-(2,4-dichlorophenyl)-2-thienyl]pyridin-2-yl}acetamide (74)

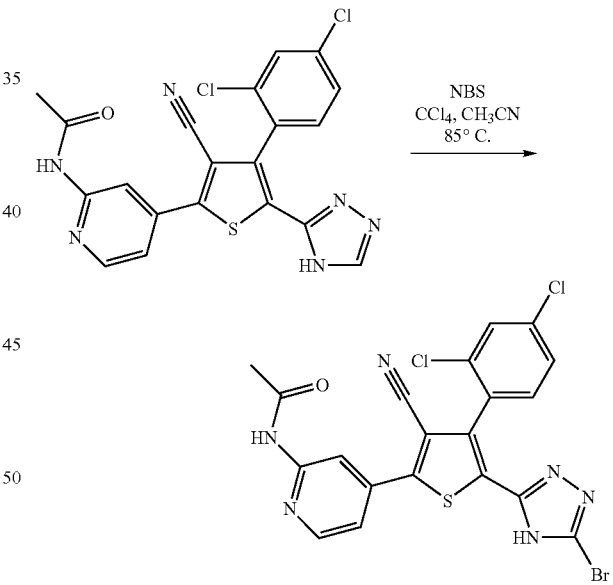

A suspension of N-(4-(3-cyano-4-(2,4-dichlorophenyl)-5-(4H-1,2,4-triazol-3-yl)thiophen-2-yl)pyridin-2-yl)acetamide (0.0700 g, 0.154 mmol) and N-Bromosuccinimide (33.1 mg, 0.186 mmol) in Carbon tetrachloride (2.5 mL, 26 mmol) was heated to 85° C. in a capped vial for 2.5 hours. To the suspension was added dry Acetonitrile (6.0 mL, 110 mmol) and the mixture was heated at 85° C. (turned into a clear solution) for 2 hours. The mixture was cooled to r.t., evaporated in rotavapor. The residue was dry loaded in a silica column and eluted with MeOH/DCM (0/100 to 5/95) to give a solid product (66.0 mg, yield 80.4%). LCMS: (FA) ES⁺, 533, 535, 537 and ES⁻ 531, 533, 535. ¹H NMR (400 MHz, d₁-chloroform) δ: 8.65 (s, 1H), 8.42 (d, J=5.02 Hz, 1H), 8.26 (s, 1H), 7.61 (d, J=2.01 Hz, 1H), 7.56 (dd, J=5.27, 1.76 Hz, 1H), 7.43-7.45 (dd, J=8.28, 2.01 Hz, 1H), 7.37-7.39 (d, J=8.28 Hz, 1H), 2.26 (s, 3H).

Example: 12

Synthesis of N-(4-(3-cyano-4-(2,4-dichlorophenyl)-5-(1H-pyrazol-5-yl)thiophen-2-yl)pyridin-2-yl)acetamide (76)

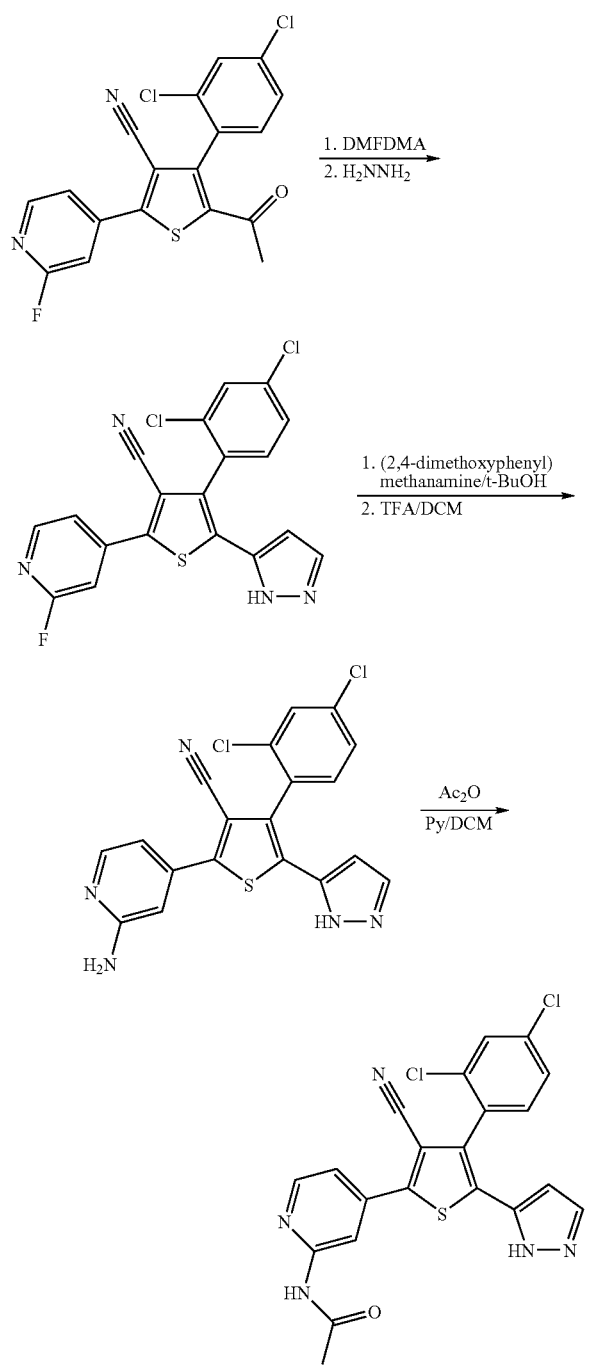

Step 1: Preparation of 4-(2,4-dichlorophenyl)-2-(2-fluoropyridin-4-yl)-5-(1H-pyrazol-5-yl)thiophene-3-carbonitrile A solution of [A] 5-acetyl-4-(2,4-dichlorophenyl)-2-(2-fluoropyridin-4-yl)thiophene-3-carbonitrile (0.407 g, 1.04 mmol) in 1,1-Dimethoxy-N,N-dimethylmethanamine (5.53 mL, 41.6 mmol) was irradiated in microwave at 120° C. for 20 min. The solvent was removed and the residue was taken up by AcOH (21 mL, 370 mmol). Hydrazine hydrate (3 mL, 60 mmol) was added the above mixture and then heated at 90° C. for 10 min. The mixture was concentrated and the residue was suspended in water. The precipitated was collected and dried in air to afford the title compound as a yellow powder (0.34 g, 79%). LC/MS (FA) ES+ 415, 417. ¹H NMR (400 MHz, d₄-methanol) δ: 8.45 (1H, d, J=5.33 Hz), 7.85 (1H, td, J=5.32, 1.57, 1.57 Hz), 7.80 (1H, d, J=1.99 Hz), 7.54 (1H, d, J=8.24 Hz), 7.60 (1H, dd, J=8.27, 2.04 Hz), 7.63 (2H, d, J=2.47 Hz), 5.69 (1H, d, J=2.44 Hz)

Step 2: Preparation of 2-(2-aminopyridin-4-yl)-4-(2,4-dichlorophenyl)-5-(1H-pyrazol-5-yl)thiophene-3-carbonitrile (79)

4-(2,4-dichlorophenyl)-2-(2-fluoropyridin-4-yl)-5-(1H-pyrazol-5-yl)thiophene-3-carbonitrile (0.372 g, 0.903 mmol), 2,4-dimethoxybenzylamine (821 mg, 4.91 mmol) and DIPEA (317 mg, 2.46 mmol) in 1-Butanol (3.74 mL, 40.9 mmol) was irradiated in microwave at 160° C. for 2 hr under nitrogen. The solvent was evaporated and the residue was purified by column chromatography to afford an intermediate which was in the next step. LC/MS (FA) ES+ 562, 564. The above intermediate was dissoved in DCM (26 mL, 4.0E2 mmol) and TFA (8.5 mL, 110 mmol). The mixture was stirred at rt for 30 min. The mixture was concentrated and the residue was basified by ammonium hydroxide. The solvent was evaporated and the mixture was purified by column chromatography to afford the title compound (0.375 g, 100%). LC/MS (FA) ES+ 412, 414. ¹H NMR (400 MHz, d₄-methanol) δ: 8.00 (1H, d, J=6.62 Hz), 7.77 (1H, d, J=2.01 Hz), 7.59 (1H, d, J=2.45 Hz), 7.56 (1H, dd, J=8.26, 2.02 Hz), 7.49 (1H, d, J=8.27 Hz), 7.38 (1H, d, J=1.59 Hz), 7.24 (1H, dd, J=6.64, 1.77 Hz), 5.58 (1H, d, J=2.38 Hz)

Step 3: Preparation of N-(4-(3-cyano-4-(2,4-dichlorophenyl)-5-(1H-pyrazol-5-yl)thiophen-2-yl)pyridin-2-yl)acetamide (76)

To a mixture of 2-(2-aminopyridin-4-yl)-4-(2,4-dichlorophenyl)-5-(1H-pyrazol-5-yl)thiophene-3-carbonitrile (0.10 g, 0.12 mmol) and Pyridine (0.3923 mL, 4.851 mmol) in DCM (0.2 mL, 3 mmol) was added Acetic anhydride (0.114 mL, 1.21 mmol) at 0° C. The ice bath was removed after 2 h and stirring was continued at rt overnight. The solvent was evaporated and the residue was stirred in MeOH (5 mL, 100 mmol) and Water (1 g, 60 mmol) containing Sodium bicarbonate (0.6112 g, 7.276 mmol). The mixture was concentrated and the residue was collected with EtOAc. The mixture was washed with brine and dried. The solvent was evaporated and the residue was purified by column chromatography to afford the title compound (0.024 g, 41%). LC/MS (FA) ES+

454, 456. $^1$H NMR (400 MHz, DMSO-$d_6$) δ: 13.28 (1H, s), 10.78 (1H, s), 8.58 (1H, s), 8.50 (1H, dd, J=5.27, 0.63 Hz), 7.93 (1H, d, J=1.71 Hz), 7.71 (1H, d, J=2.37 Hz), 7.63 (2H, dd, J=5.25, 1.77 Hz), 7.53 (1H, dd, J=5.25, 1.77 Hz), 5.49 (1H, d, J=2.38 Hz), 2.13 (3H, s)

Compounds in the following table were prepared from the appropriate starting materials in a method analogous to that of Example 12:

| | |
|---|---|
| 81 | LCMS: (FA) ES+ 480, 482. |
| 82 | LCMS: (FA) ES+ 455, 457. |
| 83 | LCMS: (FA) ES+ 469, 471. |

Example 13

Synthesis of N-(4-(3-cyano-4-(2,4-dichlorophenyl)-5-(1H-imidazol-5-yl)thiophen-2-yl)pyridin-2-yl)acetamide (77)

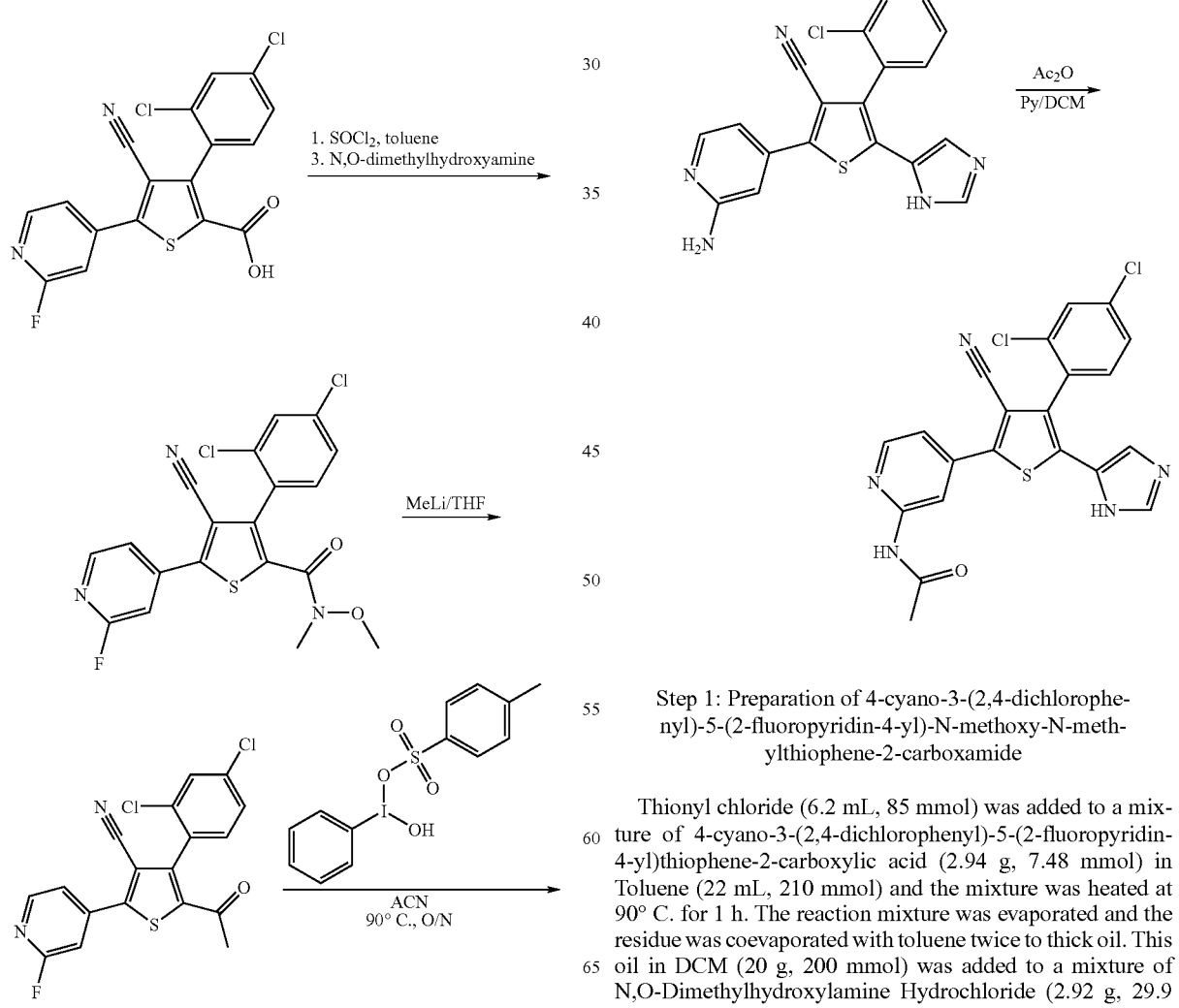

Step 1: Preparation of 4-cyano-3-(2,4-dichlorophenyl)-5-(2-fluoropyridin-4-yl)-N-methoxy-N-methylthiophene-2-carboxamide Thionyl chloride (6.2 mL, 85 mmol) was added to a mixture of 4-cyano-3-(2,4-dichlorophenyl)-5-(2-fluoropyridin-4-yl)thiophene-2-carboxylic acid (2.94 g, 7.48 mmol) in Toluene (22 mL, 210 mmol) and the mixture was heated at 90° C. for 1 h. The reaction mixture was evaporated and the residue was coevaporated with toluene twice to thick oil. This oil in DCM (20 g, 200 mmol) was added to a mixture of N,O-Dimethylhydroxylamine Hydrochloride (2.92 g, 29.9 mmol) and TEA (7.0 mL, 5.0E1 mmol) in DCM (100 mL, 2000 mmol) in a ice bath. After 2 h, the mixture was washed by water and brine. The DCM layer was collected and dried and evaporated in vacuum to afford crude intermediate, which was purified by column chromatography to afford the title compound (2.41 g, 73.9%). LCMS: (FA) ES+, 436, 438. $^1$H NMR (400 MHz, $d_1$-chloroform) δ: 8.41 (1H, d, J=5.26 Hz), 7.72-7.63 (1H, m), 7.54 (1H, d, J=1.96 Hz), 7.39 (2H, dd, J=7.70, 1.99 Hz), 7.29 (1H, d, J=8.26 Hz), 3.76 (3H, s), 3.27 (3H, s)

Step 2: Preparation of 5-acetyl-4-(2,4-dichlorophenyl)-2-(2-fluoropyridin-4-yl)thiophene-3-carbonitrile To a flame dried flask were placed 4-cyano-3-(2,4-dichlorophenyl)-5-(2-fluoropyridin-4-yl)-N-methoxy-N-methylthiophene-2-carboxamide (1.45 g, 3.32 mmol) and tetrahydrofuran (90 mL, 1000 mmol) under argon. The solution was cooled to −78° C. and Methyllithium (4.653 mmol, 4.653 mmol) in diethylether (1.6M) solution was added. After addition, the mixture was kept at this temperature for 30 min. The mixture was quenched by ammonium chloride solution. The mixture was extracted with EtOAc and the organic layer was collected and dried over Na2SO4. The solvent was evaporated and the residue was purified using column chromatography. The title compound was collected as a white solid (0.93 g, 71.5%). LCMS: (FA) ES+391, 393. $^1$H NMR (400 MHz, $d_1$-chloroform) δ: 8.43 (1H, d, J=5.28 Hz), 7.67-7.62 (2H, m), 7.48 (1H, dd, J=8.24, 2.01 Hz), 7.38 (1H, s), 7.35 (1H, d, J=8.24 Hz), 2.13 (3H, s)

Step 3: Preparation of 2-(4-cyano-3-(2,4-dichlorophenyl)-5-(2-fluoropyridin-4-yl)thiophen-2-yl)-2-oxoethyl 4-methylbenzenesulfonate A mixture of 5-acetyl-4-(2,4-dichlorophenyl)-2-(2-fluoropyridin-4-yl)thiophene-3-carbonitrile (0.48 g, 1.2 mmol) and [hydroxy(tosyloxy)iodo]benzene (0.819 g, 2.09 mmol) in ACN (20 mL, 400 mmol) was heated at 90° C. overnight. The mixture was cooled down to rt. The solvent was evaporated and the residue was purified by column chromatography to afford the title compound (0.31 g, 45%). $^1$H NMR (300 MHz, $d_1$-chloroform) δ: 8.44 (1H, d, J=5.27 Hz), 7.69 (2H, d, J=8.34 Hz), 7.62 (2H, ddd, J=6.91, 3.43, 1.72 Hz), 7.47 (1H, dd, J=8.25, 2.02 Hz), 7.39-7.33 (3H, m), 7.30 (1H, d J=5.79), 4.47 (2H, s), 2.47 (3H, s)

Step 4: Preparation of 4-(2,4-dichlorophenyl)-2-(2-fluoropyridin-4-yl)-5-(1H-imidazol-5-yl)thiophene-3-carbonitrile 2-(4-cyano-3-(2,4-dichlorophenyl)-5-(2-fluoropyridin-4-yl)thiophen-2-yl)-2-oxoethyl 4-methylbenzenesulfonate (0.42 g, 0.75 mmol) in Formamide (140 mL, 3510 mmol) was heated to a true solution and then irradiated at 170° C. for 1 h. The reaction mixture was concentrated to remove part of solvent and the residue was partitioned between water and EtOAc. The organic layer was separated and washed with brine and then dried. After the solvent was evaporated, the residue was purified by column chromatography to give the title compound slightly impure (95 mg, 30.5%). LCMS: (FA) ES+415, 417

Step 5: Preparation of 2-(2-aminopyridin-4-yl)-4-(2,4-dichlorophenyl)-5-(1H-imidazol-5-yl)thiophene-3-carbonitrile (80)

A mixture of 4-(2,4-dichlorophenyl)-2-(2-fluoropyridin-4-yl)-5-(1H-imidazol-5-yl)thiophene-3-carbonitrile (45.0 mg, 0.108 mmol), 2,4-dimethoxybenzylamine (145 mg, 0.867 mmol) and DIPEA (42.0 mg, 0.325 mmol) in 1-Butanol (4.2 mL, 46 mmol) was irradiated in microwave at 160° C. for 3 hrs. The solvent was removed by evaporation, the residue was purified by column chromatography to the desired intermediate with minor impurities. LC/MS (FA) ES+ 562, 564; ES− 560-562.

To the above intermediate in DCM (1.3 mL, 21 mmol) was added TFA (0.48 mL, 6.2 mmol) at rt. The mixture was stirred for 1 h. The solvent was evaporated and the residue was purified by HPLC to afford title compound as white powder (16.7 mg, 27.4% in 2 steps). LC/MS (FA) ES+ 412, 414; ES− 410, 412. $^1$H NMR (400 MHz, $d_4$-methanol) δ: 8.08 (1H, d, J=5.6 Hz), 7.78 (2H, dd, J=16, 2 Hz), 7.61 (1H, dd, J=8.4, 2 Hz), 7.52 (1H, d, J=8 Hz), 7.11-7.04 (2H, m), 6.42 (1H, s)

Step 6: Preparation of N-(4-(3-cyano-4-(2,4-dichlorophenyl)-5-(1H-imidazol-5-yl)thiophen-2-yl)pyridin-2-yl)acetamide (77)

To a solution of 2-(2-aminopyridin-4-yl)-4-(2,4-dichlorophenyl)-5-(1H-imidazol-5-yl)thiophene-3-carbonitrile (16.3 mg, 0.0395 mmol) in Pyridine (130.5 mg, 1.650 mmol) and DCM (1.0 mL, 16 mmol) was added acetic anhydride (108.2 mg, 1.060 mmol). The mixture was stirred at rt overnight. The solvent was evaporated and the residue was dissolved in MeOH (4 mL, 90 mmol). Sodium bicarbonate (0.5 g, 6 mmol) was added and followed by water. The mixture was stirred for 30 min. The mixture was concentrated and the residue was dissolved in EtOAc. The organic phase was washed with water and the organic layer was separated and dried over sodium sulfate. The crude product was obtained by evaporation and the purified by column chromatography to afford pure title compound as a yellow solid (12.4 mg, 69.4%). LC/MS (AA) ES+ 454, 456; ES− 452, 454. $^1$H-NMR (DMSO-$d_6$, 300 MHz) δ: 12.63-12.07 (1H, br), 10.79-10.74 (1H, s), 8.57 (1H, s), 8.48 (1H, d, J=5.2 Hz), 7.94 (1H, d, J=1.89 Hz), 7.74 (1H, d, J=0.92 Hz), 7.62 (1H, s), 7.64 (1H, d, J=1.98 Hz), 7.51 (1H, dd, J=5.3, 1.7 Hz), 6.30 (1H, d, J=0.94 Hz), 2.13 (3H, s)

Example 14

Synthesis of Methyl 2-[5-[2-(acetylamino)pyridin-4-yl]-4-cyano-3-(2,4-dichlorophenyl)-2-thienyl]-1H-imidazole-5-carboxylate (75)

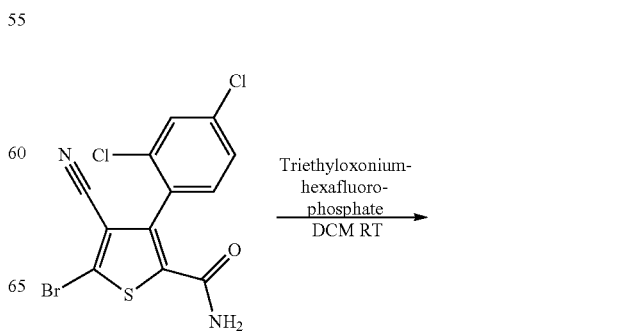

-continued

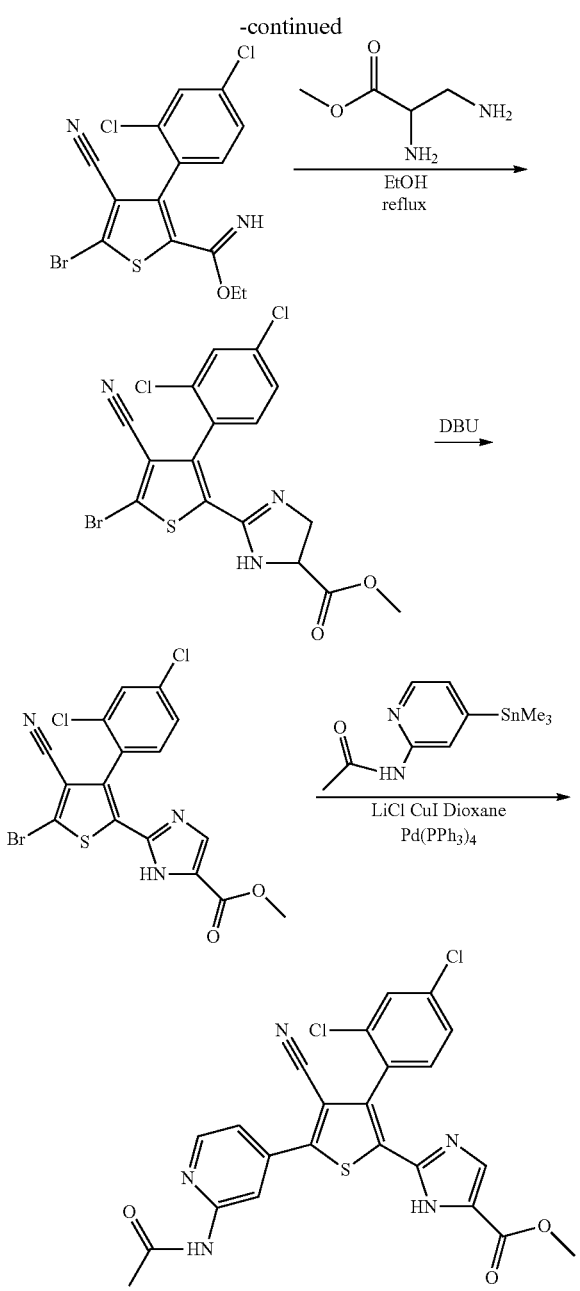

Step 1: Synthesis of Ethyl 5-bromo-4-cyano-3-(2,4-dichlorophenyl)thiophene-2-carboximidoate To a solution of 5-bromo-4-cyano-3-(2,4-dichlorophenyl) thiophene-2-carboxamide (prepared in an analogous way to the iodide intermediate shown in Example 3-A; 0.500 g, 1.33 mmol) in dichloromethane (28 mL) at 0° C. was added triethyloxonium hexafluorophosphate (2.31 g, 9.31 mmol). The mixture was allowed to slowly warm to room temperature, and stirred for 16 hours. The solution was poured into 1M sodium carbonate solution at 0° C., then the layers were separated, and the aqueous layer was extracted 3 times with dichloromethane. The organic extracts were washed with brine, dried over anhydrous sodium sulfate, filtered and concentrated in vacuo. Column chromatography was performed to yield the title compound (0.558 g, 104%). LCMS: (FA) ES$^+$, 405. $^1$H NMR (400 MHz, d$_1$-chloroform) δ: 7.60-7.57 (m, 1H), 7.43-7.38 (m, 1H), 7.29-7.25 (m, 1H), 4.30-4.22 (m, 2H), 1.40-1.37 (m, 3H).

Step 2: Synthesis of Methyl 2-[5-bromo-4-cyano-3-(2,4-dichlorophenyl)-2-thienyl]-4,5-dihydro-1H-imidazole-5-carboxylate To a solution of ethyl 5-bromo-4-cyano-3-(1,4-dichlorophenyl)thiophene-2-carboximidoate (0.548 g, 1.36 mmol) in ethanol (26 mL) was added methyl 2,3-diaminopropanoate dihydrochloride (0.313 g, 1.64 mmol). The solution was stirred at 80° C. for 4 hours. The solvent was evaporated, and column chromatography was performed to yield the title compound (0.222 g, 36%). LCMS: (FA) ES+ 460. $^1$H NMR (400 MHz, d$_4$-methanol) δ 7.70 (s, 1H), 7.55-7.43 (m, 2H), 3.76-3.66 (m, 4H), 1.36-1.26 (m, 3H).

Step 3: Synthesis of Methyl 2-[5-bromo-4-cyano-3-(2,4-dichlorophenyl)-2-thienyl]-1H-imidazole-5-carboxylate To a mixture of methyl 2-[5-bromo-4-cyano-3-(2,4-dichlorophenyl)-2-thienyl]-4,5-dihydro-1H-imidazole-5-carboxylate (0.341 g, 0.743 mmol), carbon tetrachloride (12.1 mL, 126 mmol), acetonitrile (18.3 mL, 351 mmol) and pyridine (12 mL, 150 mmol) was added 1,8-Diazabicyclo[5.4.0]undec-7-ene (0.442 mL, 2.96 mmol) slowly. The solution was stirred at room temperature for 16 hours. The mixture was evaporated, then the residue was diluted with dichloromethane and 0.5N aqueous HCl solution. The layers were separated, then the organic extracts were washed with brine, dried over anhydrous sodium sulfate, filtered and concentrated in vacuo. Column chromatography was performed to yield the title compound (0.226 g, 67%). LCMS: (FA) ES$^+$, 458. $^1$H NMR (400 MHz, d$_4$-Methanol) δ: 7.70-7.67 (m, 2H), 7.53-7.43 (m, 2H), 3.85 (s, 3H).

Step 4: Synthesis of Methyl 2-[5-[2-(acetylamino) pyridin-4-yl]-4-cyano-3-(2,4-dichlorophenyl)-2-thienyl]-1H-imidazole-5-carboxylate (75)

Methyl 2-[5-bromo-4-cyano-3-(2,4-dichlorophenyl)-2-thienyl]-1H-imidazole-5-carboxylate (0.216 g, 0.472 mmol), N-[4-(trimethylstannyl)pyridin-2-yl]acetamide (0.170 g, 0.567 mmol), lithium chloride (0.0601 g, 1.42 mmol), copper (I) iodide (0.0270 g, 0.142 mmol) and tetrakis(triphenylphosphine)palladium(0) (0.0273 g, 0.0236 mmol) were combined in dioxane (10 mL) under an atmosphere of Argon. The solution was heated at 110° C. for 3 hours. The solvent was evaporated, and column chromatography was performed to yield the title compound (0.0250 g, 10%). LCMS: (FA) ES+ 513. $^1$H NMR (300 MHz, d$_6$-DMSO) δ 8.59-8.57 (m, 1H), 8.54-8.50 (m, 1H), 7.88-7.82 (m, 2H), 7.61-7.58 (m, 2H), 7.56-7.52 (m, 1H), 3.75 (s, 3H), 2.13 (s, 3H).

II. Biological Data

Example 1

PI3K and VPS34 Enzyme Assays

Cloning, Expression, and Purification of PI3Ks and VPS34

The catalytic subunits of PI3Ks are cloned into either pDEST8 (p110 alpha) or pDEST10 (p110beta, p110delta, and p110gamma) as N-terminal His tagged fusion proteins using the Gateway system (Invitrogen, catalog#11804-010 for pDEST8 and 11806-015 for pDEST10). The sequences are verified before recombinant protein expression using the Baculovirus Expression System with Gateway® Technology. The accession numbers for the subunits are as follows:
p110 alpha (GB: U79143)
p110 beta (GB: S67334)
p110delta (GB: U86453)
p110gamma (GB: X83368)
The regulatory subunits of PI3Ks are cloned into pDEST8 as un-tagged protein using the Gateway system (Catalog#11804-010). The sequences are verified before recombinant protein expression using the Baculovirus Expression System with Gateway® Technology. The accession numbers for the subunits are as following:
p85 alpha (GB: BC030815)
p101 (GB: AB028925)

VPS34 (accession number GB: BC033004) is cloned into pDEST20-Thombin as N-terminal GST tagged fusion proteins using the Gateway system (Invitrogen, catalog#11804-013). The sequences are verified before recombinant protein expression using the Baculovirus Expression System with Gateway® Technology.

For expression of the p110 complexes, the p85 (MOI of 4) is co-infected with p110 alpha, beta, and delta respectively (1 MOI) in SF9 cells and harvested at 60 hours post co-infection. P110 gamma was infected at 1 MOI and harvested at 60 hours post infection.

VPS34 is infected at 1 MOI in SF9 cells and harvested 72 hours post infection.

For purification, PI3Ks are purified by Ni-NTA Agarose (Qiagen #30250) followed by Mono Q 10/100 GL (Ge Healthcare #17-5167-01). VPS34 is purified by Glutathione Sepharose 4 Fast Flow (GE Healthcare #17-5132-03) followed by HiTrap Q (GE Healthcare #17-1153-01).

PI3K Assay Conditions

1) Human PI3Kα Enzyme Assay Method 0.5 uL compounds in DMSO are added to wells of a 384 well microtitre plate (Corning 3575). At room temperature: 10 ul PI3K reaction buffer (50 mM Hepes, 5 mM DTT, 150 mM NaCl, 10 mM beta-glycerophosphate, 10 mM MgCl2, 0.25 mM sodium cholate and 0.001% CHAPS, pH 7.00) containing ATP (25 uM, Promega) is added followed immediately by 10 ul PI3K reaction buffer containing di-C8 PI(4, 5)P2 (3.5 uM, CellSignals) and PI3Kalpha (0.4875 nM, Millennium Protein Sciences Group) and the mixture is incubated with shaking at room temperature for 30 minutes. Then 5 ul PI3K stop mix (50 mM Hepes, 5 mM DTT, 150 mM NaCl, 0.01% Tween-20, 15 mM EDTA and 25 nM biotin-PI (3,4,5)P3 (Echelon) is added to quench the reaction followed immediately by addition of 5 ul HTRF detection mix (50 mM Hepes, 5 mM DTT, 150 mM NaCl, 0.01% Tween-20, 40 mM KF, 10 nM GST:GRP-1 PH domain (Millennium Protein Sciences Group), 15 nM Streptavidin-XL (CisBio) and 0.375 nM anti-GST Eu++ antibody (CisBio) at pH 7.00). The plates are then incubated for 1 hour at room temperature with shaking and then read on a BMG PheraStar Plus reader.

2) Human PI3K beta, delta and gamma isoforms are tested using the procedure described for PI3K alpha above but with the following changes: PI3K beta (5.25 nM), PI3K delta (0.75 nM) and PI3K gamma (5 nM). All isoforms supplied by Millennium Protein Science Group.

3) VPS34 is Assayed Using Adapta™ Universal Kinase Assay Kit (Invitrogen).

Example 2

PI3K Cell Assays

Forkhead Redistribution Assay

Inhibition of PI3K in cells can be assessed using the Forkhead Redistribution Assay (BioImage). FoxolA fused to EGFP (FoxolA-EGFP) expressed in U2OS osteosarcoma cells localizes to the cytoplasm when the PI3K pathway is actively signaling. Inactivation of pathway signaling leads to a translocation of the protein from the cytoplasm to the nucleus. Therefore, pathway inhibition can be measured by quantifying the fluorescent intensity of FoxolA-EGFP within the nucleus.

U2OS cells constitutively expressing FoxolA-EGFP (6500 cells/well) are plated onto the inner 60 wells of 96 well dishes (BD Falcon OPTILUX black clear bottom) in 100 µL of cell culture media (DMEM (Invitrogen) containing 10% Fetal Bovine Serum (HyClone) and 1% Penicillin-Streptavidin (Invitrogen) and grown overnight in a humidified chamber at 37° C. The cell culture media is removed and the cells are rinsed with 100 µL of low serum media (DMEM containing 0.933% Fetal Bovine Serum and 1% Penicillin-Streptavadin) and incubated in 75 µL of low serum media for 1 hour in a humidified chamber at 37° C. Test compounds (25 µL) at multiple concentrations suspended in DMEM containing 1% Penicillin-Streptavadin are added to cells and incubated in a humidified chamber at 37° C. for 1 hour. The media is removed and the cells are fixed in 100 µL of 4% paraformaldehyde in phosphate buffered saline (PBS) for 10 min and then washed with 100 µL of PBS. DRAQ5 mix (100 µL, Alexis Biochemicals) diluted 1:5000 in PBS containing RNAase (1:10,000, Sigma) is added to cells for 30 minutes. The plates are then imaged (16 fields per well) using an Opera Imager (Evotec) and FoxolA-EGFP fluorescent intensity within the nucleus (DRAQ5-positive) is quantified using Acapella Software (Evotec). Concentration response curves are generated by calculating the nuclear fluorescent intensity of Foxo-1A EGFP in test compound-treated samples and concentrations producing 50% inhibition ($IC_{50}$ values) relative to the positive control are determined from those curves.

Example 3

Anti-Proliferation Assay

ATPlite Assay

The ATPLite™ (Perkin-Elmer) Assay measures cellular adenosine-triphosphate (ATP) through the generation of a luminescent signal formed from the ATP dependent enzyme firefly luciferase. The luminescent signal intensity can be used as a measure of cellular proliferation, and therefore the anti-proliferative effects of PI3K inhibitors.

Test compounds (4 µL in 100% DMSO) are diluted in 75 µL of Hanks Buffered Saline Solution (Invitrogen). The diluted test compounds (8 pt) are then added to 384-well TC-treated Black/Clear plates (Falcon). HCT-116 cells (American Type Culture Collection) maintained in McCoy's 5a modified media (Invitrogen) containing 10% Fetal Bovine Serum and 1% Penicillin-Streptavadin are added at 1000 cells per well. H460 cells (American Type Culture Collection) maintained in RPMI 1640 containing 10% Fetal Bovine Serum and 1% Penicillin-Streptavadin are added at 1500 cells per well. The cells are then incubated with compound in a humidified chamber at 37° C. for 72 hours. The plates are then removed from the cell culture chambers and allowed to equilibrate to room temperature for 30 min. All but 25 µL of cell culture media is removed from each well, and 25 µl of ATPlite reagent (Perkin Elmer) is added to each well. Luminescence is measured within 5 minutes of adding the ATPlite reagent on a LEADSeeker Luminescence Counter (GE Healthcare Life Sciences). Concentration response curves are generated by calculating the luminescence decrease in test compound-treated samples relative to DMSO-treated controls, and growth inhibition ($IC_{50}$) values are determined from those curves.

As detailed above, compounds of the invention inhibit PI3K. In certain embodiments, compounds inhibit one or more isoforms of PI3K. In other embodiments, compounds of the invention inhibit PI3Kalpha and have an IC50>1.0 µM. For example, these compounds include compounds 1, 4, 8, 24, 33, 44, and 84. In other embodiments, compounds of the invention have an IC50<1.0 µM but >0.1 µM. For example, these compounds include compounds 3, 7, 9, 10, 14, 17, 18, 21, 25, 26, 28, 29, 30, 35, 38, 40, 42, 43, 46, 47, 48, 50, 56, 59, 60, 65, 67, 70, 71, 72, 75, 78, 79, and 83. In still other embodiments, compounds of the invention have an IC50<0.1 µM. For example, these compounds include compounds 2, 5, 6, 11, 12, 13, 15, 16, 19, 20, 22, 23, 27, 31, 32, 34, 36, 37, 39, 41, 45, 49, 51, 52, 53, 54, 55, 57, 58, 61, 62, 63, 64, 66, 68, 69, 73, 74, 76, 77, 80, 81, 82, 85, 86, and 87.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

The invention claimed is:
1. A compound of formula I:

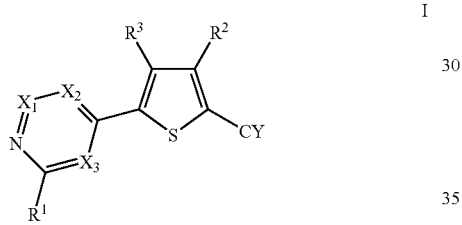

I or a pharmaceutically acceptable salt thereof, wherein:
$R^1$ is —$R^{1b}$, —$V_1$—$R^{1c}$, -$T_1$-$R^{1b}$, or —$V_1$-$T_1$-$R^{1b}$ wherein:
$V_1$ is —$NR^{1a}$—, —$NR^{1a}$—C(O)—, —$NR^{1a}$—C(S)—, —$NR^{1a}$—C($NR^{1a}$)—, $NR^{1a}$C(O)O—, $NR^{1a}$C(O)$NR^{1a}$—, $NR^{1a}$C(O)S—, $NR^{1a}$C(S)O—, $NR^{1a}$C(S)$NR^{1a}$—, $NR^{1a}$C(S)S—, —$NR^{1a}$C($NR^{1a}$)O—, —$NR^{1a}$C($NR^{1a}$)$NR^{1a}$—, —$NR^{1a}$S(O)_2$—, —$NR^{1a}$S(O)_2$$NR^{1a}$—, —C(O)—, —$CO_2$—, —C(O)$NR^{1a}$—, C(O)$NR^{1a}$O—, —$SO_2$—, or —$SO_2NR^{1a}$—;
each occurrence of $R^{1a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
$T_1$ is an optionally substituted $C_1$-$C_6$ alkylene chain wherein the alkylene chain optionally is interrupted by —N($R^{1a}$)—, —O—, —S—, —S(O)—, —S(O)_2$—, —C(O)—, —C(O)O—, C(O)N($R^{1a}$)—, —S(O)_2$N($R^{1a}$)—, —OC(O)N($R^{1a}$)—, —N($R^{1a}$)C(O)—, —N($R^{1a}$)$SO_2$—, —N($R^{1a}$)C(O)O—, —N$R^{1a}$C(O)N($R^{1a}$)—, —N($R^{1a}$)S(O)_2$N ($R^{1a}$) OC(O)—, or —C(O)N($R^{1a}$)—O— wherein $T_1$ forms part of an optionally substituted 3-7 membered cycloaliphatic or heterocyclyl ring;

each occurrence of $R^{1b}$ is independently hydrogen, halogen, —CN, —$NO_2$, —N($R^{1a}$)_2$, —$OR^{1a}$, —$SR^{1a}$, —S(O)_2$$R^{1a}$, —C(O)$R^{1a}$, —C(O)$OR^{1a}$, —C(O)N($R^{1a}$)_2$, —S(O)_2$N($R^{1a}$)_2$, —OC(O)N ($R^{1a}$)_2$, —N($R^{1a}$)C(O)$R^{1a}$, —N($R^{1a}$)$SO_2R^{1a}$, —N($R^{1a}$)C(O)$OR^{1a}$, —N($R^{1a}$)C(O)N($R^{1a}$)_2$, or —N($R^{1a}$)$SO_2$N($R^{1a}$)_2$, or an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{1c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or $R^{1a}$ and $R^{1c}$ taken together with a nitrogen atom to which they are bound form an optionally substituted 4-7-membered heterocyclyl ring having 0-1 additional heteroatoms independently selected from nitrogen, oxygen, or sulfur;

$R^2$ is halogen, —W—$R^6$, or —$R^6$, wherein:
W is —O—, N($R^{2a}$)—, —S—, —S(O)—, —S(O)_2$—, —C(O)—, —$CO_2$—, —C(O)$NR^{2a}$—, —N($R^{2a}$)C(O)—, —N($R^{2a}$)$CO_2$—, —S(O)_2$$NR^{2a}$—, —N($R^{2a}$)S(O)_2$—, —OC(O)N($R^{2a}$)—, —N($R^{2a}$)C(O)N$R^{2a}$—, —N($R^{2a}$)S(O)_2$N($R^{2a}$)—, or —OC(O)—;

$R^{2a}$ is hydrogen or an optionally substituted $C_{1-4}$ aliphatic, and $R^6$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$R^3$ is H, —CN, halogen, —Z—$R^5$, $C_{1-6}$ aliphatic, or 3-10-membered cycloaliphatic, wherein:
Z is selected from an optionally substituted $C_{1-3}$ alkylene chain, —O—, —N($R^{3a}$)—, —S—, —S(O)—, —S(O)_2$—, —C(O)—, —$CO_2$—, —C(O)$NR^{3''}$-, —N($R^{3a}$)C(O)—, —N($R^{3a}$)$CO_2$—, —S(O)_2$$NR^{3a}$—, —N($R^{3a}$)S(O)_2$—, —OC(O)N($R^{3a}$)—, —N($R^{3a}$)C(O)N$R^{3a}$—, —N($R^{3a}$)S(O)_2$N($R^{3a}$)—, or —OC(O)—;

$R^{3a}$ is hydrogen or an optionally substituted $C_{1-4}$ aliphatic, and $R^5$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

CY is 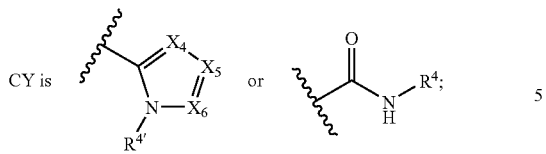

each occurrence of $R^4$ and $R^{4'}$ is independently H, —Z—$R^6$, $C_{1-6}$ aliphatic, or 3-10-membered cycloaliphatic, wherein:

Z is selected from an optionally substituted $C_{1-3}$ alkylene chain, —O—, —N($R^{4a}$)—, —S(O)—, —S(O)$_2$—, —C(O)—, —CO$_2$—, —C(O)N$R^{4a}$—, —N($R^{4a}$)C(O)—, —N($R^{4a}$)CO$_2$—, —S(O)$_2$N$R^{4a}$—, —N($R^{4a}$)S(O)$_2$—, —OC(O)N($R^{4a}$)—, —N($R^{4a}$)C(O)N$R^{4a}$—, —N($R^{4a}$)S(O)$_2$N($R^{4a}$)—, or —OC(O)—;

$R^{4a}$ is hydrogen or an optionally substituted $C_{1-4}$ aliphatic, and $R^6$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and $X_1$, $X_2$, $X_3$, $X_4$, $X_5$ and $X_6$ are each independently N or C$R^7$, wherein each occurrence of $R^7$ is independently hydrogen, —CN, halogen, —Z—$R^8$, optionally substituted $C_{1-6}$ aliphatic, or optionally substituted 3-10-membered cycloaliphatic, wherein:

Z is selected from an optionally substituted $C_{1-3}$ alkylene chain, —O—, —N($R^{7a}$)—, —S—, —S(O)—, —S(O)$_2$—, —C(O)—, —CO$_2$—, —C(O)N$R^{7a}$—, —N($R^{7a}$)C(O)—, —N($R^{7a}$)CO$_2$—, —S(O)$_2$N$R^{7a}$—, —N($R^{7a}$)S(O)$_2$—, —OC(O)N($R^{7a}$)—, —N($R^{7a}$)C(O)N$R^{7a}$—, —N($R^{7a}$)S(O)$_2$N($R^{7a}$)—, or —OC(O)—;

$R^{7a}$ is hydrogen or an optionally substituted $C_{1-4}$ aliphatic, and $R^8$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, provided that:

a) when CY is —CONH$R^4$, then $R^2$ is an optionally substituted group selected from 6-10-membered aryl, or 5-10-membered heteroaryl having 1-5 heteroatoms independently selected from nitrogen, oxygen, or sulfur.

2. The compound of claim 1, wherein (a) $R^2$ is an optionally substituted 6-10-membered aryl, or 5-10-membered heteroaryl having 1-5 heteroatoms independently selected from nitrogen, oxygen, or sulfur; or (b) $R^1$ is —$V_1$—$R^{1c}$.

3. The compound of claim 2, wherein the compound is represented by:

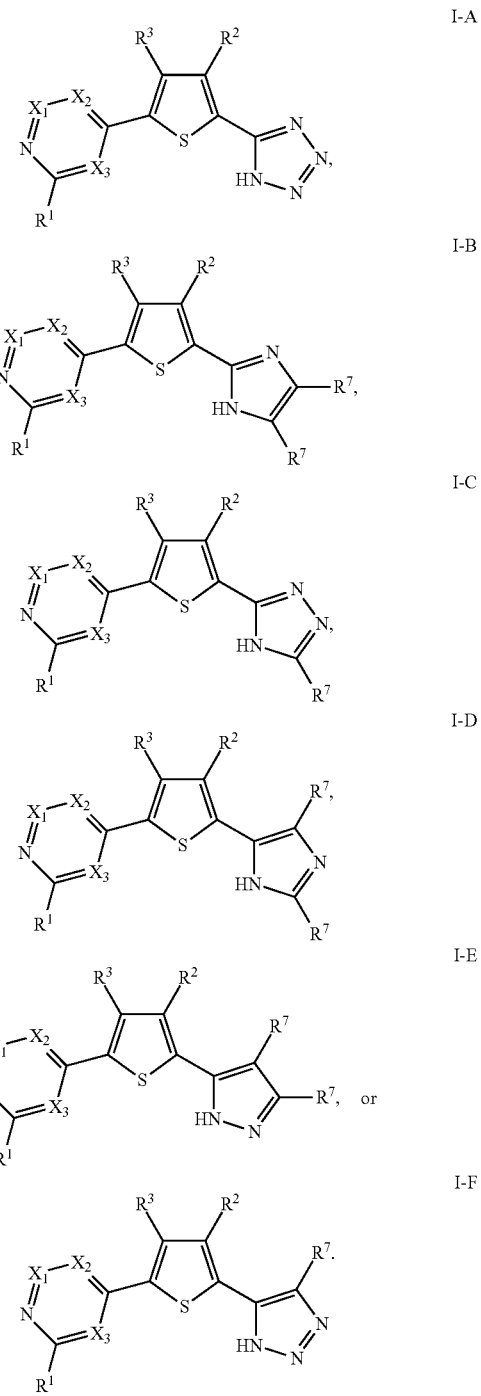

4. The compound of claim 3, wherein $X_2$ is N, and $X_1$ and $X_3$ are each C$R^7$.

5. The compound of claim 3, wherein $X_3$ is N, and $X_1$ and $X_2$ are each C$R^7$.

6. The compound of claim 3, wherein $X_1$, $X_2$ and $X_3$ are each C$R^7$.

7. The compound of claim 1, wherein $R^2$ is a 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, optionally substituted with 1-4 independent occurrences of $R^9$, wherein $R^9$ is —$R^{9a}$, -$T_2$-$R^{9d}$, or —$V_2$-$T_2$-$R^{9d}$, and:

each occurrence of $R^{9a}$ is independently halogen, —CN, —$NO_2$, —$R^{9c}$, —$N(R^{9b})_2$, —$OR^{9b}$, —$SR^{9c}$, —$S(O)_2R^{9c}$, —$C(O)R^{9b}$, —$C(O)OR^{9b}$, —$C(O)N(R^{9b})_2$, —$S(O)_2N(R^{9b})_2$, —$OC(O)N(R^{9b})_2$, —$N(R^{9e})C(O)R^{9b}$, —$N(R^{9e})SO_2R^{9c}$, —$N(R^{9e})C(O)OR^{9b}$, —$N(R^{9e})C(O)N(R^{9b})_2$, or —$N(R^{9e})SO_2N(R^{9b})_2$, or two occurrences of $R^{9b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{9b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{9d}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{9d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{9e}$ is independently hydrogen or an optionally substituted $C_{1-6}$ aliphatic group;

each occurrence of $V_2$ is independently —$N(R^{9e})$—, —O—, —S—, —S(O)—, —$S(O)_2$—, —C(O)—, —C(O)O—, —$C(O)N(R^{9e})$—, —$S(O)_2N(R^{9e})$—, —$OC(O)N(R^{9e})$—, —$N(R^{9e})C(O)$—, —$N(R^{9e})SO_2$—, —$N(R^{9e})C(O)O$—, —$NR^{9e}C(O)N(R^{9e})$—, —$N(R^{9e})SO_2N(R^{9e})$—, —OC(O)—, or —$C(O)N(R^{9e})$—O—; and $T_2$ is an optionally substituted $C_1$-$C_6$ alkylene chain wherein the alkylene chain optionally is interrupted by —$N(R^{7a})$—, —O—, —S—, —S(O)—, —$S(O)_2$—, —C(O)—, —C(O)O—, —$C(O)N(R^{7a})$—, —$S(O)_2N(R^{7a})$—, —$OC(O)N(R^{7a})$—, —$N(R^{7a})C(O)$—, —$N(R^{7a})SO_2$—, —$N(R^{7a})C(O)O$—, —$NR^{7a}C(O)N(R^{7a})$—, —$N(R^{7a})S(O)_2N(R^{7a})$—, —OC(O)—, or —$C(O)N(R^{7a})$—O— or wherein $T_3$ or a portion thereof optionally forms part of an optionally substituted 3-7 membered cycloaliphatic or heterocyclyl ring.

8. The compound of claim 7, wherein:

$R^2$ is a phenyl group substituted with 1-3 independent occurrences of halo, $C_{1-3}$ alkyl, CN, $C_{1-3}$ haloalkyl, —$OC_{1-3}$ alkyl, —$OC_{1-3}$ haloalkyl, —$NHC(O)C_{1-3}$ alkyl, —$NHC(O)NHC_{1-3}$ alkyl, $NHS(O)_2C_{1-3}$ alkyl, or —C(O)H.

9. The compound of claim 1, wherein the compound has the structure of formula II:

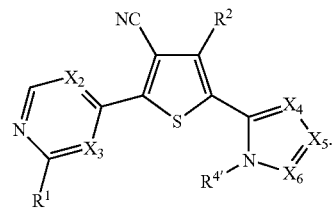

II

10. The compound of claim 9, wherein:
$R^1$ is —$V_1$—$R^{1c}$, where $V_1$ is —$NR^{1a}CO$—, or —$N(R^{1a})_2$; and
$R^2$ is a phenyl group substituted with 1-3 independent occurrences of halo, $C_{1-3}$ alkyl, —CN, $C_{1-3}$ haloalkyl, —$OC_{1-3}$ alkyl, —$OC_{1-3}$ haloalkyl, —$NHC(O)C_{1-3}$ alkyl, —$NHC(O)NHC_{1-3}$ alkyl, $NHS(O)_2C_{1-3}$ alkyl, or —C(O)H.

11. The compound of claim 10, wherein $X_4$ is N, and $X_5$ and $X_6$ are each $CR^7$.

12. The compound of claim 10, wherein $X_4$ is N, $X_5$ is N, and $X_6$ is $CR^7$.

13. The compound of claim 1, wherein the compound has the structure of formula III:

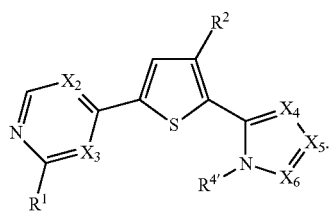

III

14. The compound of claim 13, wherein:
$R^1$ is —$V_1$—$R^{1c}$, where $V_1$ is —$NR^{1a}CO$—, or —$N(R^{1a})_2$; and
$R^2$ is a phenyl group substituted with 1-3 independent occurrences of halo, $C_{1-3}$ alkyl, —CN, $C_{1-3}$ haloalkyl, —$OC_{1-3}$ alkyl, —$OC_{1-3}$ haloalkyl, —$NHC(O)C_{1-3}$ alkyl, —$NHC(O)NHC_{1-3}$ alkyl, $NHS(O)_2C_{1-3}$ alkyl, or —C(O)H.

15. The compound of claim 14, wherein $X_4$ is N, and $X_5$ and $X_6$ are each $CR^7$.

16. The compound of claim 14, wherein $X_4$ is N, $X_5$ is N, and $X_6$ is $CR^7$.

17. A composition comprising a compound of claim 1 and a pharmaceutically acceptable carrier.

18. A method of treating an inflammatory disorder in a patient comprising administering to said patient a therapeutically effective amount of a compound of claim 1.

19. The method of claim 18, wherein the inflammatory disorder is selected from allergies/anaphylaxis, acute and chronic inflammation, and rheumatoid arthritis.

20. A method for inhibiting PI3K activity in a patient comprising administering a composition comprising an amount of a compound of claim 1 effective to inhibit PI3K activity in the patient.

21. A method of treating a cardiovascular disorder in a patient comprising administering to said patient a therapeutically effective amount of a compound of claim 1 wherein the cardiovascular disorder is selected from thrombosis, hypertension, cardiac hypertrophy, and heart failure.

* * * * *